US009023635B2

(12) United States Patent
Bayer et al.

(10) Patent No.: US 9,023,635 B2
(45) Date of Patent: May 5, 2015

(54) BACTERIAL METHODS

(75) Inventors: Travis Scott Bayer, London (GB); Jennifer Adele Samson, London (GB)

(73) Assignee: Imperial Innovations Limited, London (GB)

( * ) Notice: Subject to any disclaimer, the term of this patent is extended or adjusted under 35 U.S.C. 154(b) by 86 days.

(21) Appl. No.: 13/884,793

(22) PCT Filed: Nov. 11, 2011

(86) PCT No.: PCT/GB2011/052210
§ 371 (c)(1),
(2), (4) Date: Aug. 20, 2013

(87) PCT Pub. No.: WO2012/063084
PCT Pub. Date: May 18, 2012

(65) Prior Publication Data
US 2014/0206064 A1 Jul. 24, 2014

(30) Foreign Application Priority Data

Nov. 11, 2010 (GB) .................................. 1019086.6

(51) Int. Cl.
| | |
|---|---|
| C12N 1/00 | (2006.01) |
| C12N 1/12 | (2006.01) |
| C12N 15/75 | (2006.01) |
| C07K 14/32 | (2006.01) |
| C12N 3/00 | (2006.01) |
| C12N 9/12 | (2006.01) |

(52) U.S. Cl.
CPC ................ *C12N 15/75* (2013.01); *C07K 14/32* (2013.01); *C12N 3/00* (2013.01); *C12N 9/12* (2013.01)

(58) Field of Classification Search
None
See application file for complete search history.

(56) References Cited

U.S. PATENT DOCUMENTS

| | | | |
|---|---|---|---|
| 3,276,840 | A | 10/1966 | Sierra |
| 5,614,375 | A | 3/1997 | Citri |
| 5,795,730 | A | 8/1998 | Tautvydas |
| 6,872,539 | B2 | 3/2005 | Rotman |
| 2005/0136508 | A1 | 6/2005 | Ponce |
| 2009/0042956 | A1 | 2/2009 | Bozik et al. |
| 2011/0086797 | A1* | 4/2011 | Dworkin .................... 514/3.1 |

FOREIGN PATENT DOCUMENTS

| | | |
|---|---|---|
| WO | WO 03/063887 | 8/2003 |
| WO | WO 2009/042956 | 4/2009 |

OTHER PUBLICATIONS

Akemichi, et al. 1984 "Changes in the specificity of germinants for *Bacillus megaterium*spores by p-chloromercuribenzoate treatment" Database CA, Chemical abstract service.
Anderson, et al, 2006 "Environmentally controlled invasion of Cancer cells by engineered bacteria" *Journal Mol Biol.*355(4): 619-27.
Barbe, et al 2006 "The use of clostridial spores for cancer treatment"*Journal of Applied Microbiology*; 101: 571-578.
Barbe et al. 2009 "From a consortium sequence to a unified sequence: the *Bacillus subtillis*168 reference genome a decade later"*Microbiology*: 115(6), 1758-1775.
Bayer, T 2010, "Rewriting and repurposing biological systems" Powerpoint presentation, Imperial College, London (in 22 pages).
Breinbauer, et al. 2003 "Azide—alkyne coupling: a powerful reaction for bioconjugate chemistry" *Chemibiochem.*4(11): 1147-9.
Brooljmans, et al. 2009 "Hydrocarbon-degrading bacteria: the oilspill clean-up crew" *Microbial Biotechnology*, 2(6): 587-594.
Casula, et al. 2002 "*Bacilus*proiotics: Spore germinationin the gastrointestinal tract" *Applied Environmental Microbiology*68(5): 2344-2352.
Chen, et al 2009 "Degradability of n-hexedecarie by *Bacillus cereus*DG01 isolated from oil contaminated soil from Daqing oil filed, China" *International Journal of Environment and Pollution*38(1-2): 100-115.
Chiang, et al. 2010 "Secreted production of *Renilla*Luciferase in *Bacillus subtilis*" *AIChE Biotechnology Prog.*26(2): 589-594.
Choct 2006 "Enzymes for the feed industry: past, present and future" *World's Poultry Sci J.*62: 5-16.
Christie, et al. 2007 "Role of chromosomal and plasmid-borne receptor homologues in the response of *Bacillus megaterium*QM BI551 spores to germinants" *Journals of Bacteriology*189(12): 4375-4383.
Cutting et al. 1990 "Genetic Analysis" in *Molecular Biology Methods for Bacillus*, Harwood, C.R. and Cutting, S.M. eds., Jonh Wiley & Sons, Chapter 2 pp. 29-60.
Cutting, et al. 2009 "Oral vaccine delivery by recombinant spore probiotics" *International Reviews of Immunology*, 28(6): 487-505.
Das, et al. 2007 "Crude petroieum-oll biogradation efficiency of *Bacillus subtilus*and *Pseudomonas aeruginosa*strains isolated from a petroleum-oil contaminated soil from North-East India" *Bioresource Technology*, 98(7): 1339-1345.
Dworkin, et al. 2010 "Exit from dormancy in microbial organisms" *Nature Reviews*, 8; 1-9.
Frank 2002 "Minireview: reception dimerization in GH and Erythropoietin action—It takes two to tango, but how?" *Endocrinology*143(1): 2-10.
Fredriksson, et al. 2002 "Protein detection using proximity-dependent DNA ligation assays" *Nature Biotechnology*20: 473-477.
Gareau 2010."Probiotics and the gut microbiota in intestinal health and disease" *Nature Reviews!Gastroenterology& Hepatology*7(9): 503-514.

(Continued)

*Primary Examiner* — Albert Navarro
(74) *Attorney, Agent, or Firm* — Knobbe, Martens, Olson & Bear, LLP

(57) ABSTRACT

A bacterial spore comprising a modified prkC protein, wherein the extracellular domain of the modified prkC protein binds an agent which is not bound by the extracellular domain of the wild-type prkC protein, and wherein the agent is a germinant that stimulates germination of the bacterial spore, or a bacterial spore comprising a modified gerA protein, wherein the gerA protein has been modified such that the spore undergoes germination in the presence of a germinant which does not stimulate germination of a bacterial spore comprising wild-type gerA protein.

23 Claims, 31 Drawing Sheets

(56) References Cited

OTHER PUBLICATIONS

Hall, et al, 2009 "Kinetic optimization of e protein-responsive aptamer beacon" *Biotechnol. Bioeng.* 103: 1049-1059.

Harwood, et al. 2008 "*Bacillus* protein secretion: an unfolding story" *Trends in Microbiology* 16(2): 73-79.

Heap, et al. 2007 "The Clostron: A universal gene knock-out system for the genus *Clostridium*" *Journal of Microbiology Methods* 70: 452-464.

Heap, J.T. et al. 2009 "Development of genetic knock-out systems for clostrida" in *Clostridia Molecular Biology in the Post-genomic Era*. Bruggerman, H. and Gottschalk, G. eds., Chapter 10, pp. 179-198.

Heap, et al. 2010 "The Clostron: Mutagenesis in clostridium refined and streamlined" *Journal of Microbiology Methods*. 80: 49-55.

Hudson, et al. 2001 "Localization of GerAA and GerAC germination protiens in the *Bacillus subtilis* spore" *Journal of Bacteriology*, 183(14): 4317-4322.

Ishii, et al. 2001 "DBTBS, a database of *Bacillus subtilis* promoters and transcription factors" *Nucleic Acids Research*, 29(1): 278-280.

Johannes, et al. 2006 "Directed evolution of enzymes and bisynthetic pathways" *Current Opinion Microbiology* 9(3): 261-267.

Kunst, et al. 1997 "The complete genome sequence of the gram-positive bacterium *Bacillus subtilis*" *Nature* 390, 249-256.

Kuo, et al. 2009 "A stably engineered, suicidal strain of *Listeria monocytogenes* delivers protein and/or DNA to fully differentiated intestinal epithelial monolayers" *Moleculas Pharmaceutics* 6(4): 1052-1061.

Lei, et al. 2006 "Microbial biosensors" *Analtica Chimica Acta* 568(1-2): 200-210.

Leser, et al. 2008 "Germination and outgrowth of *Bacillus subtilus* and *Bacillus licheniformis* spores in the gastrointestinal tract of pigs" *Journal of Applied Microbiology* 104(4): 1025-33.

Leung, et al. 1989 "A method for random mutagenesis of a defined DNA segment using a modified polymerase chain reaction" *Technique-A Journal of Methods in Cell and Molecular Biology* 1: 11-15

Li, et al. 2004 "Bottlenecks in the expression and secretion of heterologous proteins in *Bacillus subtilus*" *Research in Microbiology* 155(8): 605-610.

Link et al. 2006 "The effect of probiotic BioPlus 2B on feed efficiency and metabolic parameters in swine" *Biologia, Bratisiava* 61(6); 783-787.

Mauriello, et al. 2007 "Germination-independent induction of cellular immune response by *Bacillus subtilis* spores displaying the C fragment of the tetanus toxin" *Vaccine* 25(5): 788-793.

Minton 2003 "Clostridia in cancer therapy" *Nature Reviews Microbiology* 1(3): 237-242.

Nicholson, et al. 1990 "Dramatic increase in negativitysuperhelicity of plasmid DNA in the forespore compartment of sproulating cells of *Bacillus subtilus*" *Journal of Bacteriology* 172(1): 7-14.

Nutiu, et al. 2005 "In vitro selection of structure-switching signaling aptamers" *Angew Chem.* 117: 1085-1089.

Paidhungat, et al 1999 "Isolation and characterization of mutations in *Bacillus subtilis* that allow spore gemination in the novel germinant d-Alanine" *Journal of Bacteriology* 181(11): 3341-3351.

Paidhungat, et al. 2000 "role of Ger proteins in nutrient and nonnutrient triggering of spore germination in *Bactillus subtilis*" *Journal of Bacteriology* 182(9): 2513-2519.

Palffy, et al. 2006 "Bacteria in gene therapy: bactofection versus alternative gene therapy" *Gene Therapy* 13: 101-105.

Parsa, et al. 2007 "Engineeing bacterial vectors for delivery of genes and proteins to antigen-presenting cells" *Molecular Pharmaceutics* 4(1): 4-17.

Potot, et al. 2010 "Display of recombinant proteins on *Bacillus subtilis* spores, using a coat-associated enzyme as the carrier" *Applied and Environmental Microbiology* 76(17): 5926-5933.

Prakash, et al. 2005 "Artificial celll therapy: New strategies for the therapeutic delivery of live bacteria" *Journal of Biomedicine and Biotechnology* 2005(1): 44-56.

Purohit 2003 "Biosensors as molecular tools for use in bioremediation" *Journal of Cleaner Production* 11: 293-301.

Ross, et al. 2010 "The Ger receptor family from sporulating bacteria" *Current issues in Molecular Biology* 12: 147-158.

Russell 1990 "Bacterial spores and chemical sporicidal agents" *Clinical Microbiology Reveiws* 3(2): 99-119.

Salis, et al. 2009 "Automated design of synthetic ribosome binding sites to control protein expression" *Nature Biotechnology* 27: 946-950.

Seelig, et al. 2006 "Enzyme-free nucleic acid logic circuits" *Science* 314: 1585-88.

Shah, et al. 2008 "A eukaryotic-like Ser-Thr kinase signals bacteria to exit dormancy in response to peptidoglycan fragments" *Cell* 135(3): 486-496.

Sierro, et al. 2008 "DBTBS: A database of transcriptional regulation in *Bacillus subtilis* containing upstream intergenic conservation information" *Nucleic Acids Research* 36: D93-D96.

SØrensen, et al. 2006 "Making bio-sense of toxicity: new developments in whole-cell biosensors" *Current Opinion in Biotechnology* 17: 11-16.

Stayton, et al. 1999 "Streptavidin—biotin binding energetics" *Biomolecular Engineering* 16: 39-44.

Tam, et al. 2006 "The intestinal life cycle of *Bacillus subtilis* and close relatives" *Journal of Bacteriolgy* 188(7): 2692-2700.

Terpe 2006 "Overview of bacterial expression systems for heterologous protein: from molecular and biochemical fundamentals to commercial systems" *Applied Microbiology and Biotechnology* 72(2): 211-222.

Venkatasubramanian, et al. 1993 "Biochemical analysis of germination mutants to characterize germinant receptors of *Bacillus subtilis* 1604 spores" *J Gen Microbiology* 139(8): 1921-1926.

Westers, et al. 2004 "*Bacillus subtilis* as cell factory for pharmaceutical proteins: a biotechnological approach to optimize the host organism" *Biochimica Biophysica Acta* 1964(1-3): 299-310.

Xiao, et al. 2010 "Clostridial spore germination versus bacilli: Genome mining and current insights" *Food Microbiology*, 28(2): 266-274.

\* cited by examiner

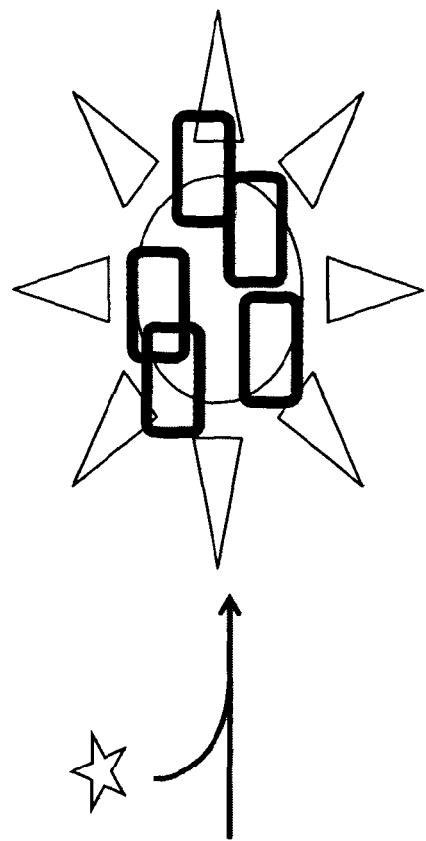
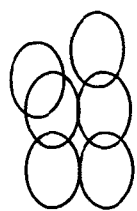
Figure 3

Figure 7
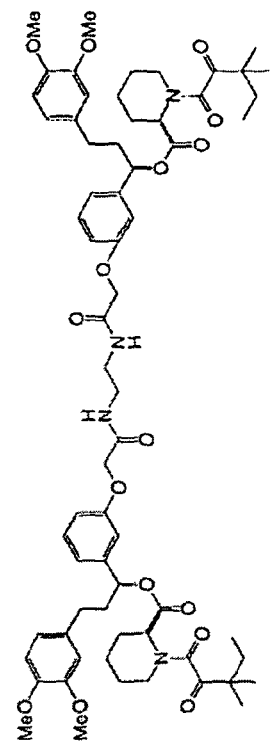
Rapamycin derivative (AP1510)
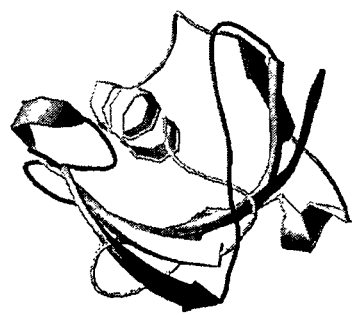
FKBP12
N - | prkC | TM | FKBP12 | - C 3' CACTGTCCCTTATTTCTCCG 5'
5' Biotin - GTGACAGGGA
5' ATAAAGAGGC - Biotin Figure 17
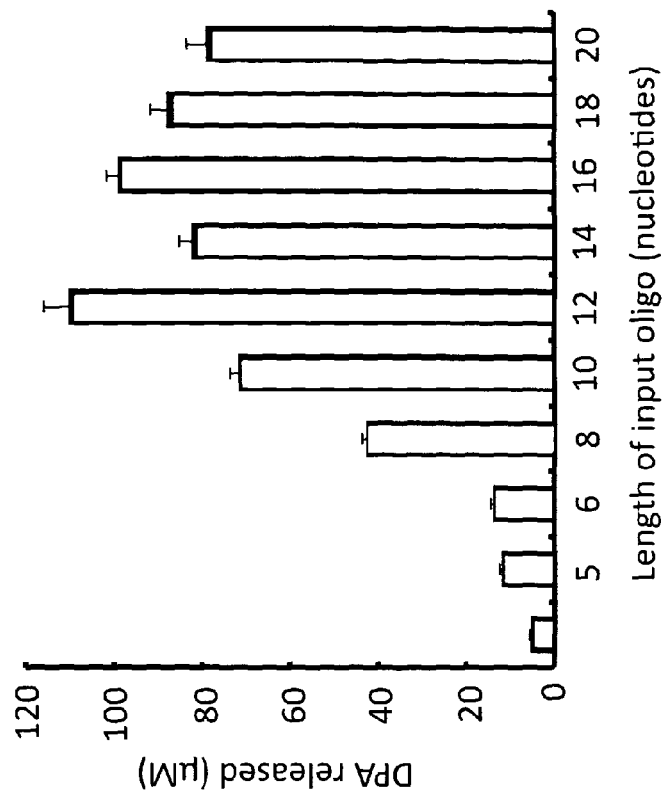
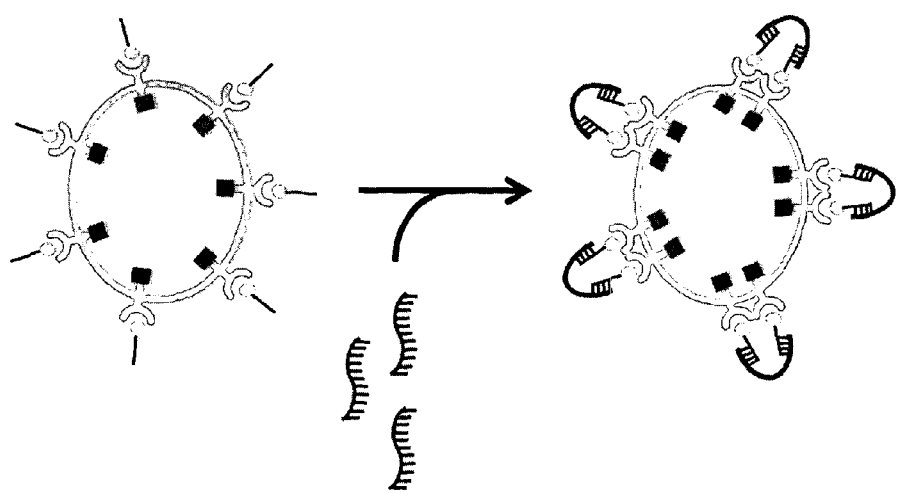

Figure 18
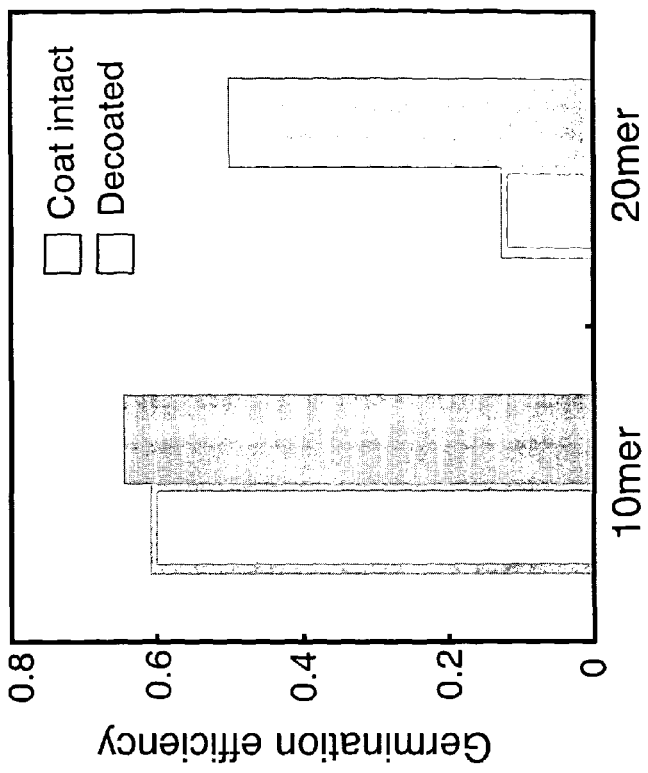
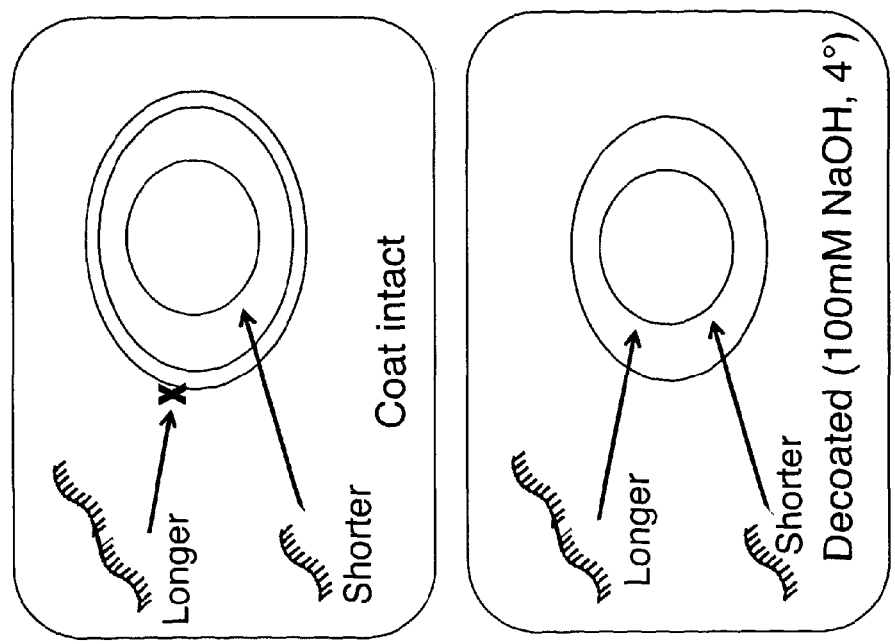

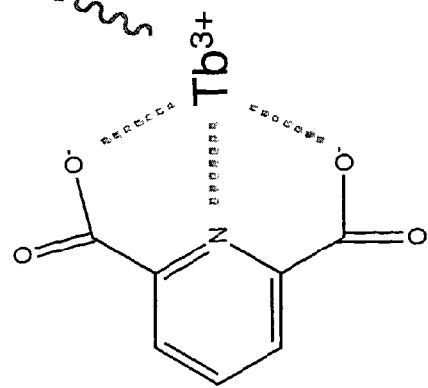
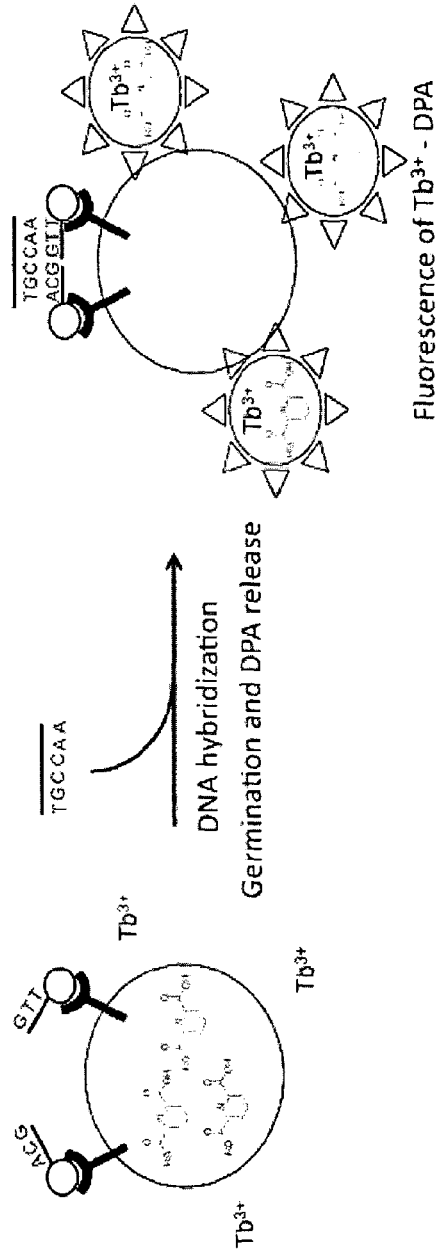
Figure 19

Figure 23
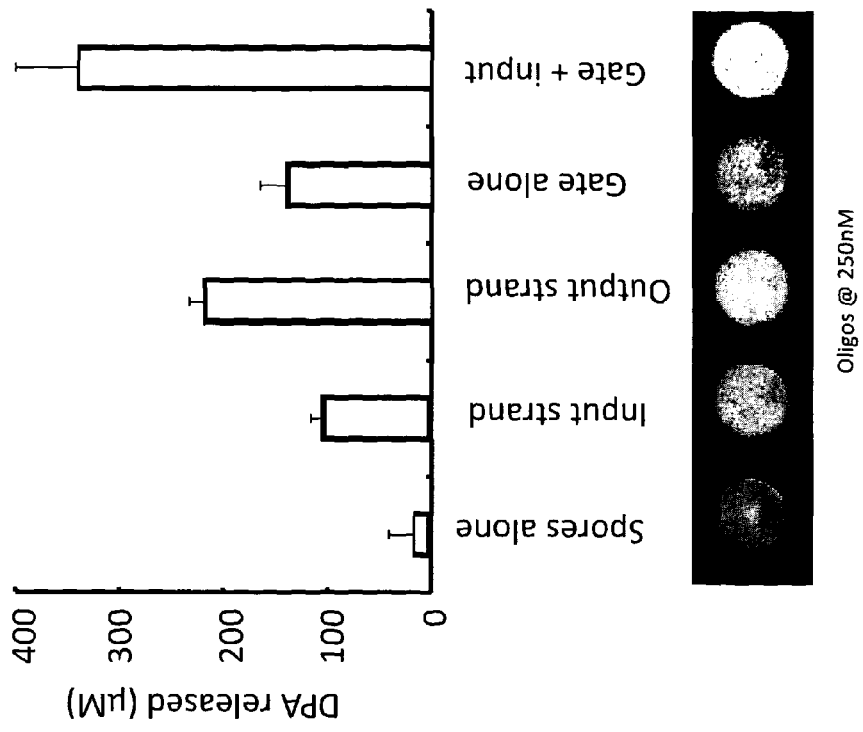
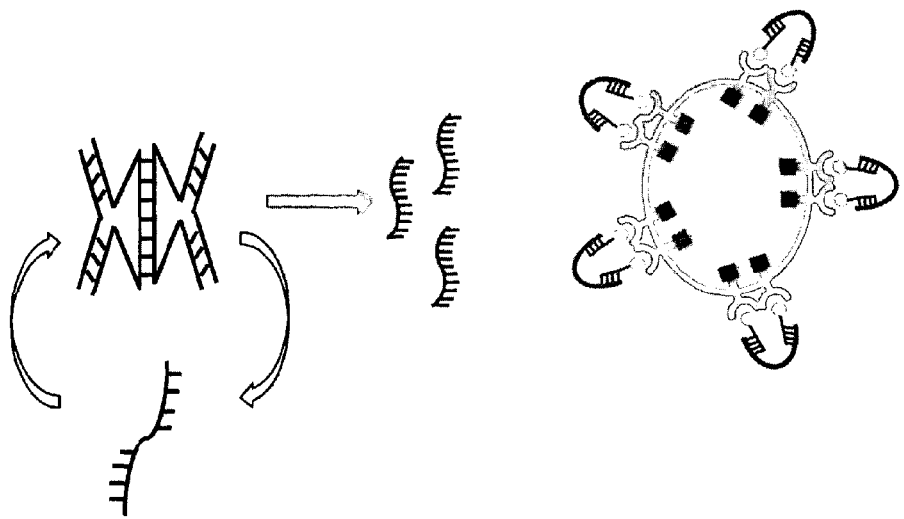

Figure 24
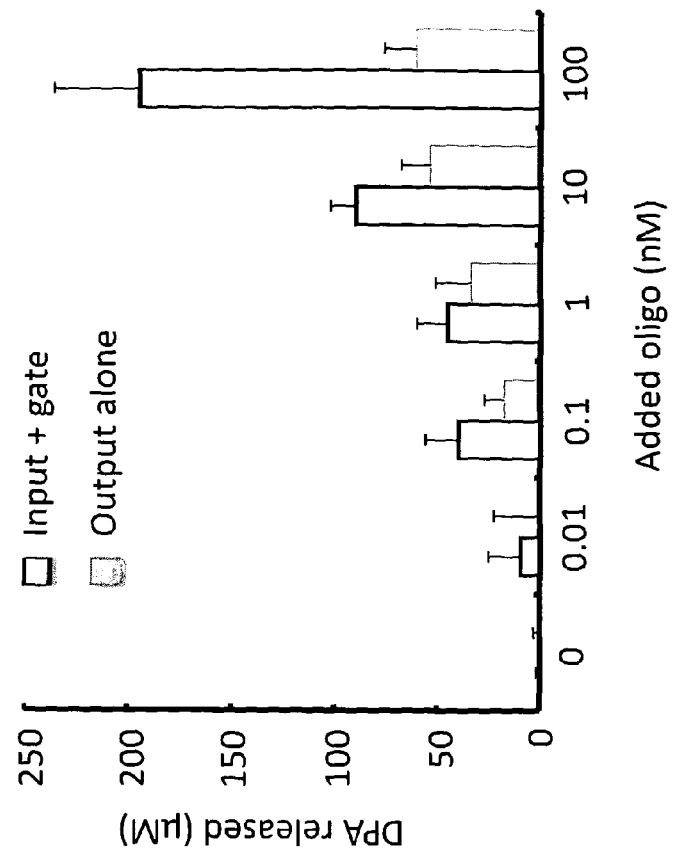
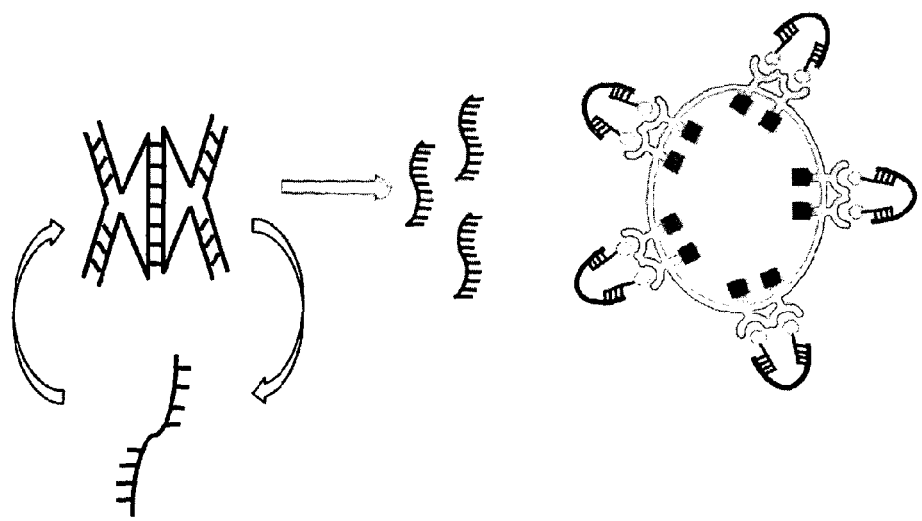

Figure 25
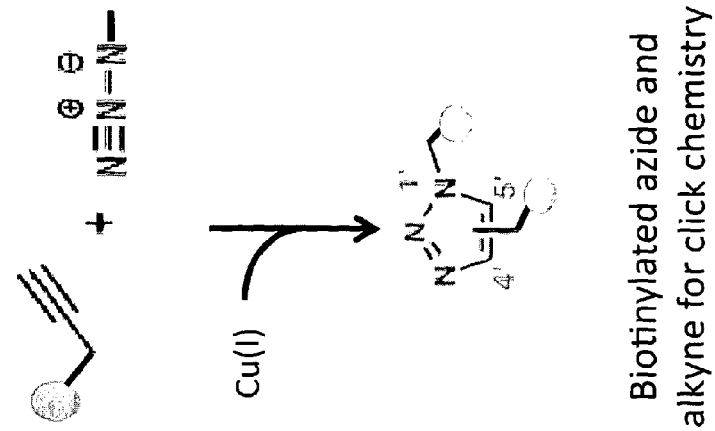
Biotinylated azide and alkyne for click chemistry
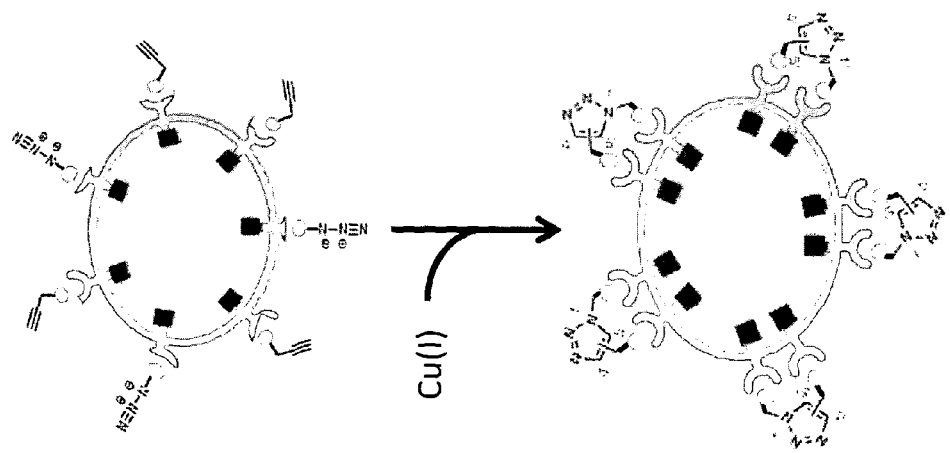

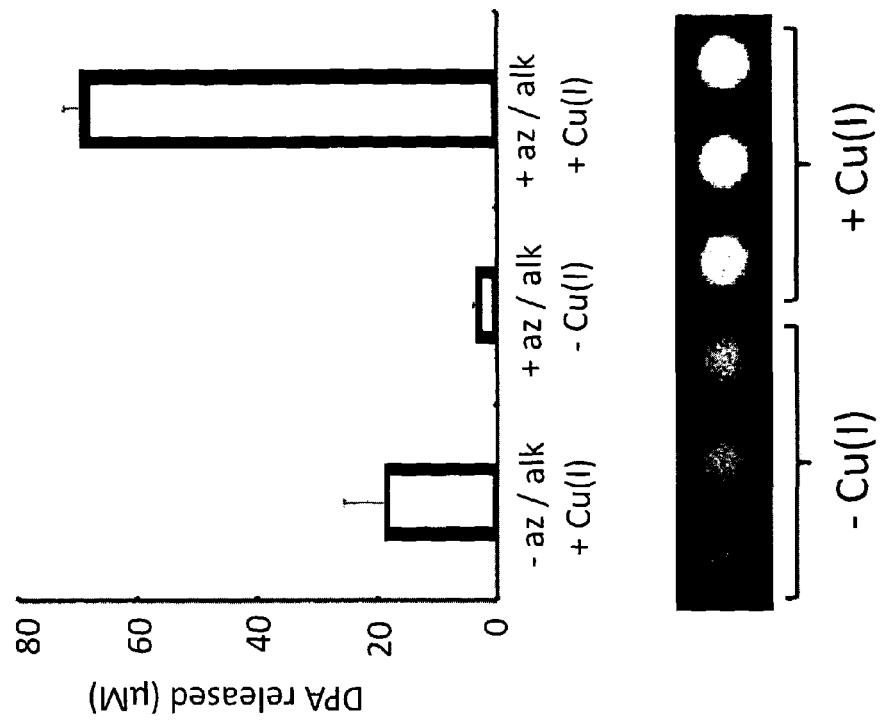
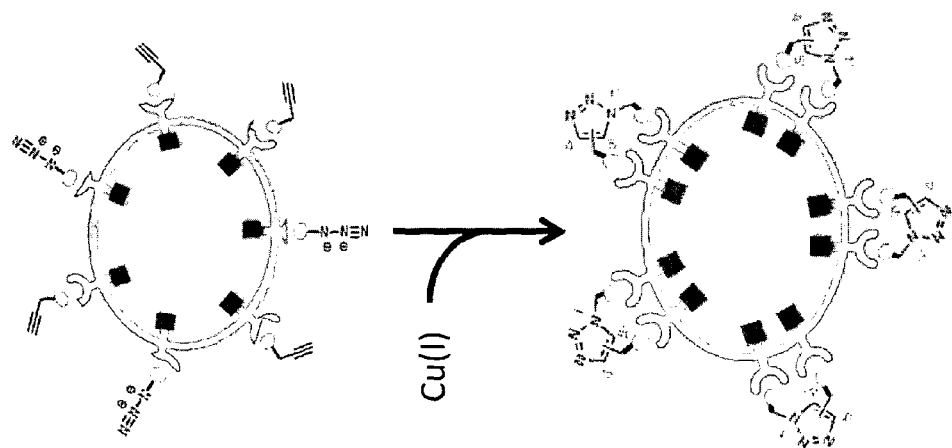
Figure 26

Figure 27
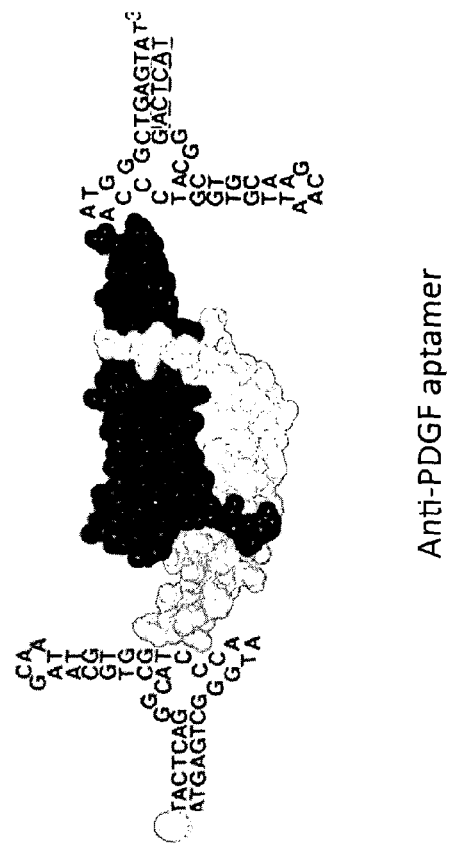
Anti-PDGF aptamer
From Fredriksson et al *Nature Biotech* 2002
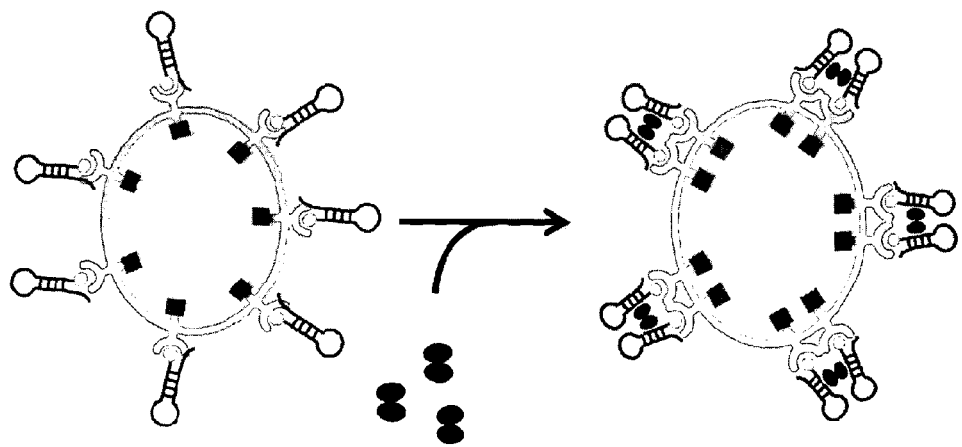

Figure 28
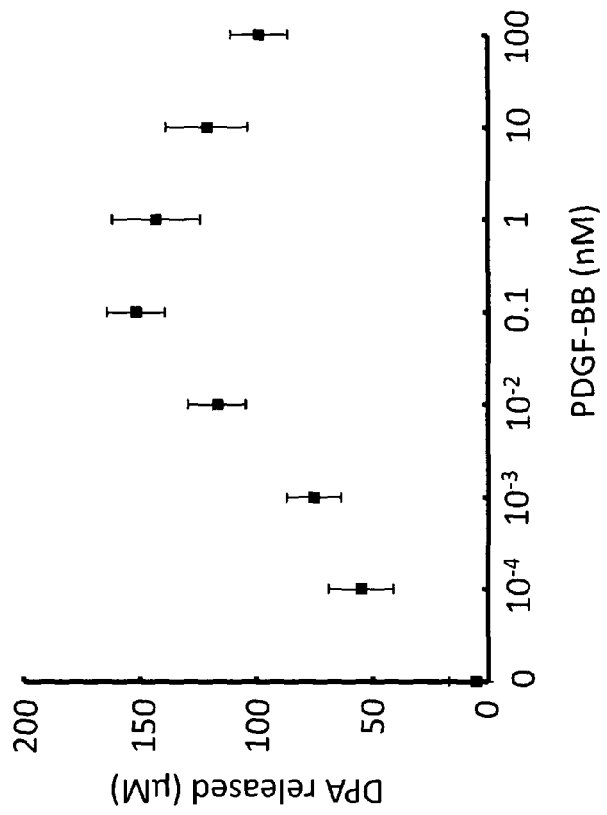
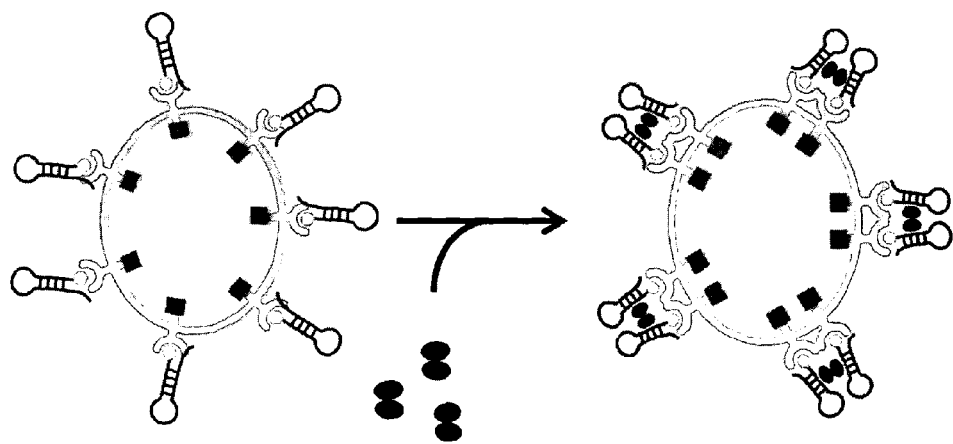

From Hall et al *Biotech Bioeng* 2009

```
                        SEQUENCE LISTING

<160> NUMBER OF SEQ ID NOS: 27

<210> SEQ ID NO 1
<211> LENGTH: 648
<212> TYPE: PRT
<213> ORGANISM: Bacillus subtilis str. 168

<400> SEQUENCE: 1

Met Leu Ile Gly Lys Arg Ile Ser Gly Arg Tyr Gln Ile Leu Arg Val
1               5                   10                  15

Ile Gly Gly Gly Gly Met Ala Asn Val Tyr Leu Ala Glu Asp Ile Ile
            20                  25                  30

Leu Asp Arg Glu Val Ala Ile Lys Ile Leu Arg Phe Asp Tyr Ala Asn
        35                  40                  45

Asp Asn Glu Phe Ile Arg Arg Phe Arg Arg Glu Ala Gln Ser Ala Ser
    50                  55                  60

Ser Leu Asp His Pro Asn Ile Val Ser Ile Tyr Asp Leu Gly Glu Glu
65                  70                  75                  80

Asp Asp Ile Tyr Tyr Ile Val Met Glu Tyr Val Glu Gly Met Thr Leu
                85                  90                  95

Lys Glu Tyr Ile Thr Ala Asn Gly Pro Leu His Pro Lys Glu Ala Leu
            100                 105                 110

Asn Ile Met Glu Gln Ile Val Ser Ala Ile Ala His Ala His Gln Asn
        115                 120                 125

Gln Ile Val His Arg Asp Ile Lys Pro His Asn Ile Leu Ile Asp His
    130                 135                 140

Met Gly Asn Ile Lys Val Thr Asp Phe Gly Ile Ala Thr Ala Leu Ser
145                 150                 155                 160

Ser Thr Thr Ile Thr His Thr Asn Ser Val Leu Gly Ser Val His Tyr
                165                 170                 175

Leu Ser Pro Glu Gln Ala Arg Gly Gly Leu Ala Thr Lys Lys Ser Asp
            180                 185                 190

Ile Tyr Ala Leu Gly Ile Val Leu Phe Glu Leu Leu Thr Gly Arg Ile
        195                 200                 205

Pro Phe Asp Gly Glu Ser Ala Val Ser Ile Ala Leu Lys His Leu Gln
    210                 215                 220

Ala Glu Thr Pro Ser Ala Lys Arg Trp Asn Pro Ser Val Pro Gln Ser
```

```
            225                 230                 235                 240
Val Glu Asn Ile Ile Leu Lys Ala Thr Ala Lys Asp Pro Phe His Arg
                    245                 250                 255

Tyr Glu Thr Ala Glu Asp Met Glu Ala Asp Ile Lys Thr Ala Phe Asp
                    260                 265                 270

Ala Asp Arg Leu Asn Glu Lys Arg Phe Thr Ile Gln Glu Asp Glu Glu
                    275                 280                 285

Met Thr Lys Ala Ile Pro Ile Ile Lys Asp Glu Glu Leu Ala Lys Ala
                    290                 295                 300

Ala Gly Glu Lys Glu Ala Glu Val Thr Thr Ala Gln Glu Asn Lys Thr
305                 310                 315                 320

Lys Lys Asn Gly Lys Arg Lys Lys Trp Pro Trp Val Leu Leu Thr Ile
                    325                 330                 335

Cys Leu Val Phe Ile Thr Ala Gly Ile Leu Ala Val Thr Val Phe Pro
                    340                 345                 350

Ser Leu Phe Met Pro Lys Asp Val Lys Ile Pro Asp Val Ser Gly Met
                    355                 360                 365

Glu Tyr Glu Lys Ala Ala Gly Leu Leu Glu Lys Glu Gly Leu Gln Val
                    370                 375                 380

Asp Ser Glu Val Leu Glu Ile Ser Asp Glu Lys Ile Glu Glu Gly Leu
385                 390                 395                 400

Met Val Lys Thr Asp Pro Lys Ala Asp Thr Thr Val Lys Glu Gly Ala
                    405                 410                 415

Thr Val Thr Leu Tyr Lys Ser Thr Gly Lys Ala Lys Thr Glu Ile Gly
                    420                 425                 430

Asp Val Thr Gly Gln Thr Val Asp Gln Ala Lys Lys Ala Leu Lys Asp
                    435                 440                 445

Gln Gly Phe Asn His Val Thr Val Asn Glu Val Asn Asp Glu Lys Asn
                    450                 455                 460

Ala Gly Thr Val Ile Asp Gln Asn Pro Ser Ala Gly Thr Glu Leu Val
465                 470                 475                 480

Pro Ser Glu Asp Gln Val Lys Leu Thr Val Ser Ile Gly Pro Glu Asp
                    485                 490                 495

Ile Thr Leu Arg Asp Leu Lys Thr Tyr Ser Lys Glu Ala Ala Ser Gly
                    500                 505                 510

Tyr Leu Glu Asp Asn Gly Leu Lys Leu Val Glu Lys Glu Ala Tyr Ser
                    515                 520                 525

Asp Asp Val Pro Glu Gly Gln Val Val Lys Gln Lys Pro Ala Ala Gly
                    530                 535                 540

Thr Ala Val Lys Pro Gly Asn Glu Val Glu Val Thr Phe Ser Leu Gly
545                 550                 555                 560

Pro Glu Lys Lys Pro Ala Lys Thr Val Lys Glu Val Lys Ile Pro
                    565                 570                 575

Tyr Glu Pro Glu Asn Gly Asp Glu Leu Gln Val Gln Ile Ala Val
                    580                 585                 590

Asp Asp Ala Asp His Ser Ile Ser Asp Thr Tyr Glu Glu Phe Lys Ile
                    595                 600                 605

Lys Glu Pro Thr Glu Arg Thr Ile Glu Leu Lys Ile Glu Pro Gly Gln
                    610                 615                 620

Lys Gly Tyr Tyr Gln Val Met Val Asn Asn Lys Val Val Ser Tyr Lys
625                 630                 635                 640

Thr Ile Glu Tyr Pro Lys Asp Glu
                    645
```

<210> SEQ ID NO 2
<211> LENGTH: 79
<212> TYPE: DNA
<213> ORGANISM: Artificial Sequence
<220> FEATURE:
<223> OTHER INFORMATION: 5'-3' PCR primer

<400> SEQUENCE: 2
cagctaaacc attttcgag gtttaaatcc ttatcgttat gggtattgtt tgtaatatgc    60
tgatcggtaa acgtattag                                                79

<210> SEQ ID NO 3
<211> LENGTH: 59
<212> TYPE: DNA
<213> ORGANISM: Artificial Sequence
<220> FEATURE:
<223> OTHER INFORMATION: 5'-3' PCR primer

<400> SEQUENCE: 3
gcggcaaaac cccgccgaag cggggttttc ggcgttatta ttccagtttc agcagttcc    59

<210> SEQ ID NO 4
<211> LENGTH: 78
<212> TYPE: DNA
<213> ORGANISM: Artificial Sequence
<220> FEATURE:
<223> OTHER INFORMATION: 5'-3' PCR primer

<400> SEQUENCE: 4
cagctaaacc attttcgag gtttaaatcc ttatcgttat gggtattgtt tgtaatatgc    60
aatcagcctc ttctctgg                                                 78

<210> SEQ ID NO 5
<211> LENGTH: 57
<212> TYPE: DNA
<213> ORGANISM: Artificial Sequence
<220> FEATURE:
<223> OTHER INFORMATION: 5'-3' PCR primer

<400> SEQUENCE: 5
gcggcaaaac cccgccgaag cggggttttc ggcgttatca ttgtttgctg atacggc      57

<210> SEQ ID NO 6
<211> LENGTH: 62
<212> TYPE: DNA
<213> ORGANISM: Artificial Sequence
<220> FEATURE:
<223> OTHER INFORMATION: 5'-3' PCR primer

<400> SEQUENCE: 6
gattcgtttt actttcccgt tctctctgat tgtgaaattg cagctaaacc attttcgag    60 gt                                                                  62

<210> SEQ ID NO 7
<211> LENGTH: 55
<212> TYPE: DNA
<213> ORGANISM: Artificial Sequence
<220> FEATURE:
<223> OTHER INFORMATION: 5'-3' PCR primer

<400> SEQUENCE: 7
cttggaggct attacgatgt tggtaaaact caggaacaag gcggcaaaac cccgc        55

<210> SEQ ID NO 8
<211> LENGTH: 61
<212> TYPE: DNA
<213> ORGANISM: Artificial Sequence
<220> FEATURE:
<223> OTHER INFORMATION: 5'-3' PCR primer

<400> SEQUENCE: 8
cttgttcctg agttttacca acatcgtaat agcctccaag cagctaaacc attttcgag    60 g    61

<210> SEQ ID NO 9
<211> LENGTH: 54
<212> TYPE: DNA
<213> ORGANISM: Artificial Sequence
<220> FEATURE:
<223> OTHER INFORMATION: 5'-3' PCR primer

<400> SEQUENCE: 9
aggtcgactc tagaggatcc ccgggtaccg agctcgaatt gcggcaaaac cccg    54

<210> SEQ ID NO 10
<211> LENGTH: 30
<212> TYPE: DNA
<213> ORGANISM: Artificial Sequence
<220> FEATURE:
<223> OTHER INFORMATION: 5'-3' PCR primer

<400> SEQUENCE: 10
aagagctcca gctaaaccat ttttcgaggt    30

<210> SEQ ID NO 11
<211> LENGTH: 22
<212> TYPE: DNA
<213> ORGANISM: Artificial Sequence
<220> FEATURE:
<223> OTHER INFORMATION: 5'-3' PCR primer

<400> SEQUENCE: 11
aactgcaggc ggcaaaaccc cg    22

<210> SEQ ID NO 12
<211> LENGTH: 474
<212> TYPE: PRT
<213> ORGANISM: Artificial Sequence
<220> FEATURE:
<223> OTHER INFORMATION: prkC-FKBP12 fusion protein

<400> SEQUENCE: 12

Met Leu Ile Gly Lys Arg Ile Ser Gly Arg Tyr Gln Ile Leu Arg Val
 1               5                  10                  15

Ile Gly Gly Gly Gly Met Ala Asn Val Tyr Leu Ala Glu Asp Ile Ile
            20                  25                  30

Leu Asp Arg Glu Val Ala Ile Lys Ile Leu Arg Phe Asp Tyr Ala Asn
        35                  40                  45

Asp Asn Glu Phe Ile Arg Arg Phe Arg Arg Glu Ala Gln Ser Ala Ser
    50                  55                  60

Ser Leu Asp His Pro Asn Ile Val Ser Ile Tyr Asp Leu Gly Glu Glu
65                  70                  75                  80

Asp Asp Ile Tyr Tyr Ile Val Met Glu Tyr Val Glu Gly Met Thr Leu
                85                  90                  95

Lys Glu Tyr Ile Thr Ala Asn Gly Pro Leu His Pro Lys Glu Ala Leu

```
            100                 105                 110
Asn Ile Met Glu Gln Ile Val Ser Ala Ile Ala His Ala His Gln Asn
            115                 120                 125
Gln Ile Val His Arg Asp Ile Lys Pro His Asn Ile Leu Ile Asp His
            130                 135                 140
Met Gly Asn Ile Lys Val Thr Asp Phe Gly Ile Ala Thr Ala Leu Ser
145                 150                 155                 160
Ser Thr Thr Ile Thr His Thr Asn Ser Val Leu Gly Ser Val His Tyr
                        165                 170                 175
Leu Ser Pro Glu Gln Ala Arg Gly Gly Leu Ala Thr Lys Lys Ser Asp
                180                 185                 190
Ile Tyr Ala Leu Gly Ile Val Leu Phe Glu Leu Leu Thr Gly Arg Ile
            195                 200                 205
Pro Phe Asp Gly Glu Ser Ala Val Ser Ile Ala Leu Lys His Leu Gln
            210                 215                 220
Ala Glu Thr Pro Ser Ala Lys Arg Trp Asn Pro Ser Val Pro Gln Ser
225                 230                 235                 240
Val Glu Asn Ile Ile Leu Lys Ala Thr Ala Lys Asp Pro Phe His Arg
                        245                 250                 255
Tyr Glu Thr Ala Glu Asp Met Glu Ala Asp Ile Lys Thr Ala Phe Asp
                    260                 265                 270
Ala Asp Arg Leu Asn Glu Lys Arg Phe Thr Ile Gln Glu Asp Glu Glu
                275                 280                 285
Met Thr Lys Ala Ile Pro Ile Ile Lys Asp Glu Glu Leu Ala Lys Ala
            290                 295                 300
Ala Gly Glu Lys Glu Ala Glu Val Thr Thr Ala Gln Glu Asn Lys Thr
305                 310                 315                 320
Lys Lys Asn Gly Lys Arg Lys Lys Trp Pro Trp Val Leu Leu Thr Ile
                        325                 330                 335
Cys Leu Val Phe Ile Thr Ala Gly Ile Leu Ala Val Thr Val Phe Pro
                    340                 345                 350
Ser Leu Phe Met Ala Gly Gly Ser Glu Gly Gly Gly Ser Glu Met Gly
                355                 360                 365
Val Gln Val Glu Thr Ile Ser Pro Gly Asp Gly Arg Thr Phe Pro Lys
            370                 375                 380
Arg Gly Gln Thr Cys Val Val His Tyr Thr Gly Met Leu Glu Asp Gly
385                 390                 395                 400
Lys Lys Phe Asp Ser Ser Arg Asp Arg Asn Lys Pro Phe Lys Phe Thr
                        405                 410                 415
Leu Gly Lys Gln Glu Val Ile Arg Gly Trp Glu Glu Gly Val Ala Gln
                    420                 425                 430
Met Ser Val Gly Gln Arg Ala Lys Leu Ile Ile Ser Ser Asp Tyr Ala
                435                 440                 445
Tyr Gly Ala Thr Gly His Pro Gly Ile Ile Pro Pro His Ala Thr Leu
            450                 455                 460
Val Phe Asp Val Glu Leu Leu Lys Leu Glu
465                 470

<210> SEQ ID NO 13
<211> LENGTH: 592
<212> TYPE: PRT
<213> ORGANISM: Artificial Sequence
<220> FEATURE:
<223> OTHER INFORMATION: prkC-EPOR fusion protein
```

<400> SEQUENCE: 13

```
Met Leu Ile Gly Lys Arg Ile Ser Gly Arg Tyr Gln Ile Leu Arg Val
1               5                   10                  15

Ile Gly Gly Gly Met Ala Asn Val Tyr Leu Ala Glu Asp Ile Ile
            20                  25                  30

Leu Asp Arg Glu Val Ala Ile Lys Ile Leu Arg Phe Asp Tyr Ala Asn
        35                  40                  45

Asp Asn Glu Phe Ile Arg Arg Phe Arg Glu Ala Gln Ser Ala Ser
    50                  55                  60

Ser Leu Asp His Pro Asn Ile Val Ser Ile Tyr Asp Leu Gly Glu Glu
65                  70                  75                  80

Asp Asp Ile Tyr Tyr Ile Val Met Glu Tyr Val Gly Met Thr Leu
                85                  90                  95

Lys Glu Tyr Ile Thr Ala Asn Gly Pro Leu His Pro Lys Glu Ala Leu
                100                 105                 110

Asn Ile Met Glu Gln Ile Val Ser Ala Ile Ala His Ala His Gln Asn
            115                 120                 125

Gln Ile Val His Arg Asp Ile Lys Pro His Asn Ile Leu Ile Asp His
    130                 135                 140

Met Gly Asn Ile Lys Val Thr Asp Phe Gly Ile Ala Thr Ala Leu Ser
145                 150                 155                 160

Ser Thr Thr Ile Thr His Thr Asn Ser Val Leu Gly Ser Val His Tyr
                165                 170                 175

Leu Ser Pro Glu Gln Ala Arg Gly Gly Leu Ala Thr Lys Lys Ser Asp
                180                 185                 190

Ile Tyr Ala Leu Gly Ile Val Leu Phe Glu Leu Leu Thr Gly Arg Ile
            195                 200                 205

Pro Phe Asp Gly Glu Ser Ala Val Ser Ile Ala Leu Lys His Leu Gln
        210                 215                 220

Ala Glu Thr Pro Ser Ala Lys Arg Trp Asn Pro Ser Val Pro Gln Ser
225                 230                 235                 240

Val Glu Asn Ile Ile Leu Lys Ala Thr Ala Lys Asp Pro Phe His Arg
                245                 250                 255

Tyr Glu Thr Ala Glu Asp Met Glu Ala Asp Ile Lys Thr Ala Phe Asp
                260                 265                 270

Ala Asp Arg Leu Asn Glu Lys Arg Phe Thr Ile Gln Glu Asp Glu Glu
            275                 280                 285

Met Thr Lys Ala Ile Pro Ile Ile Lys Asp Glu Glu Leu Ala Lys Ala
        290                 295                 300

Ala Gly Glu Lys Glu Ala Glu Val Thr Thr Ala Gln Glu Asn Lys Thr
305                 310                 315                 320

Lys Lys Asn Gly Lys Arg Lys Lys Trp Pro Trp Val Leu Leu Thr Ile
                325                 330                 335

Cys Leu Val Phe Ile Thr Ala Gly Ile Leu Ala Val Thr Val Phe Pro
                340                 345                 350

Ser Leu Phe Met Ala Gly Gly Ser Glu Gly Gly Ser Glu Ala Pro
        355                 360                 365

Pro Pro Asn Leu Pro Asp Pro Lys Phe Glu Ser Lys Ala Ala Leu Leu
370                 375                 380

Ala Ala Arg Gly Pro Glu Glu Leu Leu Cys Phe Thr Glu Arg Leu Glu
385                 390                 395                 400

Asp Leu Val Cys Phe Trp Glu Glu Ala Ala Ser Ala Gly Val Gly Pro
                405                 410                 415
```

```
Gly Asn Tyr Ser Phe Ser Tyr Gln Leu Glu Asp Glu Pro Trp Lys Leu
            420                 425                 430

Cys Arg Leu His Gln Ala Pro Thr Ala Arg Gly Ala Val Arg Phe Trp
            435                 440                 445

Cys Ser Leu Pro Thr Ala Asp Thr Ser Ser Phe Val Pro Leu Glu Leu
            450                 455                 460

Arg Val Thr Ala Ala Ser Gly Ala Pro Arg Tyr His Arg Val Ile His
465                 470                 475                 480

Ile Asn Glu Val Val Leu Leu Asp Ala Pro Val Gly Leu Val Ala Arg
                485                 490                 495

Leu Ala Asp Glu Ser Gly His Val Val Leu Arg Trp Leu Pro Pro Pro
            500                 505                 510

Glu Thr Pro Met Thr Ser His Ile Arg Tyr Glu Val Asp Val Ser Ala
            515                 520                 525

Gly Asn Gly Ala Gly Ser Val Gln Arg Val Glu Ile Leu Glu Gly Arg
            530                 535                 540

Thr Glu Cys Val Leu Ser Asn Leu Arg Gly Arg Thr Arg Tyr Thr Phe
545                 550                 555                 560

Ala Val Arg Ala Arg Met Ala Glu Pro Ser Phe Gly Gly Phe Trp Ser
                565                 570                 575

Ala Trp Ser Glu Pro Val Ser Leu Leu Thr Pro Ser Asp Leu Asp Pro
            580                 585                 590

<210> SEQ ID NO 14
<211> LENGTH: 495
<212> TYPE: PRT
<213> ORGANISM: Artificial Sequence
<220> FEATURE:
<223> OTHER INFORMATION: prkC-streptavidin fusion protein

<400> SEQUENCE: 14

Met Leu Ile Gly Lys Arg Ile Ser Gly Arg Tyr Gln Ile Leu Arg Val
1               5                   10                  15

Ile Gly Gly Gly Gly Met Ala Asn Val Tyr Leu Ala Glu Asp Ile Ile
            20                  25                  30

Leu Asp Arg Glu Val Ala Ile Lys Ile Leu Arg Phe Asp Tyr Ala Asn
            35                  40                  45

Asp Asn Glu Phe Ile Arg Arg Phe Arg Arg Glu Ala Gln Ser Ala Ser
        50                  55                  60

Ser Leu Asp His Pro Asn Ile Val Ser Ile Tyr Asp Leu Gly Glu Glu
65                  70                  75                  80

Asp Asp Ile Tyr Tyr Ile Val Met Glu Tyr Val Glu Gly Met Thr Leu
                85                  90                  95

Lys Glu Tyr Ile Thr Ala Asn Gly Pro Leu His Pro Lys Glu Ala Leu
            100                 105                 110

Asn Ile Met Glu Gln Ile Val Ser Ala Ile Ala His Ala His Gln Asn
            115                 120                 125

Gln Ile Val His Arg Asp Ile Lys Pro His Asn Ile Leu Ile Asp His
        130                 135                 140

Met Gly Asn Ile Lys Val Thr Asp Phe Gly Ile Ala Thr Ala Leu Ser
145                 150                 155                 160

Ser Thr Thr Ile Thr His Thr Asn Ser Val Leu Gly Ser Val His Tyr
                165                 170                 175

Leu Ser Pro Glu Gln Ala Arg Gly Gly Leu Ala Thr Lys Lys Ser Asp
            180                 185                 190
```

Ile Tyr Ala Leu Gly Ile Val Leu Phe Glu Leu Leu Thr Gly Arg Ile
        195                 200                 205

Pro Phe Asp Gly Glu Ser Ala Val Ser Ile Ala Leu Lys His Leu Gln
210                 215                 220

Ala Glu Thr Pro Ser Ala Lys Arg Trp Asn Pro Ser Val Pro Gln Ser
225                 230                 235                 240

Val Glu Asn Ile Ile Leu Lys Ala Thr Ala Lys Asp Pro Phe His Arg
                245                 250                 255

Tyr Glu Thr Ala Glu Asp Met Glu Ala Asp Ile Lys Thr Ala Phe Asp
                260                 265                 270

Ala Asp Arg Leu Asn Glu Lys Arg Phe Thr Ile Gln Glu Asp Glu Glu
                275                 280                 285

Met Thr Lys Ala Ile Pro Ile Ile Lys Asp Glu Glu Leu Ala Lys Ala
                290                 295                 300

Ala Gly Glu Lys Glu Ala Glu Val Thr Thr Ala Gln Glu Asn Lys Thr
305                 310                 315                 320

Lys Lys Asn Gly Lys Arg Lys Lys Trp Pro Trp Val Leu Leu Thr Ile
                325                 330                 335

Cys Leu Val Phe Ile Thr Ala Gly Ile Leu Ala Val Thr Val Phe Pro
                340                 345                 350

Ser Leu Phe Met Ala Gly Gly Ser Glu Gly Gly Gly Ser Glu Met Ala
                355                 360                 365

Glu Ala Gly Ile Thr Gly Thr Trp Tyr Asn Gln Leu Gly Ser Thr Phe
                370                 375                 380

Ile Val Thr Ala Gly Ala Asp Gly Ala Leu Thr Gly Thr Tyr Glu Ser
385                 390                 395                 400

Ala Val Gly Asn Ala Glu Ser Arg Tyr Thr Leu Thr Gly Arg Tyr Asp
                405                 410                 415

Ser Ala Pro Ala Thr Asp Gly Ser Gly Thr Ala Leu Gly Trp Arg Val
                420                 425                 430

Ala Trp Lys Asn Asn Tyr Arg Asn Ala His Ser Ala Thr Thr Trp Ser
                435                 440                 445

Gly Gln Tyr Val Gly Gly Ala Glu Ala Arg Ile Asn Thr Gln Trp Thr
                450                 455                 460

Leu Thr Ser Gly Thr Thr Glu Ala Asn Ala Trp Lys Ser Thr Leu Arg
465                 470                 475                 480

Gly His Asp Thr Phe Thr Lys Val Lys Pro Ser Ala Ala Ser Ile
                485                 490                 495

<210> SEQ ID NO 15
<211> LENGTH: 10
<212> TYPE: DNA
<213> ORGANISM: Staphylococcus aureus
<220> FEATURE:
<221> NAME/KEY: misc_feature
<222> LOCATION: 1
<223> OTHER INFORMATION: biotinylated thymine

<400> SEQUENCE: 15
ttccagatta                                                                10

<210> SEQ ID NO 16
<211> LENGTH: 11
<212> TYPE: DNA
<213> ORGANISM: Staphylococcus aureus
<220> FEATURE:
<221> NAME/KEY: misc_feature

```
<222> LOCATION: 11
<223> OTHER INFORMATION: biotinylated adenine

<400> SEQUENCE: 16
caacttcacc a                                                          11

<210> SEQ ID NO 17
<211> LENGTH: 21
<212> TYPE: DNA
<213> ORGANISM: Artificial Sequence
<220> FEATURE:
<223> OTHER INFORMATION: mecA target 'bridging' oligonucleotide

<400> SEQUENCE: 17
tggtgaagtt gtaatctgga a                                               21

<210> SEQ ID NO 18
<211> LENGTH: 10
<212> TYPE: DNA
<213> ORGANISM: Artificial Sequence
<220> FEATURE:
<223> OTHER INFORMATION: biotinylated oligonucleotide
<220> FEATURE:
<221> NAME/KEY: misc_feature
<222> LOCATION: 1
<223> OTHER INFORMATION: biotinylated adenine

<400> SEQUENCE: 18
ataaacacct                                                            10

<210> SEQ ID NO 19
<211> LENGTH: 10
<212> TYPE: DNA
<213> ORGANISM: Artificial Sequence
<220> FEATURE:
<223> OTHER INFORMATION: biotinylated oligonucleotide
<220> FEATURE:
<221> NAME/KEY: misc_feature
<222> LOCATION: 10
<223> OTHER INFORMATION: biotinylated cytosine

<400> SEQUENCE: 19
ccaattcatc                                                            10

<210> SEQ ID NO 20
<211> LENGTH: 22
<212> TYPE: DNA
<213> ORGANISM: Artificial Sequence
<220> FEATURE:
<223> OTHER INFORMATION: miR-143 oligonucleotide

<400> SEQUENCE: 20
tgagatgaag cactgtagct ca                                              22

<210> SEQ ID NO 21
<211> LENGTH: 42
<212> TYPE: DNA
<213> ORGANISM: Artificial Sequence
<220> FEATURE:
<223> OTHER INFORMATION: 'R-out' oligonucleotide

<400> SEQUENCE: 21
gatgaattgg aggtgtttat agcggacccc tactgagttg tg                        42

<210> SEQ ID NO 22
<211> LENGTH: 6
<212> TYPE: DNA
```

```
<213> ORGANISM: Artificial Sequence
<220> FEATURE:
<223> OTHER INFORMATION: target nucleic acid sequence

<400> SEQUENCE: 22 tgccaa                                                                      6

<210> SEQ ID NO 23
<211> LENGTH: 10
<212> TYPE: DNA
<213> ORGANISM: Artificial Sequence
<220> FEATURE:
<223> OTHER INFORMATION: biotinylated oligonucleotide
<220> FEATURE:
<221> NAME/KEY: misc_feature
<222> LOCATION: 1
<223> OTHER INFORMATION: biotinylated guanine

<400> SEQUENCE: 23
gtgacaggga                                                                 10

<210> SEQ ID NO 24
<211> LENGTH: 10
<212> TYPE: DNA
<213> ORGANISM: Artificial Sequence
<220> FEATURE:
<223> OTHER INFORMATION: biotinylated oligonucleotide
<220> FEATURE:
<221> NAME/KEY: misc_feature
<222> LOCATION: 10
<223> OTHER INFORMATION: biotinylated cytosine

<400> SEQUENCE: 24
ataaagaggc                                                                 10

<210> SEQ ID NO 25
<211> LENGTH: 20
<212> TYPE: DNA
<213> ORGANISM: Artificial Sequence
<220> FEATURE:
<223> OTHER INFORMATION: target nucleic acid sequence

<400> SEQUENCE: 25
cactgtccct tatttctccg                                                      20

<210> SEQ ID NO 26
<211> LENGTH: 10
<212> TYPE: DNA
<213> ORGANISM: Artificial Sequence
<220> FEATURE:
<223> OTHER INFORMATION: quencher oligonucleotide
<220> FEATURE:
<221> NAME/KEY: misc_feature
<222> LOCATION: 1
<223> OTHER INFORMATION: adenine attached to 'quencher'

<400> SEQUENCE: 26
agtcgttcag                                                                 10

<210> SEQ ID NO 27
<211> LENGTH: 35
<212> TYPE: DNA
<213> ORGANISM: Artificial Sequence
<220> FEATURE:
<223> OTHER INFORMATION: fluorophore oligonucleotide
<220> FEATURE:
<221> NAME/KEY: misc_feature
<222> LOCATION: 1
<223> OTHER INFORMATION: thymine attached to 'fluorophore'
```

```
<400> SEQUENCE: 27
tcagcaagtc cgtggtaggg caggttgggg tgact                              35
```

BACTERIAL METHODS

SEQUENCE LISTING

Sequence listing information is provided below and a computer readable form of the sequence listing information is included, which is incorporated by reference. Applicants hereby state that the information recorded in computer readable form is identical to the written (on paper) sequence listing.

The invention generally relates to the manipulation of bacterial spore germination, and more specifically to the modification of germination receptors to increase the range of agents that can act as germinants. The invention further relates to the uses of modified bacterial spores which have been engineered to germinate in response to novel germinants.

Spore-forming bacteria, such as Bacilli and Clostridia, share the characteristic of forming metabolically inactive endospores. Spores are highly resistant to adverse environmental conditions including heat, and their ubiquitous presence in nature makes them inevitable contaminants of foods and food ingredients. Spores can germinate under favourable conditions, and the following outgrowth can lead to food spoilage and food-borne illness. Germination of spores has been best studied in *Bacillus* species, but the process of spore germination is less well understood in anaerobic Clostridia. Further details of bacterial spore structure and chemical sporicidal agents are described by Russell (1990) *Clin. Microbiol. Rev.* 3(2): 99-119.

The survival and persistence of spore-forming bacteria, such as *Bacillus* and *Clostridium* species, largely depends on their ability to produce endospores under conditions that are unfavourable for growth, whereas their pathogenicity resides in the fact that the spores can germinate under favourable conditions. The very first stage of the germination process involves sensing specific compounds, named germinants, or can be due to physical factors. Subsequent events required for full germination include the hydrolysis of the cortex peptidoglycan, rehydration of the core, and resumption of metabolic activity and the degradation of small acid-soluble proteins (SASPs) by germination protease GPR.

As explained in the Introduction to the article by Xiao et al (Xiao, Y., et al "Clostridial spore germination versus bacilli: Genome mining and current insights", *Food Microbiology* (2011), 28(2): 266-274), the process of spore germination is irreversible and eventually results in a complete and viable vegetative bacterial cell. The first detectable events of germination are the release of $Zn^{2+}$, $K^{2+}$, $Na^+$, dipicolinic acid and $Ca^{2+}$ (Ca-DPA) and a rise in spore internal pH. Potassium ions are subsequently reabsorbed by an energy-dependent process. The initial events are accompanied by a loss of spore heat resistance and dormancy, and can be recognized microscopically by the transition from phase bright to phase dark. Nutritional inducers of germination include L-alanine and a combination of L-asparagine, D-glucose, D-fructose, $K^+$ (AGFK) for *Bacillus subtilis*, and L-alanine and inosine for *B. cereus*. Non-nutritional germinants include chemicals such as dodecylamide and Ca-DPA. Also, peptidoglycan fragments have recently been shown to induce germination (Shah et al. (2008). *Cell.* 135(3): 486-496). Other non-nutritional physical factors that can trigger germination include high hydrostatic pressure (HHP), heat, abrasion and ageing. Spore germination in Clostridia often involves a combination of nutrient germinants and generally proceeds more slowly than in *Bacillus* species.

Similar to germination in Bacilli, non-proteolytic *Clostridium botulinum* spores can germinate in response to L-alanine and various other amino acids and nutrients such as sugars, lactate and nicotinamide. For *C. perfringens* spores it has been established that the following compounds can trigger germination: L-asparagine, KCl, a mixture of L-asparagine and KCl, Ca-DPA and a mixture of $Na^+$ and inorganic phosphate (NaPi). The cholate derivatives and the amino acid glycine in bile act as cogerminants of *Clostridium difficile* spores. *Clostridium tetani* spore germination has been reported to be triggered by a mixture of methionine, lactate, nicotinamide and $Na^+$ in phosphate buffer At a molecular level the process of spore germination is better understood in *Bacillus* species than in their anaerobic relatives, thanks to decennia of research on model organisms such as *B. subtilis* and *B. cereus*, which are genetically accessible and for which whole genome sequences are available. Indeed, *B. subtilis* was amongst the first of the bacterial genomes sequences to be completed. In the last few years, the complete genomes of a number of *Clostridium* species have been sequenced and annotated, enabling comparisons of genes involved in spore germination of *Bacillus* and *Clostridium* using comparative genomics approaches. Xiao et al analysed the occurrence of known and putative *Bacillus* germination-related genes in *Clostridium* species, and in a representative number of *Bacillus* species, and discussed the presence of genes involved in germination. Nevertheless, even this very recent review of bacterial germination does not consider the possibility of engineering the genes involved in germination to modify the range of molecules that can act as germinants, as disclosed in the present invention.

Shah et al., (2008) and PCT publication WO/2009/042956 (patent application no. PCT/US2008/078004; Dworkin) disclose that bacterial cell wall peptidoglycan fragments can induce germination of bacterial spores, and identified that this effect is via the prkC receptor. Neither document discloses or contemplates the possibility of engineering the prkC gene or protein to modify the range of molecules that can act as germinants, as disclosed in the present invention.

U.S. Pat. No. 5,614,375 (Citri) discloses the use of spore germination as a sensor to test for biotoxic contaminants. The spores were induced to germinate using a known germinant in the presence of a test sample, and the level of enzyme activity expressed by the bacteria after germination was inversely proportional to the level of toxicity. This patent does not contemplate the possibility of engineering the bacteria to modify the range of molecules that can act as germinants, as disclosed in the present invention.

U.S. Pat. No. 5,795,730 (Tautvydas) discloses the use of spore germination as an indicator of sterilisation efficiency. This patent does not contemplate the possibility of engineering the bacteria to modify the range of molecules that can act as germinants, as disclosed in the present invention.

U.S. Pat. No. 6,872,539 (Rotman) also discloses the use of spore germination as an indicator of the presence of target analytes. The patent uses precursors of known germinants to induce germination in the presence of an analyte capable of converting the precursor to the active form of the germinant. Although the patent discloses modifying the bacteria to improve ease of signal detection during germination, it does not contemplate the possibility of engineering the bacteria to modify the range of molecules that can act as germinants, as disclosed in the present invention.

Bacterial cells have been engineered for use as live biosensors, for example in bioremediation of contaminated environments, and as bioproduct delivery vehicles in medical and agricultural applications. However, there are significant difficulties in dealing with live cells, as it is necessary to provide the bacteria with nutrients and favourable conditions (in the case of biosensors) or tightly control cell division and growth (in the case of bioproduct delivery inside animals or humans).

Spores are ideal candidates for various applications in biotechnology and the growing field of synthetic biology. Spores can be stored desiccated at room temperature and can withstand harsh environmental conditions if used in demanding applications. However, the lack of control over when and where spores germinate has meant that their use as a chassis for engineered cellular function has not been explored.

The inventors have now developed a method of engineering programmable, ligand-responsive bacterial spore germination by manipulation of bacterial germination receptors. Essentially, this invention will allow the use of bacterial spores as engineered genetic devices that are activated precisely when and where they are needed.

More specifically, as described in Example 1, the inventors have shown that it is possible to make bacterial spores that germinate in response to rapamycin; in Example 2 the inventors have made bacterial spores that germinate in response to erythropoietin; in Example 3 the inventors have made bacterial spores that germinate in response to DNA; in Example 4 the inventors have shown how to make a biosensor of MRSA using modified bacterial spores; in Example 5 the inventors have made bacterial spores that germinate in response to the amplified output of a DNA logic-gate circuit; in Example 6 the inventors have used click-chemistry to make bacterial spores that germinate in the presence of copper; in Example 7 the inventors have made bacterial spores that germinate in response to platelet derived growth factor (PDGF); and in Example 8 the inventors have made bacterial spores that germinate in response to thrombin.

Accordingly, a first aspect of the invention provides a bacterial spore which has been modified such that the spore undergoes germination in the presence of a germinant which does not stimulate germination of an equivalent unmodified bacterial spore.

This aspect of the invention includes a bacterial spore which has been modified such that the spore undergoes germination, in the presence of a germinant, at a level at least 10× greater than an otherwise equivalent unmodified bacterial spore in the presence of that germinant. Preferably the modified spore undergoes germination, in the presence of a germinant, at a level at least 20×, or at least 30×, or at least 40×, or at least 50× greater than an otherwise equivalent unmodified bacterial spore in the presence of that germinant. More preferably, the modified spore undergoes germination, in the presence of a germinant, at a level at least 100×, or at least 500×, or at least 1000× greater than an otherwise equivalent unmodified bacterial spore in the presence of that germinant. Most preferably, the presence of the germinant does not cause the otherwise equivalent unmodified bacterial spore to undergo germination at above basal level, or it only does so at an undetectable level.

Suitable conditions and methodology for inducing germination in the presence of a germinant, for detecting germination, and for measuring germination efficiency are very well known in the art, and are discussed in more detail below.

In this document, reference to a single bacterial spore ('a bacterial spore') also includes a multiplicity of generally identical bacterial spores and should be interpreted accordingly, except where the context demands the meaning of a single individual spore.

The inventors have shown that modifying the prkC protein of a bacterial spore can result in spores that germinate in response to defined stimuli. Thus, the invention includes a bacterial spore comprising a modified prkC protein, wherein the prkC protein has been modified such that the spore undergoes germination in the presence of a germinant which does not stimulate germination of a bacterial spore comprising wild-type prkC protein.

This aspect of the invention includes a bacterial spore whose prkC protein has been modified such that the spore undergoes germination, in the presence of a germinant, at a level at least 10× greater than an otherwise equivalent bacterial spore with a wild-type (i.e., unmodified) prkC protein in the presence of that germinant. Preferably the modified spore undergoes germination, in the presence of a germinant, at a level at least 20×, or at least 30×, or at least 40×, or at least 50× greater than the otherwise equivalent unmodified bacterial spore in the presence of that germinant. More preferably, the modified spore undergoes germination, in the presence of a germinant, at a level at least 100×, or at least 500×, or at least 1000× greater than the otherwise equivalent unmodified bacterial spore in the presence of that germinant. Most preferably, the presence of the germinant does not cause the otherwise equivalent bacterial spore with an unmodified, i.e. wild-type, prkC protein to undergo germination at above basal level, or it only does so at an undetectable level.

PrkC is a serine/threonine protein kinase (EC 2.7.11.1), that has been shown to be responsible, in *B. subtilis*, for muropeptides-induced spore germination (Shah et al., 2008 and PCT publication WO/2009/042956 (PCT/US2008/078004)).

The sequence of the prkC protein of *Bacillus subtilis* str. 168 can be found under Genbank Accession No. NP_389459, 'live' version dated 22 Oct. 2010 10:37 am, (Barbe et al (2009) *Microbiology* (Reading, Engl.) 155(6), 1758-1775; Kunst et al (1997), *Nature* 390, 249-256). It is a 648 amino acid protein having PKc-like domains, ATP binding sites, catalytic domains, substrate binding sites, activation loops, PASTA domains, as specified in NP_389459. The sequence of the prkC protein of *Bacillus subtilis* str. 168 according to NP_389459 is as follows:

```
                                              (SEQ ID NO: 1)
  1   MLIGKRISGR  YQILRVIGGG  GMANVYLAED  IILDREVAIK
      ILRFDYANDN  EFIRRFRREA

61   QSASSLDHPN  IVSIYDLGEE  DDIYYIVMEY  VEGMTLKEYI
      TANGPLHPKE  ALNIMEQIVS

121   AIAHAHQNQI  VHRDIKPHNI  LIDHMGNIKV  TDFGIATALS
      STTITHTNSV  LGSVHYLSPE

181   QARGGLATKK  SDIYALGIVL  FELLTGRIPF  DGESAVSIAL
      KHLQAETPSA  KRWNPSVPQS

241   VENIILKATA  KDPFHRYETA  EDMEADIKTA  FDADRLNEKR
      FTIQEDEEMT  KAIPIIKDEE

301   LAKAAGEKEA  EVTTAQENKT  KKNGKRKKWP  WVLLTICLVF
      ITAGILAVTV  FPSLFMPKDV

361   KIPDVSGMEY  EKAAGLLEKE  GLQVDSEVLE  ISDEKIEEGL
      MVKTDPKADT  TVKEGATVTL

421   YKSTGKAKTE  IGDVTGQTVD  QAKKALKDQG  FNHVTVNEVN
      DEKNAGTVID  QNPSAGTELV

481   PSEDQVKLTV  SIGPEDITLR  DLKTYSKEAA  SGYLEDNGLK
      LVEKEAYSDD  VPEGQVVKQK

541   PAAGTAVKPG  NEVEVTFSLG  PEKKPAKTVK  EKVKIPYEPE
      NEGDELQVQI  AVDDADHSIS

601   DTYEEFKIKE  PTERTIELKI  EPGQKGYYQV  MVNNKVVSYK
      TIEYPKDE.
```

The sequence of the prkC protein of *Bacillus subtilis* subsp. *natto* BEST195 can be found under Genbank Accession No. BAI85204 (version dated 1 Sep. 2010). The sequence of the prkC protein of *Bacillus subtilis* subsp. *spizizenii* str. W23 can be found under Genbank Accession No. YP_003865980 (version dated 1 Sep. 2010). The entire disclosures of the Genbank entries relating to prkC are incorporated herein by reference.

The sequence of the prkC gene and encoded prkC protein from a range of other spore-forming bacteria is known in the art. For example, as shown in table 2 of Xiao et al (2010), prkC from *B. subtilis, B. anthracis, B. cereus, B. clausii, B. halodurans, B. licheniformis, B. thuringiensis, B. weihenstephanensis, C. acetobutylicum, C. beijerinckii, C. botulinum, C. cellulolyticum, C. difficile, C. kluyveri, C. novyi, C. perfringens, C. phytofermentans, C. tetani, C. thermocellum* and *A. oremlandii* are known in the art, including prkC from three distinct strains of *B. anthracis, B. cereus* and *C. perfringens*, two distinct strains of *C. kluyveri*, and ten distinct strains of *C. botulinum*.

According to Xiao et al (2010), prkC was found to be highly conserved in the genomes of Bacilli and Clostridia, although the prkC gene of *C. perfringens* was found to contain one additional PASTA repeat compared to the *B. subtilis* homologue.

A search on the NCBI database identified 136 entries for *Bacillus* prkC nucleotide sequences, and 82 entries for *Bacillus* prkC protein sequences. Thus the skilled person can readily identify the prkC from a range of spore-forming bacteria.

The inventors have further shown that shown that modifying the extracellular domain of the prkC protein, while keeping the intracellular (signalling) domain and the transmembrane domain unchanged, on a bacterial spore can result in spores that germinate in response to defined stimuli. Thus, the invention includes a bacterial spore comprising a modified prkC protein, wherein the extracellular domain of the modified prkC protein binds an agent which is not bound by the extracellular domain of the wild-type prkC protein, and wherein the agent is a germinant that stimulates germination of the bacterial spore.

In one preferred embodiment, the prkC protein is modified by replacing the native prkC extracellular domain with a binding moiety that binds directly to the desired agent, typically an agent that is not bound by the native, unmodified, extracellular domain of the prkC protein. Alternatively, but less preferred, some or all of the native prkC receptor extracellular domain may be present on the modified protein, together with the binding moiety that binds to the desired agent.

In one embodiment, the binding moiety is a polypeptide moiety. For example, in Example 1 the native prkC extracellular domain has been replaced by the extracellular domain of the FKBP12, and in Example 2 the native prkC extracellular domain has been replaced by the extracellular domain of the erythropoietin receptor. These modified prkC receptors bind to the agents rapamycin and erythropoietin, respectively, which agents thus act as germinants that stimulate germination of the bacterial spore. As another example, the polypeptide binding moiety may be the antigen binding domain of an antibody.

In other embodiments, the binding moiety may be a non-polypeptide moiety, such as a sugar, which can, for example, be attached to prkC proteins on a bacterial spore using glycosyl transferases, and which can bind directly to a variety of known saccharide-binding agents.

In another preferred embodiment, the prkC protein is modified by replacing the native prkC extracellular domain with a moiety that binds indirectly, via an intermediate binding agent, to the desired agent, typically an agent that is not bound by the unmodified extracellular domain of the prkC protein. Alternatively, but less preferred, some or all of the native prkC receptor extracellular domain may be present on the modified protein, together with the moiety that indirectly binds to the desired agent via an intermediate binding agent.

In this embodiment, suitable moieties that bind indirectly to the desired agent include a biotin binding region of streptavidin. For example, as described in Examples 3-5 and 7-8, the native prkC extracellular domain has been replaced by a biotin binding region of streptavidin (Stayton et al (1999) "Streptavidin-biotin binding energetics". *Biomol Eng* 16: 39-44). The streptavidin binds with high affinity to an intermediate binding agent, such as biotin or a biotin analogue, which has been conjugated to a further molecule that, in turn, binds to the desired agent. In this embodiment, it is preferred that both the intermediate binding agent and the desired agent do not bind to the native, unmodified, extracellular domain of the prkC protein. It is appreciated that the biotin binding region of streptavidin can include variants having an altered affinity for biotin or a biotin analogue such as desthiobiotin (Levy & Ellington (2008) *Chem Biol.* 15(9): 979-989; Aslan et al (2005) "Engineered single-chain dimeric streptavidins with an unexpected strong preference for biotin-4-fluorescein". *Proc Natl Acad Sci USA.* 102: 8507-8512; Qureshi et al (2001) "Development and characterization of a series of soluble tetrameric and monomeric streptavidin muteins with differential biotin binding affinities". *J Biol Chem.* 276: 46422-46428; Reznik et al (1998) "A streptavidin mutant with altered ligand-binding specificity". *Proc Natl Acad Sci USA.* 95:13525-13530). Suitable alternatives to biotin as a ligand for avidin and streptavidin include 9-methyl biotins (Dixon et al (2002) "Theoretical and experimental studies of biotin analogues that bind almost as tightly to streptavidin as biotin". *J Org Chem.* 67: 1827-1837). Accordingly, other suitable binding pairs that allow for indirect binding to the desired agent include, for example, avidin:biotin, neutravidin:biotin, streptavidin:desthiobiotin, avidin:desthiobiotin and neutravidin:desthiobiotin. In these embodiments, the extracellular domain of the prkC protein is modified to comprise or consist of a region or variant of avidin, neutravidin or streptavidin that binds to biotin or a biotin analogue, and the biotin or analogue (e.g., desthiobiotin)—acting as intermediate binding agents—are conjugated to a further molecule that, in turn, binds to the desired germination agent.

Typically, the modified extracellular domain of the prkC protein binds the agent (whether directly or indirectly) at a level at least 10× greater than does the extracellular domain of the native, i.e, unmodified, prkC protein. Preferably, the modified extracellular domain of the prkC protein binds the agent at a level at least 20×, or at least 30×, or at least 40×, or at least 50× greater, or more preferably at a level at least 100×, or at least 500×, or at least 1000× greater, than does the unmodified extracellular domain of the prkC protein. Most preferably, the unmodified extracellular domain of the prkC protein does not bind the agent, or it only does so at an undetectable level.

In another preferred embodiment, the prkC protein is modified in a way that causes the modified prkC to dimerise in the presence of the desired agent—without necessarily binding or remaining bound to the desired agent. For example, as described in Example 6, the native prkC extracellular domain has been replaced by a biotin binding region of streptavidin, which in turn is bound with either biotinylated alkyne or biotinylated azide. In the presence of the desired agent, in this example copper, the two moieties are brought together, resulting in dimerisation of the prkC, and subsequent germination of the spore.

Typically, the spore with the modified prkC extracellular domain germinates, in the presence of the agent, at a level at least 10× greater than does an otherwise equivalent spore with a wild-type, i.e., unmodified, prkC extracellular domain. Preferably, the spore with the modified prkC extracellular domain germinates, in the presence of the agent, at a level at least 20×, or at least 30×, or at least 40×, or at least 50× greater, or more preferably at a level at least 100×, or at least 500×, or at least 1000× greater, than does an otherwise equivalent spore with an unmodified prkC extracellular domain. Most preferably, the otherwise equivalent spore with the unmodified prkC extracellular domain, in the presence of the agent, does not undergo germination at above basal level, or it only does so at an undetectable level.

In an embodiment, the spore may have been engineered to express two, or more, modified prkC germination receptors with different extracellular domains that recognise and stimulate germination in the presence of different agents.

It is appreciated that the modified prkC protein may be exogenously added, i.e. the bacteria from which the spore is formed has been genetically manipulated to express the modified prkC protein on the spore generated therefrom. Accordingly, it may be preferred that the native prkC protein in the bacteria is not expressed on the bacterial spore. Thus, in an embodiment, the modified bacterial spore may have the 'native' or 'wild-type' prkC gene inactivated, knocked-out, knocked-down, or deleted such that the 'native' or 'wild-type' prkC protein is either not expressed or is non-functional or is expressed at a level at least 10× lower than the modified prkC protein. More preferably, the 'native' or 'wild-type' prkC protein is expressed at a level at least 20×, or at least 30×, or at least 40×, or at least 50× lower, or still more preferably at least 100×, or at least 500×, or at least 1000× lower, than the modified prkC protein.

As an alternative to prkC, the gerA receptor may be modified to affect germinant recognition. The Ger receptor family from sporulating bacteria is described by Ross & Abel-Santos (2010) *Curr. Issues Mol. Biol.* 12: 147-158.

Accordingly, another aspect of the invention provides a bacterial spore comprising a modified gerA protein, wherein the gerA protein has been modified such that the spore undergoes germination in the presence of a germinant which does not stimulate germination of a bacterial spore comprising wild-type gerA protein.

This aspect of the invention includes a bacterial spore whose gerA protein has been modified such that the spore undergoes germination, in the presence of a germinant, at a level at least 10× greater than an otherwise equivalent bacterial spore with a wild-type, i.e. unmodified, gerA protein in the presence of that germinant. Preferably the modified spore undergoes germination, in the presence of a germinant, at a level at least 20×, or at least 30×, or at least 40×, or at least 50× greater than the otherwise equivalent unmodified bacterial spore in the presence of that germinant. More preferably, the modified spore undergoes germination, in the presence of a germinant, at a level at least 100×, or at least 500×, or at least 1000× greater than the otherwise equivalent unmodified bacterial spore in the presence of that germinant. Most preferably, the presence of the germinant does not cause the otherwise equivalent unmodified bacterial spore with a wild-type gerA protein to undergo germination at above basal level, or it only does so at an undetectable level.

As described by Hudson et al (2001, *J. Bacteriol.* 183(14): 4317-4322), the gerAA, gerAB, and gerAC proteins of the *B. subtilis* spore, encoded by the gerA operon, are required for the germination response to L-alanine as the sole germinant. They encode the components of the germination apparatus that respond directly to this germinant, mediating the spore's response. Homologues of the gerA genes are found in every spore forming bacteria so far examined. The gerA operon is expressed in the forespore, and the level of expression of the operon appears to be low. According to Hudson et al, the gerAA and gerAC proteins are localized in the inner spore membrane, which forms a boundary around the cellular compartment of the spore. Thus, according to preferred embodiments of the invention, the gerA protein is typically either a gerAA or a gerAC protein.

The invention includes a bacterial spore comprising a modified gerA protein, wherein the extracellular domain of the modified gerA protein binds an agent which is not bound by the extracellular domain of the wild-type gerA protein, and wherein the agent is a germinant that stimulates germination of the bacterial spore. Typically, the modified extracellular domain of the gerA protein binds the agent at a level at least 10× greater than does the extracellular domain of the wild-type, i.e. unmodified, gerA protein. Preferably, the modified extracellular domain of the gerA protein binds the agent at a level at least 20×, or at least 30×, or at least 40×, or at least 50× greater, or more preferably at a level at least 100×, or at least 500×, or at least 1000× greater, than does the extracellular domain of the unmodified gerA protein. Most preferably, the extracellular domain of the unmodified gerA protein does not bind the agent, or it only does so at an undetectable level.

Typically, the spore with the modified gerA extracellular domain germinates, in the presence of the agent, at a level at least 10× greater than does an otherwise equivalent spore with a native, i.e. unmodified, gerA extracellular domain. Preferably, the spore with the modified gerA extracellular domain germinates, in the presence of the agent, at a level at least 20×, or at least 30×, or at least 40×, or at least 50× greater, or more preferably at a level at least 100×, or at least 500×, or at least 1000× greater, than does an otherwise equivalent spore with an unmodified gerA extracellular domain in the presence of that agent. Most preferably, the otherwise equivalent spore with the unmodified gerA extracellular domain, in the presence of the agent, does not undergo germination at above basal level, or it only does so at an undetectable level.

In an embodiment, the spore may have been engineered to express two, or more, modified gerA receptors with different extracellular domains that recognise and stimulate germination in the presence of different agents.

It is appreciated that the modified gerA protein may be exogenously added, i.e. the bacteria from which the spore is formed has been genetically manipulated to express the modified gerA protein on the spore generated therefrom. Accordingly, it may be preferred that the native gerA protein in the bacteria is not expressed on the bacterial spore. Thus, in an embodiment, the modified bacterial spore may have the 'native' or 'wild-type' gerA gene inactivated, knocked-out, knocked-down, or deleted such that the 'native' or 'wild-type' gerA protein is either not expressed or is non-functional or is expressed at a level at least 10× lower than the modified gerA protein. More preferably, the 'native' or 'wild-type' gerA protein is expressed at a level at least 20×, or at least 30×, or at least 40×, or at least 50× lower, or still more preferably at least 100×, or at least 500×, or at least 1000× lower, than the modified gerA protein.

It may also be preferred that other germination receptors on the bacterial cell are also not expressed or non-functional to minimise germination from 'normal' germinants rather than the desired, engineered germinant. Thus, in an embodiment, at least two, or at least 3, or at least 4 or at least 5, or more of the native/wild-type germination receptors have been inactivated, knocked-out, knocked-down or deleted. The germination receptors that could be inactivated, knocked-out, knocked-down or deleted include the proteins of the gerA, gerB and gerK operons (Paidhungat & Setlow (2000) "Role of ger proteins in nutrient and non-nutrient triggering of spore germination in *Bacillus subtilis*". *J. Bacteriol.* 182(9): 2513-19).

In a specific embodiment, all of the bacterial germination receptors, other than the modified prkC and/or gerA proteins, have been inactivated, knocked-out, knocked-down, or deleted such that they are either not expressed, are expressed at a significantly reduced level, or are non-functional. In this way, germination can only be induced by the specific, engineered mutants, thereby making the modified spores far more specific (reducing or eliminating background levels of germination). Thus, the invention may include the use of receptor-less germination mutants, for example as described with respect to *B. subtilis* (Paidhungat & Setlow, 2000).

In an embodiment, the bacterial spore may comprise both a modified prkC protein and a modified gerA protein, as described above. This may result in germination in response to two distinct engineered stimuli which do not stimulate germination of a bacterial spore comprising wild-type prkC and wild-type gerA proteins.

Typically, in this aspect of the invention, the modified bacterial spore undergoes germination, in the presence of a germinant, at a level at least 10× greater than an otherwise equivalent bacterial spore with unmodified prkC and gerA proteins in the presence of the germinant. Preferably the modified spore undergoes germination, in the presence of a germinant, at a level at least 20×, or at least 30×, or at least 40×, or at least 50× greater than the otherwise equivalent unmodified bacterial spore in the presence of the germinant. More preferably, the modified spore undergoes germination, in the presence of a germinant, at a level at least 100×, or at least 500×, or at least 1000× greater than the otherwise equivalent unmodified bacterial spore in the presence of the germinant. Most preferably, the presence of the germinant does not cause the otherwise equivalent unmodified bacterial spore with unmodified, i.e. wild-type, prkC and gerA proteins to undergo germination at above basal level, or it only does so at an undetectable level.

In such an embodiment, it may be preferred that the native or wild-type prkC and gerA proteins are each not expressed, are expressed at significantly reduced levels, or are non-functional.

It is appreciated that the bacterial spore may be from any bacterium that is capable of forming a bacterial spore. Thus, the bacterial spore may be from an endospore-forming bacterium selected from the genera *Bacillus, Clostridium, Acetonema, Alkalibacillus, Alkaliphillus, Ammoniphilus, Amphibacillus, Anaerobacter, Anaerospora, Aneurinibacillus, Anoxybacillus, Brevibacillus, Caldanaerobacter, Caloramator, Caminicella, Cerasibacillus, Clostridiisalibacter, Cohnella, Dendrosporobacter, Desulfotomaculum, Desulfosporomusa, Desulfosporosinus, Desulfovirgula, Desulfunispora, Desulfurispora, Filifactor, Filobacillus, Gelria, Geobacillus, Geosporobacter, Gracilibacillus, Halonatronum, Heliobacterium, Heliophilum, Laceyella, Lentibacillus, Lysinibacillus, Mahella, Metabacterium, Moorella, Natroniella, Oceanobacillus, Orenia, Ornithinibacillus, Oxalophagus, Oxobacter, Paenibacillus, Paraliobacillus, Pelospora, Pelotomaculum, Piscibacillus, Planifilum, Pontibacillus, Propionispora, Salinibacillus, Salsuginibacillus, Seinonella, Shimazuella, Sporacetigenium, Sporoanaerobacter, Sporobacter, Sporobacterium, Sporohalobacter, Sporolactobacillus, Sporomusa, Sporosarcina, Sporotalea, Sporotomaculum, Syntrophomonas, Syntrophosphora, Tenuibacillus, Tepidibacter, Terribacillus, Thalassobacillus, Thermoacetogenium, Thermoactinomyces, Thermoalkalibacillus, Thermoanaerobacter, Thermoanaeromonas, Thermobacillus, Thermoflavimicrobium, Thermovenabulum, Tuberibacillus, Virgibacillus* and *Vulcanobacillus.*

More preferably, the bacterial spore is from a genus selected from *Bacillus* or *Clostridium.*

In an embodiment, if the bacterial spore is a spore of a *Bacillus* sp., it may be a spore of *B. subtilis, B. anthracis, B. cereus, B. clausii, B. halodurans, B. licheniformis, B. thuringiensis* or *B. weihenstephanensis.*

In an embodiment, if the bacterial spore is a spore of a *Clostridium* sp., it may be a spore of *C. acetobutylicum, C. beijerinckii, C. botulinum, C. cellulolyticum, C. difficile, C. kluyveri, C. novyi, C. perfringens, C. phytofermentans, C. tetani* or *C. thermocellum.*

In another embodiment, if the bacterial spore is a spore of an *Alkaliphillus* sp., it may be a spore of *A. oremlandii.*

The desired engineered germinant (e.g., agent that binds the modified prkC or gerA protein) may be an antibiotic; a hormone such as erythropoietin; a growth factor such as PDGF; a steroid; a neurotransmitter; or a small molecule pharmaceutical compound such as a rapamycin; a nucleic acid such as DNA; a peptide; a truncated version of a hormone or signalling protein; a monosaccharide, disaccharide or other carbohydrate; a metal or metal ion, such as copper; an aminoglycoside; or an alkaloid, such as monoindole alkaloid drugs. In the examples rapamycin, erythropoietin, DNA, copper, PDGF and thrombin were shown to be suitable.

The desired engineered germinant may be DNA. In an embodiment, the germinant may be DNA from a microbial pathogen. In one embodiment, the microbial pathogen is a bacterium (e.g. of genus *Salmonella, Streptococcus, Haemophilus, Klebsiella, Escherichia, Mycobacterium, Chlamydia, Yersinia, Brucella, Legionella, Shigella, Pseudomonas, Enterococcus, Enterobacter, Proteus, Morganella, Stenotrophomonas, Acinetobacter*), a fungus (e.g. of genus *Cryptococcus, Aspergillus, Candida*), or a protozoan (e.g. of genus *Plasmodium, Treponema, Toxoplasma, Trypanosoma, Leishmania, Entamoeba, Balantidium, Giardi, Cryptosporidium, Cyclospora, Isospora, Microsporidia*). The pathogen may be a common cause of hospital acquired infections such as *Clostridium difficile* (in which case it is preferred that the modified bacterial spore is a *Bacillus* sp). In a preferred embodiment, the pathogen is methicillin-resistant *Staphylococcus aureus* (MRSA).

In an embodiment, the microbial pathogen could be one that causes one of the animal diseases notifiable to the World Organisation for Animal Health (OIE). These diseases include the multiple species diseases Anthrax, Aujeszky's disease, Bluetongue, Brucellosis (*Brucella abortus*), Brucellosis (*Brucella melitensis*), Brucellosis (*Brucella suis*), Crimean Congo haemorrhagic fever, Echinococcosis/hydatidosis, Epizootic haemorrhagic disease, Equine encephalomyelitis (Eastern), Foot and mouth disease, Heartwater, Japanese encephalitis, Leptospirosis, New world screwworm (*Cochliomyia hominivorax*), Old world screwworm (*Chrysomya bezziana*), Paratuberculosis, Q fever, Rabies, Rift Valley fever, Rinderpest, Surra (*Trypanosoma evansi*), Trichinellosis, Tularemia, Vesicular stomatitis, West Nile fever; the cattle diseases: Bovine anaplasmosis, Bovine babesiosis, Bovine genital campylobacteriosis, Bovine spongiform encephalopathy, Bovine tuberculosis, Bovine viral diarrhoea, Contagious bovine pleuropneumonia, Enzootic bovine leukosis, Haemorrhagic septicaemia, Infectious bovine rhinotracheitis/infectious, pustular vulvovaginitis, Lumpy skin disease, Theileriosis, Trichomonosis, Trypanosomosis (tsetse-transmitted); the Sheep and goat diseases: Caprine arthritis/ encephalitis, Contagious agalactia, Contagious caprine pleuropneumonia, Enzootic abortion of ewes (ovine chlamydiosis), Maedi-visna, Nairobi sheep disease, Ovine epididymitis (*Brucella ovis*), Peste des petits ruminants, Salmonellosis (*S. abortusovis*), Scrapie, Sheep pox and goat pox; the equine diseases: African horse sickness,• Contagious equine metritis,• Dourine,• Equine encephalomyelitis (VVestern),• Equine infectious anaemia,• Equine influenza,• Equine *piroplasmosis*,• Equine rhinopneumonitis,• Equine viral arteritis,• Glanders,• Venezuelan equine encephalomyelitis; the swine diseases: African swine fever, Classical swine fever, Nipah virus encephalitis, Porcine cysticercosis, Porcine reproductive and respiratory syndrome, Swine vesicular disease, Transmissible gastroenteritis; the avian diseases: Avian chlamydiosis,• Avian infectious bronchitis, Avian infectious laryngotracheitis, Avian mycoplasmosis (*M. gallisepticum*), Avian mycoplasmosis (*M. synoviae*), Duck virus hepatitis, Fowl cholera,• Fowl typhoid,• Highly pathogenic avian influenza and low pathogenic avian influenza in poultry as per Chapter 10.4. of the Terrestrial Animal Health Code, Infectious bursal disease (Gumboro disease),• Marek's disease,• Newcastle disease, Pullorum disease, Turkey rhinotracheitis; the Lagomorph diseases Myxomatosis or Rabbit haemorrhagic disease; the fish diseases: Epizootic haematopoietic necrosis, Infectious haematopoietic necrosis, Spring viraemia of carp, Viral haemorrhagic septicaemia, Infectious salmon anaemia, Epizootic ulcerative syndrome, Gyrodactylosis (*Gyrodactylus salaris*), Red sea bream iridoviral disease, Koi herpesvirus disease; the Crustacean diseases: Taura syndrome, White spot disease, Yellowhead disease, Infectious hypodermal and haematopoietic necrosis, Crayfish plague (*Aphanomyces astaci*), Infectious myonecrosis, White tail disease; the bee diseases: Acarapisosis of honey bees,• American foulbrood of honey bees,• European foulbrood of honey bees,• Small hive beetle infestation (*Aethina tumida*), Tropilaelaps infestation of honey bees,• Varroosis of honey bees; the mollusc diseases: Infection with *Bonamia ostreae*,• Infection with *Bonamia exitiosa*,• Infection with *Marteifia refringens*,• Infection with *Perkinsus marinus*,• Infection with *Perkinsus olseni*,• Infection with *Xenohaliotis cafiforniensis*,• Infection with abalone herpes-like virus; the amphibian dieases: Infection with *Batrachochytrium dendrobatidis*, Infection with ranavirus; and the other diseases camelpox and Leishmaniosis.

In an embodiment, the desired engineered germinant for the bacterial spore may be an environmental contaminant. In certain embodiments, the environmental contaminant may be any of soil, air, water and biological contaminants; organic compounds, metals, metal-containing compounds, and mixtures thereof; halogenated organic compounds, chlorinated hydrocarbons, fluorinated hydrocarbons, chlorofluoro hydrocarbons, or mixtures thereof, organophosphates, polyaromatic hydrocarbons or herbicides (e.g., photosynthesis inhibitors). The contaminants may be ones that comprise Ammonia, Arsenic/CCA, Asbestos, Blue-green algae, Formaldehyde, Lead, Mercury, Methamphetamine, nitrates, Pfiesteria, Sulfuric Acid, Trichloroethylene (TCE) and mixtures thereof.

In this embodiment, the presence of the environmental contaminant is detected by detecting germination of the spores using methods known in the art and described herein.

Additionally or alternatively, in a more preferred embodiment, the bacterial spore may be engineered to express an enzyme that degrades the environmental contaminant after germination. Suitable enzymes include organophosphate hydrolase, laccase, organophosphate acid anhydrolase, lignin peroxidase, manganese peroxidase, and halogenase (Haritash and Kaushik (2009) "Biodegradation aspects of polycyclic aromatic hydrocarbons (PAHs): a review". *Journal of Hazardous Materials* 169: 1-15; Singh & Walker (2006) "Microbial degradation of organophosphorus compounds". *FEMS Microbiol Rev* 30: 428-471). Suitable molecular biology techniques for manipulating bacteria to express suitable enzymes are well known in the art, and include the use of promoters such as vegA, ctc, gsiB, constitutive sigma A or sigma B promoters, regulated promoters. The *B. subtilis* promoter database (dbtbs.hgc.jp) provides additional examples (Ishii et al (2001) "DBTBS: a database of *Bacillus subtilis* promoters and transcription factors". *Nucl. Acids Res.* 29(1): 278-280; Sierro et al (2008) "DBTBS: a database of transcriptional regulation in *Bacillus subtilis* containing upstream intergenic conservation information. *Nucl. Acids Res.* 36 (Database issue):D93-6).

In an embodiment, the bacterial spore may have been engineered to express one or more enzymes, such as phytases or cellulases, after germination, which improve the digestibility of animal feed. Similarly, the bacterial spore may have been engineered to produce one or more compounds that enhance the nutritional value of the feed as are known in the art. Typically, the germinant would be administered to the animal separately from the bacterial spores, either one of which may be placed into the feed. In other embodiments, spores would be designed to germinate after digestion. Phytases enhance phosphate and mineral uptake in monogastric animals (such as poultry, swine, and fish), that cannot metabolize phytate and can be of bacterial, fungal, or plant origin (Rao et al (2009) "Molecular characterization, physicochemical properties, known and potential applications of phytases: An overview" *Critical Reviews in Biotechnology* 29(2): 182-198). Hydrolases are the primary enzyme incorporated in animal feed to improve the nutritional value of feed and can be composed of cellulases and/or hemicellulases, glucanase, pectinase, and xylanase (Bhat (2000) "Cellulases and related enzymes in biotechnology" *Biotechnology Advances* 18: 355-383). Suitable molecular biology techniques for manipulating bacteria to express such enzymes are very well known in the art.

Preferably, the bacterial spore upon germination expresses a rapidly detectable indicator of germination. For example, germination typically results in the release of DPA-$Ca^{2+}$ which can be detected using any of the well known calcium and DPA responsive dyes and fluorophores, such as terbium salts. Suitable calcium responsive dyes include: Fluo-3, Fluo-4, Rhod-2, Calcium Green, Calcium Orange and Calcium Crimson, Oregon Green 488, Fura Red, Calcein and Fura Dextran (Minta et al (1989) *J Biol Chem* 264: 8171-8178; Micu et al (2007) *Nat. Med.* 13: 874-879; Lu & Paige (2007) *J Fluoresc* 17: 739-748; Chiu & Haynes (1977) *Biophys J* 18: 3-22).

Thus the rapidly detectable indicator of germination may be a fluorescent indicator, a bioluminescent indicator, or a colorimetric indicator of germination. As described in U.S. Pat. No. 6,872,539, for example, the bacteria may have been genetically modified to carry chromosomal lux bioluminescence genes (Cook et al (1993) *J. Appl. Bacteriol.* 75: 350-359) such that the spores become bioluminescent during germination. In another embodiment, the spores have been genetically modified to carry chromosomal lac genes producing β-D-galactopyranoside as a reporter enzyme which can be detected by a variety of sensitive standard assays. In yet another embodiment, the spores may have been genetically modified to carry chromosomal genes producing a detectable dye. Alternatively, in another preferred embodiment, the bacteria may have been genetically modified to carry a chromosomal gene encoding a fluorescent protein, such as GFP, which can serve as an indicator of spore germination because of its strong and specific fluorescence.

Another aspect of the invention provides a method for detecting the presence of a compound, the method comprising providing a bacterial spore according to any of the previous aspects of the invention, and detecting germination of the spore. In this aspect of the invention, the bacterial spore has been modified such that it undergoes germination in the presence of the compound, typically, by modifying the extracellular region of the prkC (or gerA) protein so that it binds to the compound to be detected, as described above. Thus germination of the spore indicates the presence of the compound. Typically, also, the efficiency or the rate of germination indicates the amount or concentration of the compound that is present.

In an embodiment, the compound to be detected is an antibiotic, a hormone, a growth factor, a steroid, a neurotransmitter, a small molecule pharmaceutical compound, a peptide; a truncated version of a hormone or signalling protein; a monosaccharide, disaccharide or other carbohydrate; a metal or metal ion; an aminoglycoside; or an alkaloid, such as monoindole alkaloid drugs, as described above. In an alternative embodiment, the compound to be detected may be a nucleic acid molecule, such as a DNA molecule, for instance from a microbial pathogen, as described above. Typically, in this embodiment, the method may be performed on a sample suspected of containing the microbial pathogen, for example a patient sample, or it could be a sample taken for routine monitoring.

In another embodiment, the compound to be detected may be an environmental contaminant, such as described above. It is appreciated that it in this embodiment, the method may be performed on a sample taken from the environment that is suspected of being contaminated, or it could be a sample taken for routine monitoring. Alternatively, however, the method may be performed in the environment in situ.

It is appreciated that for applications when it is desired to detect the presence of more than one compound, for example when detecting environmental contaminants or microbial pathogens, it is possible to 'multiplex' the assay by combining spores that germinate in the presence of different compounds. In the event of a positive result from the pooled spores, the presence of individual compounds can thereafter be ascertained. Thus, the method can also be used as a rapid method of identifying the presence of an individual compound from within a multiplicity of compounds.

In another aspect, the invention provides a bacterial cell or a bacterial cell culture from which a bacterial spore according to previous aspects of the invention can be produced.

In still another aspect, the invention provides a kit of parts comprising:
 a modified bacterial spore according to previous aspects of the invention as described above, and either or both of
 reagents for detecting germination of the bacterial spore as are well known in the art, and/or
 a germinant that stimulates germination of the modified bacterial spore but which does not stimulate germination of an equivalent unmodified bacterial spore.

Standard methods for measuring bacterial spore germination are well known in the art and include the loss of heat resistance of spores (Shah et al, 2008), or the change in optical density of a culture (Paidhungat & Setlow, 2000).

In a preferred embodiment, the kit further comprises unmodified bacterial spores suitable for use as a control.

In another aspect, the invention provides animal feed comprising a modified bacterial spore according to the invention which has been engineered to express one or more enzymes, such as phytases or cellulases, after germination, which improve the digestibility of animal feed and/or to produce one or more compounds that enhance the nutritional value of the feed, as described above.

In an embodiment, the invention provides a kit comprising, separately:
 a modified bacterial spore according to the invention which has been engineered to express one or more enzymes, such as phytases or cellulases, after germination, which improve the digestibility of animal feed and/or to produce one or more compounds that enhance the nutritional value of the feed, as described above; and
 a germinant that stimulates germination of the modified bacterial spore but which does not stimulate germination of an equivalent unmodified bacterial spore, wherein either or both of the bacterial spore and the germinant are comprised in animal feed.

It is appreciated that the bacterial spores of the invention may have been engineered such that they respond to specific markers and act as biosensors. For example, the spore may be engineered to express an extracellular domain of a receptor known to bind a specific ligand, whose presence it is desirable to detect.

Accordingly, another aspect of the invention provides a biosensor device comprising a bacterial spore according to previous aspects of the invention.

Preferably, the biosensor device further comprises means to readily detect germination upon detection of a specific marker.

For example, the device may include substrates to detect the expression of reporter proteins upon germination, or may be integrated with electronic devices, such as ion-selective field effect transistors (ISFETs) to transduce the ion secretion (which happens upon germination) to an electronic signal.

In an embodiment, the biosensor device further comprises an electronic read-out corresponding to the calcium ion release during germination.

In an embodiment, the biosensor device further comprises a detector of a fluorescent indicator, bioluminescent indicator, or colorimetric indicator of germination that is expressed by the bacterial spore during germination.

It is appreciated that spore biosensors will be robust to harsh environmental conditions, unlike protein-based assays such as ELISA. The ability of spores to survive desiccated at room temperatures enables them to be more easily integrated into electronic devices or used in developing world applications (where refrigeration requirements preclude the use of protein-based methods).

In one embodiment, the biosensor device is a multiplex biosensor, and so may detect more than one specific agent. For example, the spore of the device may be engineered such that it can detect multiple ligands by expressing multiple prkC receptors with different extracellular domains that recognise different agents.

It is further appreciated that the spores may be engineered to induce a particular cellular event upon recognition of a specific agent. For example, the spores may be engineered to contain particular genetic loci downstream of prkC and gerA responsive promoters. In this way, upon recognition of a specific agent and subsequent activation of the prkC, and/or gerA, signalling pathways, the expression of certain genes can be turned on. In a particular example, upon sensing of animal feedstocks, it may be desirable to turn off/kill the bacteria by expressing a gyrase inhibitor protein or other cell death protein.

In a specific embodiment, the invention provides a method for detecting the presence of MRSA in a sample, the method comprising:
providing modified bacterial spores which undergo germination in the presence of MRSA DNA, for example the MRSA mecA DNA;
incubating the sample with the modified bacterial spores; and
testing for germination for the bacterial spores,
wherein increased germination of the bacterial spores indicates the presence of MRSA in the sample.

Typically, oligonucleotides that are complementary to MRSA DNA have been added to the extracellular domain of germination receptors, such as the prkC or gerA receptors, of the bacterial spores, such that binding of MRSA DNA to the oligonucleotides induces germination of the spores. The use of 'bridging oligos' as described in Example 3 and 4 supports the inventors contention that it is the dimerisation of the germination receptors, such as the prkC or gerA receptors, that results in germination.

In an embodiment, and as shown in Example 4, testing for the germination for the bacterial spores may comprise adding Terbium ions and detecting fluorescence in the presence of UV light.

Typically, in this embodiment, the presence of MRSA (by detecting MRSA specific DNA) can be detected within 30 minutes, and preferably within 15 minutes.

As described above and in the Examples, multiple applications of a bacterial spore as a biosensor can be developed making use of the extraordinarily high affinity of streptavidin and related molecules for biotin and biotin analogues, as is very well known in the art. Accordingly, the invention provides a prkC protein from a spore-forming bacterium, characterised in that the extracellular domain of the protein has been modified to comprise or consist of a biotin-binding region of streptavidin, avidin or neutravidin.

Typically, the prkC protein to be modified is one from a *Bacillus* or a *Clostridium*, such as *B. subtilis*, *B. anthracis*, *B. cereus*, *B. clausii*, *B. halodurans*, *B. licheniformis*, *B. thuringiensis* or *B. weihenstephanensis* (most preferably *B. subtilis*) or *C. acetobutylicum*, *C. beijerinckii*, *C. botulinum*, *C. cellulolyticum*, *C. difficile*, *C. kluyveri*, *C. novyi*, *C. perfringens*, *C. phytofermentans*, *C. tetani* or *C. thermocellum*. As described above, the prkC sequence of many bacteria are known in the art, and the prkC sequence of other Bacilli and Clostridia can readily be obtained based upon the high level of conservation shared by the prkC proteins (Xiao et al, 2010)

The biotin-binding region of streptavidin is very well known in the art. In an embodiment, the biotin-binding region of streptavidin comprises or consists of the last 129 residues of SEQ ID No: 14 as shown in Example 3, below, or comprises or consists of an amino acid sequence that is at least 90% (for example at least 91%, at least 92%, at least 93%, at least 94%, at least 95%, at least 96%, at least 97%, at least 98% or at least 99%) identical to SEQ ID NO: 14. The skilled person is well aware of the regions of streptavidin that allow for binding to biotin, and variants of the streptavidin sequence that allow for binding to biotin, as discussed above.

The invention further includes a nucleic acid molecule encoding the modified prkC protein.

The invention still further includes an expression vector comprising the nucleic acid molecule and suitable regulatory regions, such as vegA, ctc, gsiB, constitutive sigma A or sigma B promoters and regulated promoters, such as those mentioned above, and including those listed in the *B. subtilis* promoter database, for expressing the modified prkC protein on bacterial spores.

The invention further includes a spore forming bacteria comprising the nucleic acid molecule or the expression vector. Methods for transforming the spore forming bacteria with the nucleic acid molecule or the expression vector are well known in the art. In an embodiment, it is preferred that the native type prkC gene has been knocked-out, knocked-down or deleted in the spore forming bacteria. It is preferred that the spore forming bacteria are from the genus *Bacillus* or *Clostridium*, such as *B. subtilis*, *B. anthracis*, *B. cereus*, *B. clausii*, *B. halodurans*, *B. licheniformis*, *B. thuringiensis* or *B. weihenstephanensis* (most preferably *B. subtilis*) or *C. acetobutylicum*, *C. beijerinckii*, *C. botulinum*, *C. cellulolyticum*, *C. difficile*, *C. kluyveri*, *C. novyi*, *C. perfringens*, *C. phytofermentans*, *C. tetani* or *C. thermocellum*. It is preferred that the prkC protein (prior to its modification) is from the same species, and more preferably from the same strain, as the spore forming bacteria to which the nucleic acid molecule is added (and hence the bacterial spore on which it is expressed), although this is not considered to be essential as the intracellular region of a prkC protein from one spore-forming bacterial species is expected to be able to function in related bacterial species.

It will also be appreciated that the invention further provides a method of making bacterial spores which undergo germination in the presence of a desired germinant, the method comprising:
providing bacteria, the spores of which do not germinate in the presence of the desired germinant,
inserting a polynucleotide encoding a modified bacterial PrkC protein into the bacteria, wherein the extracellular domain of the modified PrkC protein binds the desired germinant; and
inducing sporulation of bacteria expressing the modified PrkC protein.

Methods for the genetic manipulation of *Bacillus* sp. are very well known in the art (e.g., *Bacillus* (Biotechnology Handbooks) Colin R. Harwood (Editor). Publisher: Springer; 1st Edition (Jun. 30, 1989) ISBN-10: 0306431378. ISBN-13: 978-0306431371).

Methods for the genetic manipulation of for Clostridia are also known in the art and are described, for example, by Heap et al (2007). *J. Microbiol. Methods* 70: 452-464; in the book entitled "Clostridia: Molecular Biology in the Postgenomic Era", by Brüggemann & Gottschalk (Eds.), Caister Academic Press, Norfolk, pp. 179-198 (2009), especially the chapter by Heap et al; and Heap et al (2010) *J. Microbiol. Methods* 80: 49-55.

Further aspects of the invention relate to directed evolution methods for changing receptor specificity and thus increasing the range of germinants which induce germination of bacteria spores. Typically, this will involve randomising the extracellular domain of a germination receptor protein, such as prkC, and screening modified bacterial clones that germinate in response to new receptor ligands.

Protein function can be modified and improved in vitro by a variety of methods that are well known in the art, and so do not require describing in detail. Suitable methods include site directed mutagenesis (Alber et al., *Nature*, 5; 330(6143):41-46, 1987) combinatorial cloning (Huse et al., *Science*, 246: 1275-1281, 1989; Marks et al., Biotechnology, 10: 779-783, 1992) and random mutagenesis combined with appropriate selection systems (Barbas et al., *PNAS. USA*, 89: 4457-4461, 1992).

The method of random mutagenesis together with selection has been used in a number of cases to improve protein function and two different strategies exist. Firstly, randomisation of the entire gene sequence in combination with the selection of a variant (mutant) protein with desired characteristics, followed by a new round of random mutagenesis and selection. This method can then be repeated until a protein variant is found which is considered optimal (Schier R. et al., *J. Mol. Biol.* 1996 263 (4): 551-567). Here, the traditional route to introduce mutations is by error prone PCR (Leung et al., *Technique*, 1: 11-15, 1989) with a mutation rate of approximately 0.7%. Secondly, defined regions of the gene can be mutagenised with degenerate primers, which allows for mutation rates of up to 100% (Griffiths et al., *EMBO. J*, 13: 3245-3260, 1994; Yang et al., *J. Mol. Biol.* 254: 392-403, 1995).

Random mutation has been used extensively in the field of antibody engineering. Antibody genes formed in vivo can be cloned in vitro (Larrick et al., *Biochem. Biophys. Res. Commun.* 160: 1250-1256, 1989) and random combinations of the genes encoding the variable heavy and light genes can be subjected to selection (Marks et al., *Biotechnology*, 10: 779-783, 1992). Functional antibody fragments selected by these methods can be further improved using random mutagenesis and additional rounds of selections (Schier R. et al., *J. Mol. Biol.* 1996 263 (4): 551-567).

Typically, the strategy of random mutagenesis is followed by selection. Variants with interesting characteristics can be selected and the mutated DNA regions from different variants, each with interesting characteristics, combined into one coding sequence (Yang et al., *J. Mol. Biol.* 254: 392-403, 1995).

Suitable methods are also described in PCT publications WO2007057682 (PCT/GB2006/004294) and WO2003097834 (PCT/GB03/02102) by Alligator Bioscience.

Combinatorial pairing of genes has also been used to improve protein function, e.g. antibody affinity (Marks et al., Biotechnology, 10: 779-783, 1992).

Another known process for in vitro mutation of protein function, which is often referred to as "DNA shuffling", utilises random fragmentation of DNA and assembly of fragments into a functional coding sequence (Stemmer, *Nature* 370: 389-391, 1994). The DNA shuffling process generates diversity by recombination, combining useful mutations from individual genes. It has been used successfully for artificial evolution of different proteins, e.g. enzymes and cytokines (Chang et al. *Nature Biotech.* 17, 793-797, 1999; Zhang et al. *Proc. Natl. Acad. Sci. USA* 94, 4504-4509, 1997; Christians et al. *Nature Biotech.* 17, 259-264, 1999). The genes are randomly fragmented using DNase I and then reassembled by recombination with each other. The starting material can be either a homologous sequences (so-called family shuffling).

These techniques can be used in the following screening methods to produce germination receptor proteins, such as prkC, with variant extracellular domains which bind to novel agents that act as germinants.

Thus the invention provides a method for selecting a modified bacterial germination receptor protein which increases the efficiency of germination of bacterial spores in response to a desired germination agent, the method comprising the steps of:
  providing a polynucleotide that encodes a germination receptor protein of the bacteria;
  modifying the sequence of the polynucleotide to generate modified polynucleotides encoding variant forms of the germination receptor protein having sequence variation within the extracellular domain;
  expressing the modified polynucleotides to produce the variant forms of the germination receptor protein;
  screening the variant forms of the germination receptor protein for binding to the agent; and
  selecting a variant form of the germination receptor protein which has improved binding to the desired germination agent.

This method for selecting a modified bacterial germination receptor protein which increases the efficiency of germination of bacterial spores in response to a desired germination agent, includes the steps of:
  providing a plurality of germination receptor proteins having sequence variation within the extracellular domain (which can, for example, be made by the first three steps of the method described immediately above);
  screening the variant forms of the germination receptor protein for binding to the agent; and
  selecting a variant form of the germination receptor protein which has improved binding to the desired germination agent.

Any suitable binding assay can be used, and these are very well known in the art.

In an embodiment, the method further comprises the step of testing bacterial spores comprising the selected variant form of the germination receptor protein for increased efficiency of germination in the presence of the desired germination agent.

In a preferred embodiment, the desired germination agent does not stimulate germination of bacterial spores that do not express the variant form of the germination receptor protein. In an alternative embodiment, the desired germination agent stimulates germination of bacterial spores that do not express the variant form of the germination receptor protein, for example at low efficiency. In this embodiment, the method is typically for increasing the efficiency of germination in response to the desired germination agent.

The invention also provides a method for identifying a modified bacterial spore that germinates in response to a desired germination agent which does not stimulate germination of an equivalent unmodified bacterial spore, the method comprising the steps of:
  providing a polynucleotide that encodes a germination receptor protein of the bacteria;
  modifying the sequence of the polynucleotide to generate modified polynucleotides encoding variant forms of the germination receptor protein having sequence variation within the extracellular domain;
  expressing the modified polynucleotides to produce the variant forms of the germination receptor protein on bacterial spores;
  screening the bacterial spores for increased efficiency of germination in the presence of the desired germination agent; and
  selecting bacterial spores with increased efficiency of germination in the presence of the desired germination agent.

This method for identifying a modified bacterial spore that germinates in response to a desired germination agent, includes the steps of:
  providing a plurality of bacterial spores that express a corresponding plurality of variant forms of the germination receptor protein having sequence variation within the extracellular domain (which can, for example, be made by the first three steps of the method described immediately above);

screening the bacterial spores for increased efficiency of germination in the presence of the desired germination agent; and selecting bacterial spores with increased efficiency of germination in the presence of the desired germination agent.

The invention further provides a method for identifying novel germination agents of a modified bacterial spore, the method comprising the steps of:

providing a polynucleotide that encodes a germination receptor protein of the bacteria;

modifying the sequence of the polynucleotide to generate modified polynucleotides encoding variant forms of the germination receptor protein having sequence variation within the extracellular domain;

expressing the modified polynucleotides to produce the variant forms of the germination receptor protein on bacterial spores;

contacting the bacterial spores with at least one potential germination agent; and screening the bacterial spores for increased efficiency of germination in the presence of the at least one potential germination agent, thereby to identify novel germination agents of the modified bacterial spore.

This method for identifying novel germination agents of a modified bacterial spore, includes the steps of:

providing a plurality of bacterial spores that express a corresponding plurality of variant forms of the germination receptor protein having sequence variation within the extracellular domain (which can, for example, be made by the first three steps of the method described immediately above);

contacting the bacterial spores with at least one potential germination agent; and screening the bacterial spores for increased efficiency of germination in the presence of the at least one potential germination agent, thereby to identify novel germination agents of a modified bacterial spore.

In these screening methods of the invention, the germination receptor protein may be a prkC protein or a gerA protein. In other embodiments, the germination receptor protein may be a ger B or gerK protein (Paidhungat & Setlow, 2000). Preferably it is a prkC protein.

As mentioned above, the inventors have engineered spores so as to modify the range of molecules that can act as germinants. Since germination of spores can be readily determined by standard methods in the art and described herein, it will be appreciated that the engineered spores may be used to probe various activities of receptors such as signalling capacity. Thus, the invention provides a method for identifying an agent that modulates signalling of a receptor, the method comprising contacting an engineered spore of the invention that comprises the extracellular domain of the given receptor, contacting the spore with a test agent, and assessing receptor signalling. For example, the engineered spores may be used to screen for ligands for a given receptor, or to screen for molecules that modulate signalling of a given receptor. It is understood that such molecules may or may not themselves be receptor ligands, but may modulate receptor signalling, for example, by modulating ligand binding or by modulating receptor oligomerisation (e.g. dimerisation). In this way, the germination of the engineered spore is directly linked to the ability of the given receptor to bind a ligand and to the signalling capability of the given receptor, and can be used as an accurate readout. Conveniently, a chimera receptor comprising the wild PrkC kinase intracellular domain and the extracellular domain of the given receptor is used.

Accordingly, the invention provides a prkC protein from a spore-forming bacterium, characterised in that the extracellular domain of the protein has been modified to comprise or consist of an extracellular domain of a receptor protein other than a bacterial spore germination protein.

It is appreciated that, in an embodiment, the ligand binding region of the extracellular domain of the receptor protein can suitably be employed.

Typically, the prkC protein to be modified is one from a *Bacillus* or a *Clostridium*, such as *B. subtilis*, *B. anthracis*, *B. cereus*, *B. clausii*, *B. halodurans*, *B. licheniformis*, *B. thuringiensis* or *B. weihenstephanensis* (most preferably *B. subtilis*) or *C. acetobutylicum*, *C. beijerinckii*, *C. botulinum*, *C. cellulolyticum*, *C. difficile*, *C. kluyveri*, *C. novyi*, *C. perfringens*, *C. phytofermentans*, *C. tetani* or *C. thermocellum*. As described above, the prkC sequence of many bacteria are known in the art, and the prkC sequence of other Bacilli and Clostridia can readily be obtained based upon the high level of conservation shared by the prkC proteins (Xiao et al, 2010)

Very many receptor proteins are well known in the art, and their sequences are publicly available. In an embodiment, it may be preferred that the receptor is a single transmembrane receptor such as a hormone receptor or a growth factor receptor. Suitably, the receptor may be a cytokine receptor. The receptor may be a receptor tyrosine kinase (e.g., Class I, II or III), a serine-threonine protein kinase, or a guanylyl cyclase coupled receptor. In another embodiment, it may be preferred that the receptor is not a 7-TM GPCR. In an embodiment, the receptor protein is a mammalian receptor protein, for example a human receptor protein. In other embodiment, the receptor protein may be a microbial receptor protein such as a bacterial, fungal, protozoan or algal receptor protein, or a reptilian, avian or fish receptor protein.

The invention further includes a nucleic acid molecule encoding the modified prkC protein. The invention still further includes an expression vector comprising the nucleic acid molecule and suitable regulatory regions, such as those mentioned above, for expressing the modified prkC protein on bacterial spores. The invention further includes a spore forming bacteria comprising the nucleic acid molecule or the expression vector. It is preferred that the spore forming bacteria are from the genus *Bacillus* or *Clostridium*, such as *B. subtilis*, *B. anthracis*, *B. cereus*, *B. clausii*, *B. halodurans*, *B. licheniformis*, *B. thuringiensis* or *B. weihenstephanensis* (most preferably *B. subtilis*) or *C. acetobutylicum*, *C. beijerinckii*, *C. botulinum*, *C. cellulolyticum*, *C. difficile*, *C. kluyveri*, *C. novyi*, *C. perfringens*, *C. phytofermentans*, *C. tetani* or *C. thermocellum*. It is preferred that the prkC protein (prior to its modification) is from the same species, and more preferably from the same strain, as the spore forming bacteria to which the nucleic acid molecule is added (and hence the bacterial spore on which it is expressed), although this is not considered to be essential as the intracellular region of a prkC protein from one spore-forming bacterial species is expected to be able to function in related bacterial species.

In one embodiment, the engineered spores of the invention may be used to screen for ligands, such as agonists or antagonists, of a given receptor. An agonist of a receptor is expected to increase germination of spores whereas an antagonist is expected to decrease germination of spores.

In another embodiment, the engineered spores of the invention may be used to screen for molecules that modulate receptor oligomerisation (e.g. dimerisation). PrkC kinase is known to dimerise upon ligand binding, and so the spores may be used to identify molecules that modulate such dimerisation.

In a further embodiment, the engineered spores of the invention may be used to screen for molecules that modulate binding of any pair of binding agents, for example a pair of proteins. Both individual binding agents are expressed on, or as, the extracellular domain of a bacterial PrkC protein, which result in dimerisation leading to the induction of dimerisation. Any agent that modulates the binding between the two binding partners, and hence affects dimerisation of the modified prkC, will affect the efficiency of germination, and can readily be detected. In this way, the interaction between any two binding partners can be investigated, and agonists or antagonists thereof identified.

The test agent used in this screening aspect of the invention may be any of a polypeptide, an antibody, a small molecule (e.g. a small molecule with a molecule weight less than 5000 Daltons), a natural product, a peptidomimetic, or a nucleic acid.

It is appreciated that in the methods described herein, which may be drug screening methods, a term well known to those skilled in the art, the test agent may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 Daltons and which may be water-soluble. A drug-like compound may additionally exhibit features of selective interaction with a particular protein or proteins and be bioavailable and/or able to penetrate target cellular membranes or the blood:brain barrier, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

Thus in one embodiment, the method further comprises modifying a test agent which has been shown to modulate the signalling capability of a given receptor, and testing the ability of the modified test reagent to modulate a signalling capability of a given receptor.

All of the documents referred to herein are incorporated herein, in their entirety, by reference.

The listing or discussion of an apparently prior-published document in this specification should not necessarily be taken as an acknowledgment that the document is part of the state of the art or is common general knowledge.

The invention will now be described in more detail by reference to the following Examples and Figures.

FIG. 1 is a representation of the *B. subtilis* spore structure. The four layers (from the inside, outwards) are the core, cortex, coat and exosporium. The core is dehydrated and contains a large store of dipicolinic acid and $Ca^{2+}$. The cortex is made of layers of peptidoglycan, and must be hydrolysed during germination. The coat is made of layers of proteins, and excludes large molecules such as enzymes. The exosporium has no known role in germination.

FIG. 2: Bacterial spores: biology in stand-by mode. This figure is a representation of bacterial sporulation and germination. Bacteria sporulate under starvation conditions; spores are resistant to heat, radiation, pH extremes, and desiccation; spores are metabolically dormant, but can sense the environment; activation, germination, and outgrowth occur when environmental conditions improve.

FIG. 3 is a representation of the potential of 'programmed' spore germination in response to an outside signal (an engineered 'germinant') as indicated by the star. Programming spores to germinate in response to desired engineered signals can be used to provide robust bio sensors, including "mix and measure" reagents, on-demand protein and drug production, environmental "sentinels" for bioremediation, and synthetic genetic devices in standby mode.

Figure 1:
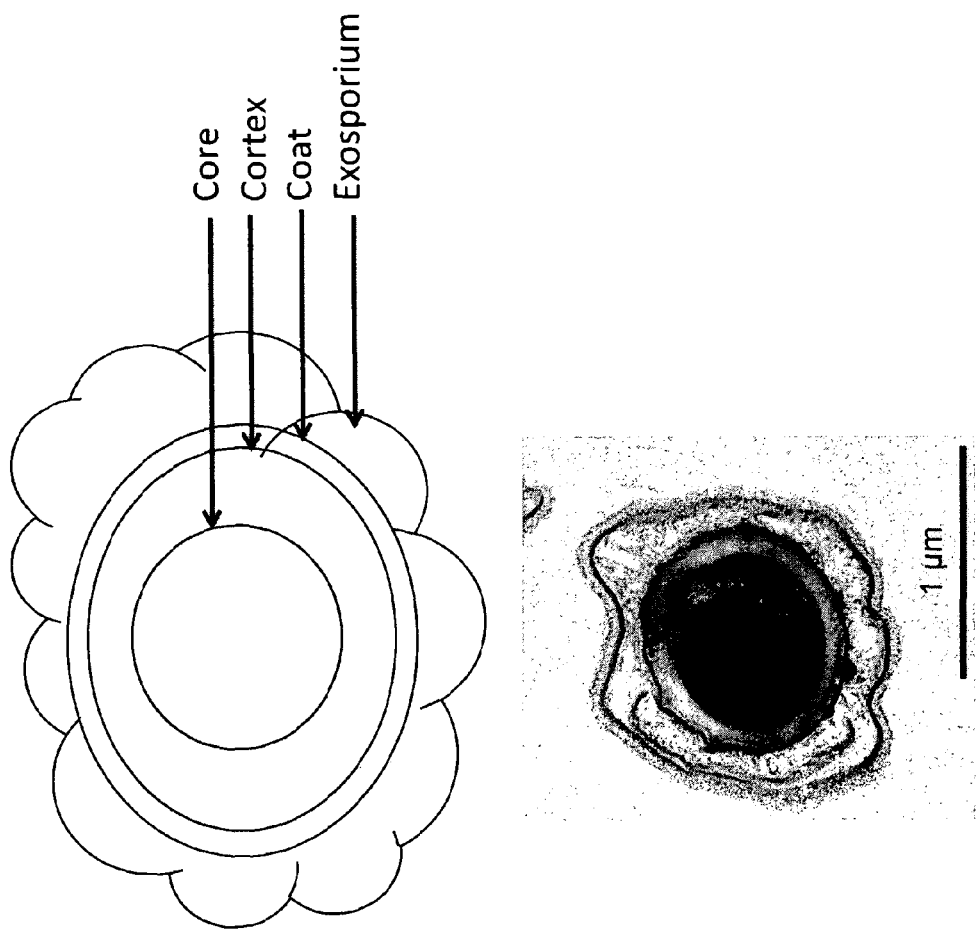
Figure 2:
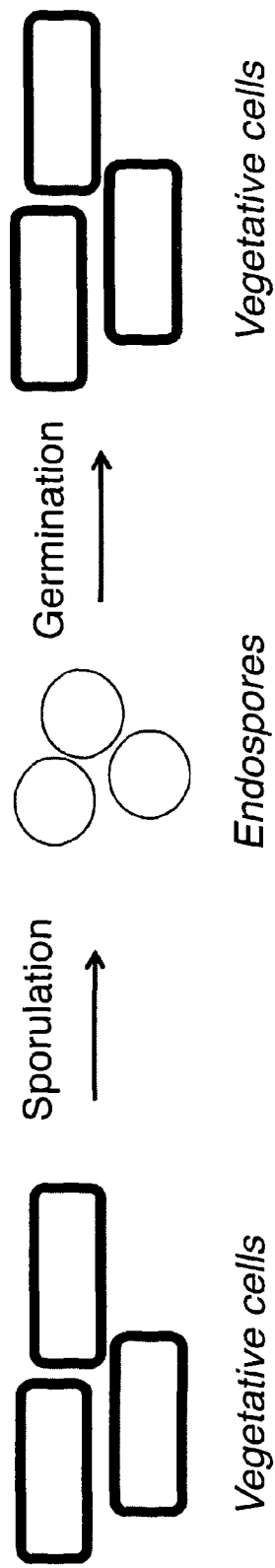
Figure 4:
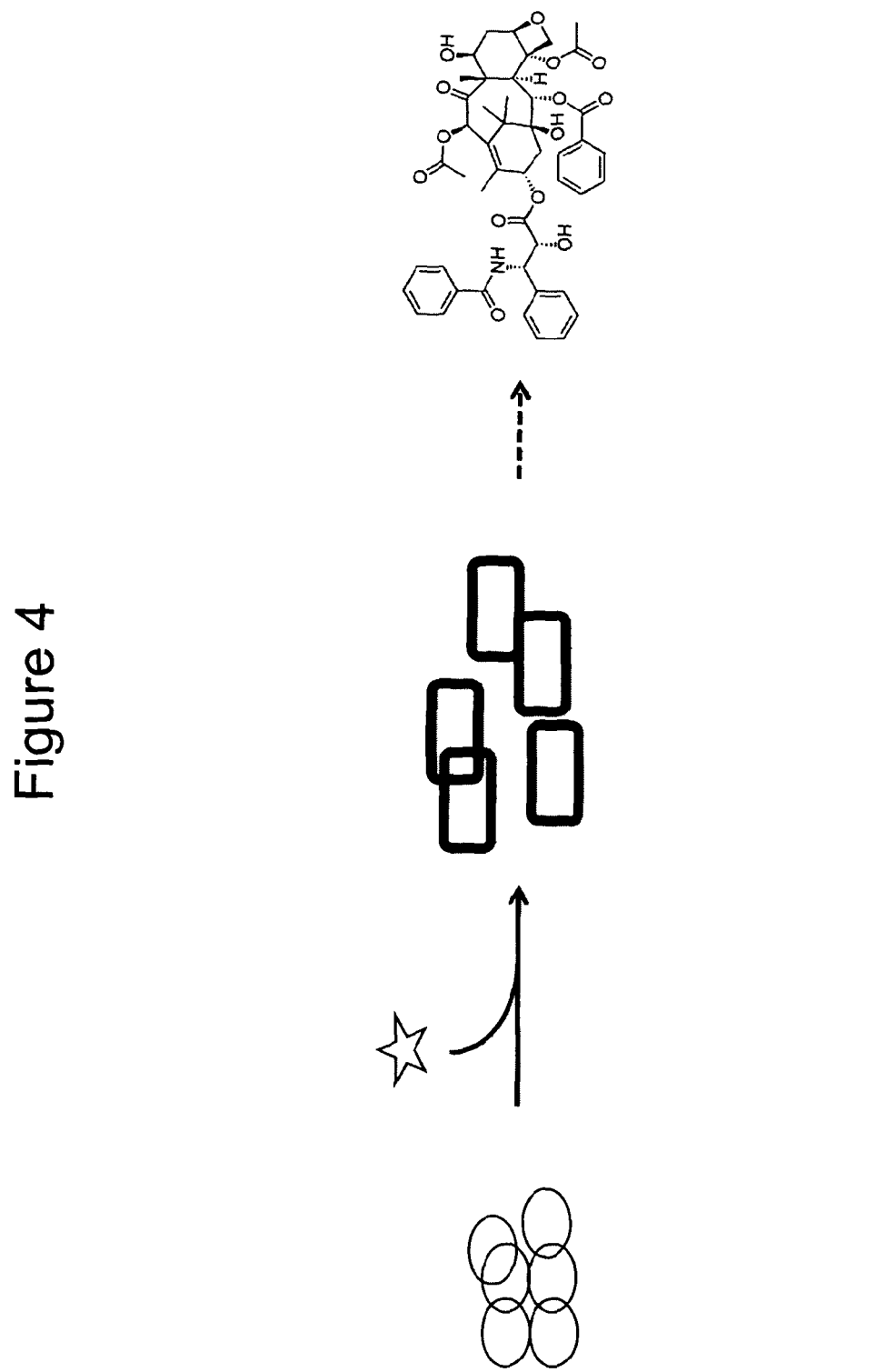
FIG. 4 is a representation of using 'programmed' spore germination for 'on-demand' protein or drug production.
Figure 5:
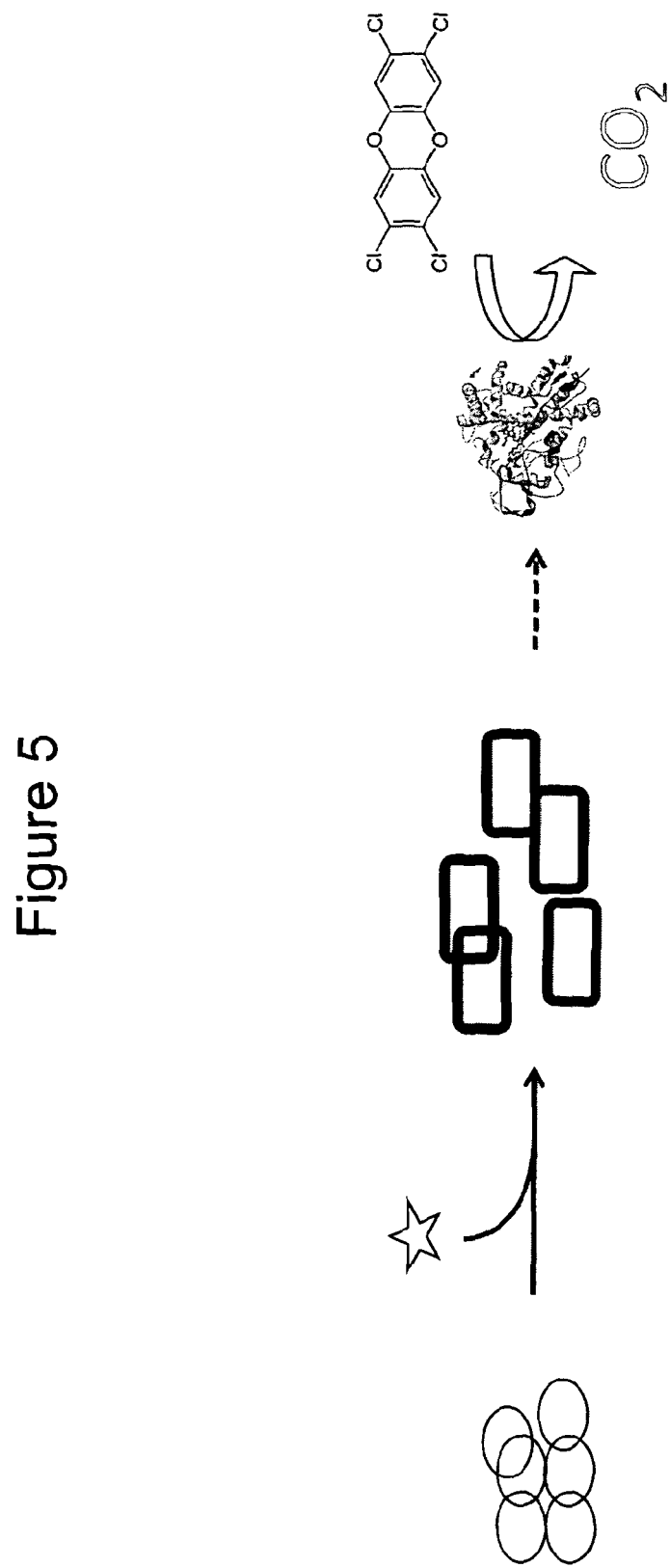
FIG. 5 is a representation of using programmed spore germination as an environmental sentinel for bioremediation.
Figure 6:
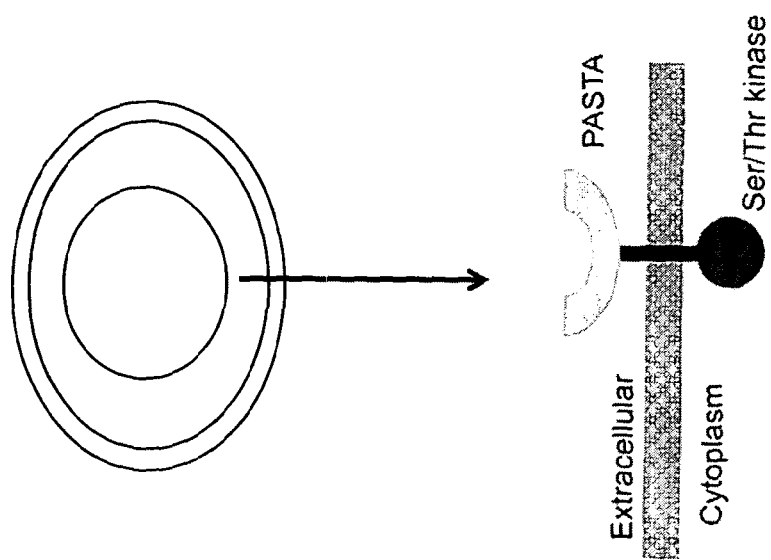

FIG. 6 is a representation of how to engineer germination receptors. prkC kinase receptors have recently been shown to bind beta-lactams and have homology to serine-threonine kinases, which dimerise to cross-phosphorylate and activate. gerA-family receptors bind germinants (such as sugars, alanine) although the mechanism of signal transduction is not clear. Modifying the extracellular (ligand binding) domain of these receptors changes the binding target of the receptors, allowing germination in response to new signals.

Figure 8:
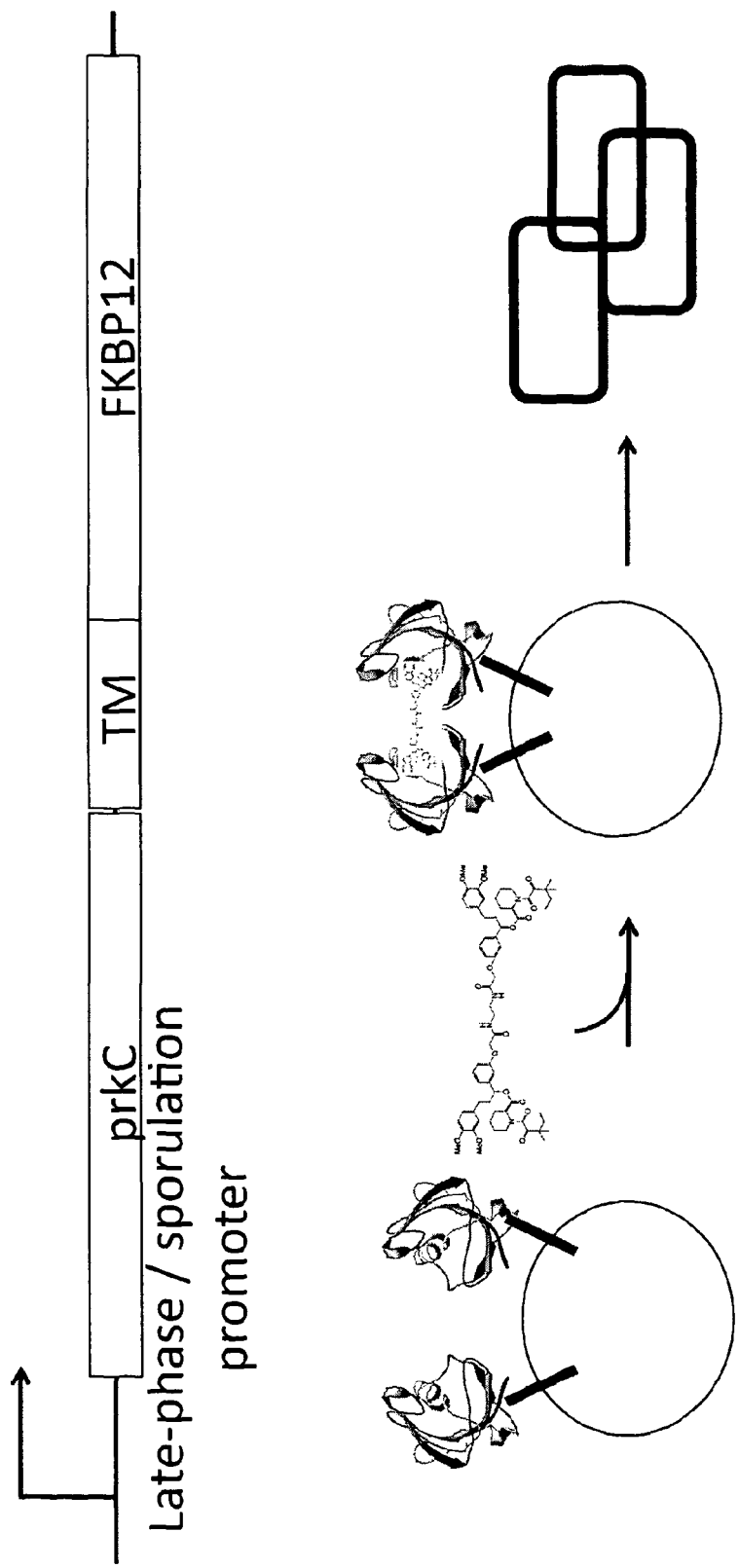

FIGS. 7 and 8 are representations of a chimeric prkC protein that has been engineered to induce germination in response to rapamycin. The murine FKBP12 domain binds rapamycin and its derivatives. Expression of a chimera with the prkC intracellular and transmembrane domain and the extracellular FKBP12 results in the stimulation of germination in the presence of rapamycin. Without wishing to be bound by any theory, the inventors consider that the rapamycin induces dimerisation of the chimeric prkC which, in turn, stimulates germination.

Figure 9:
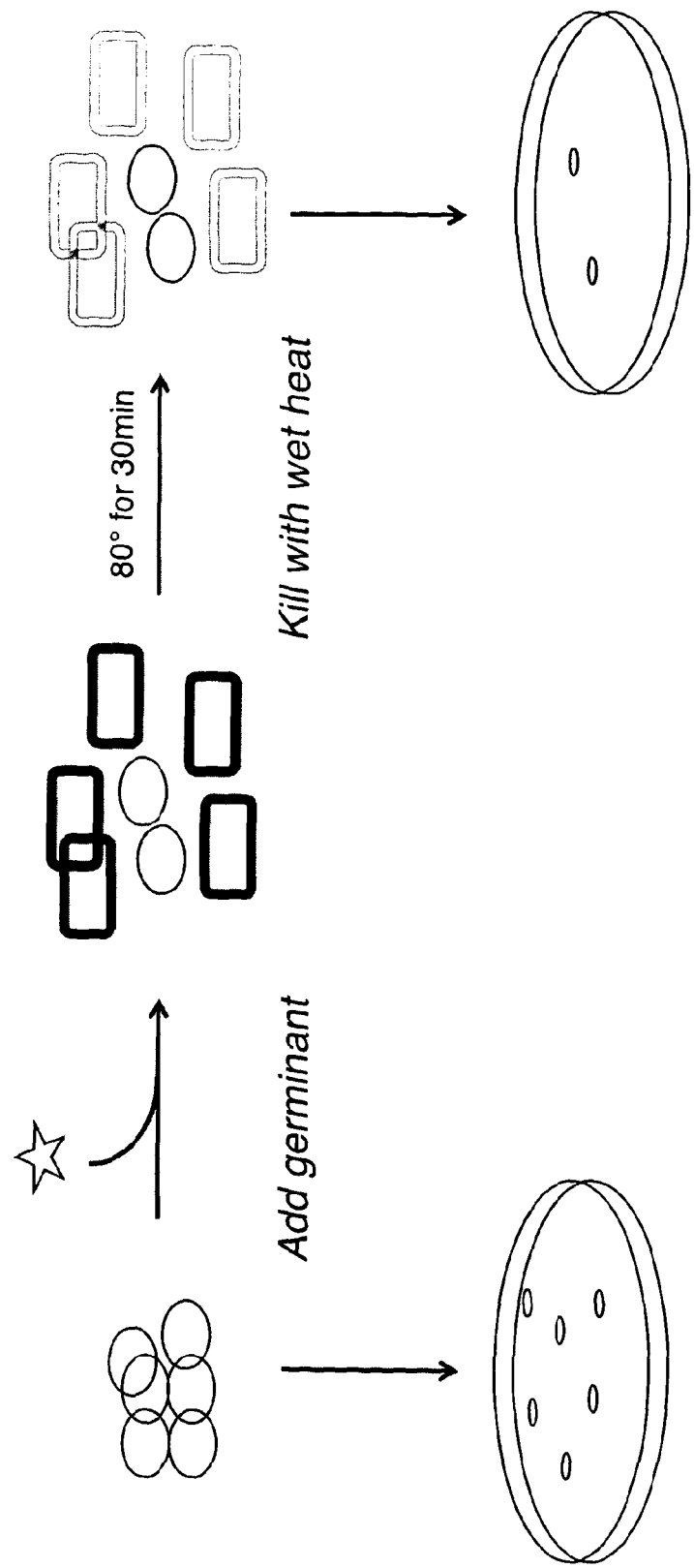

FIG. 9 is a representation of how to assay for germinating spores. Germinating spores release DPA and $Ca^{2+}$ (within minutes), become sensitive to heat, and begin metabolism and gene expression. Each of these can be used to detect germination and assess germination efficiency.

Figure 10:
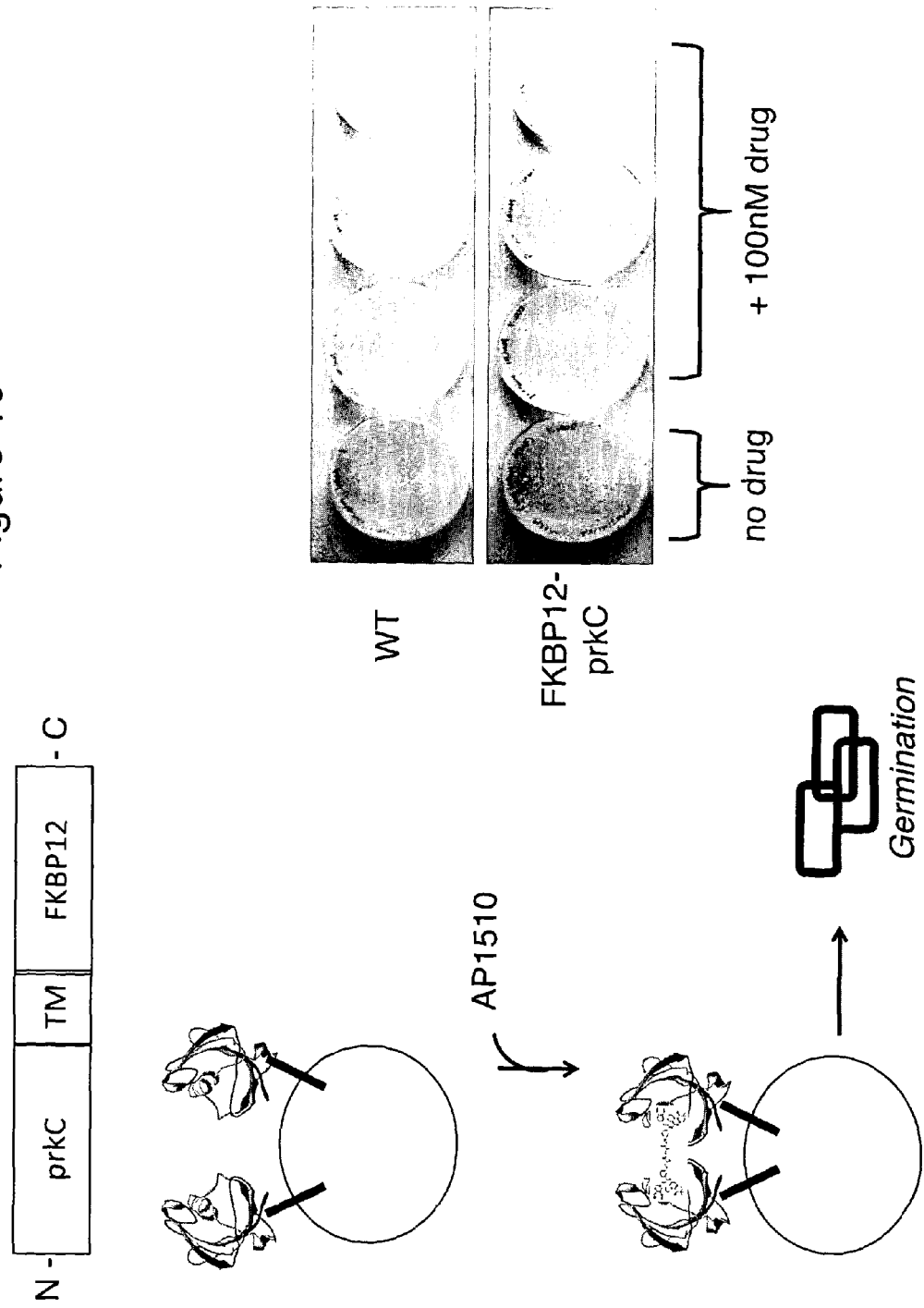
Figure 11:
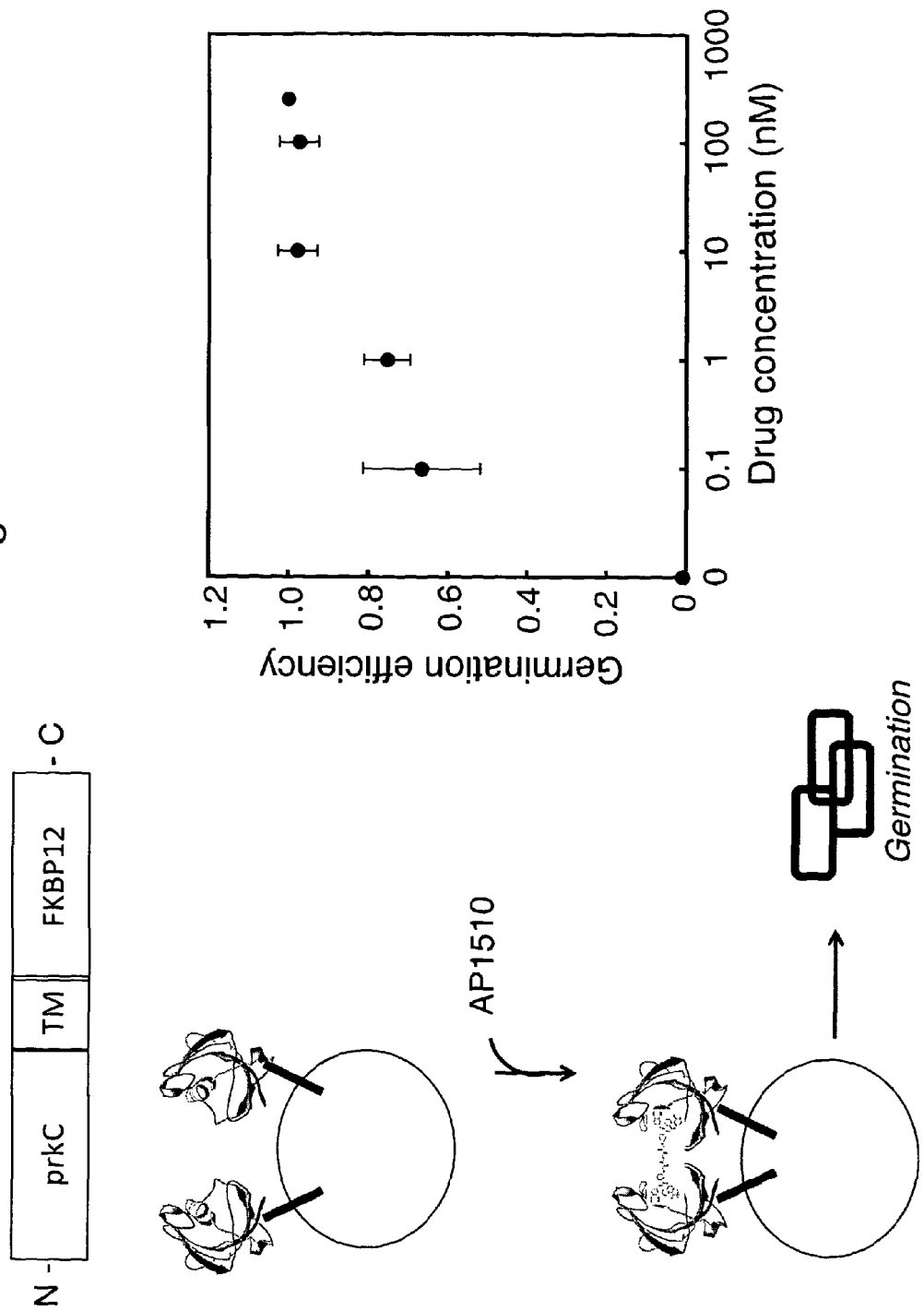

FIGS. 10 and 11 show drug induced germination in response to rapamycin in a bacterial spore with a chimeric prkC receptor.

Figure 12:
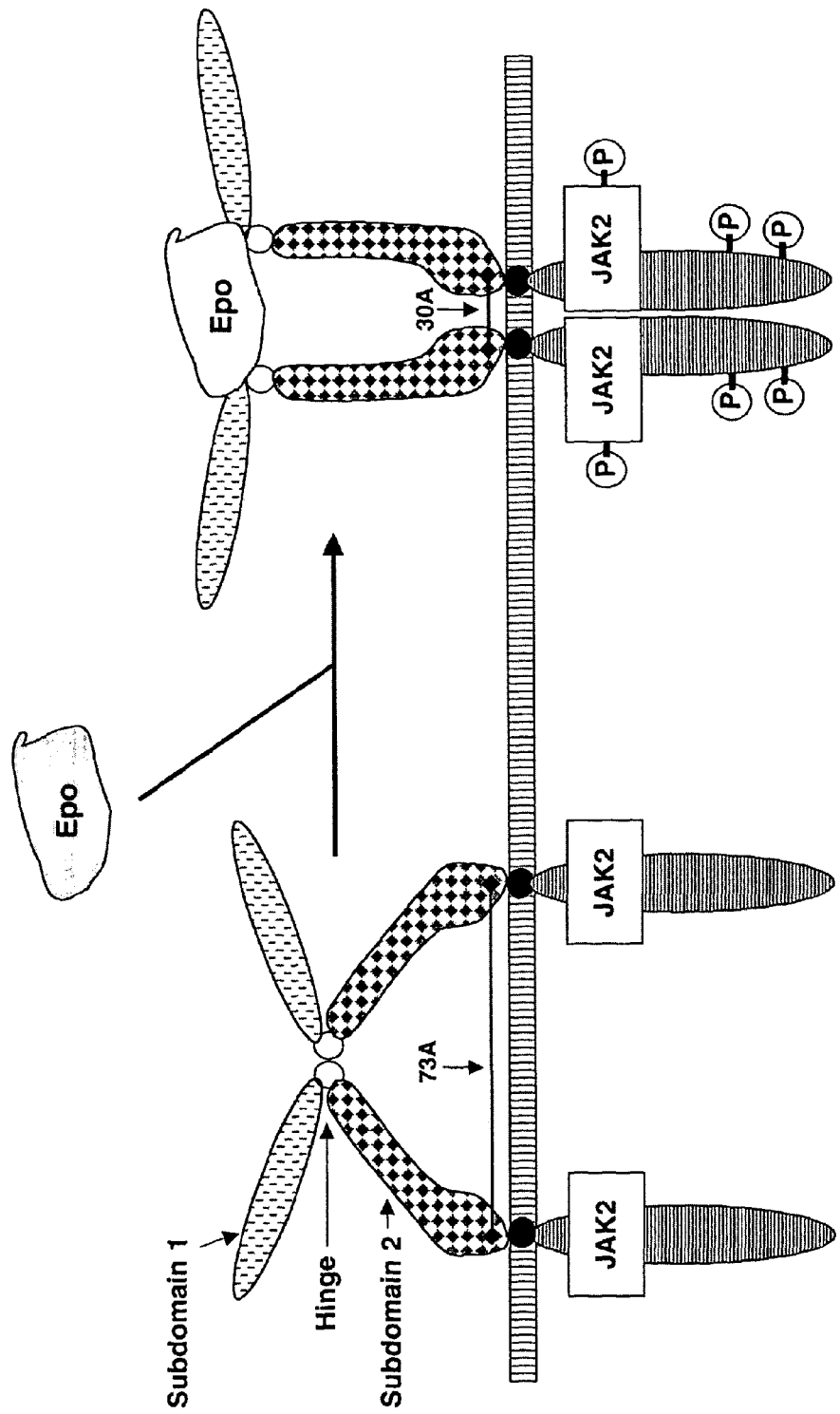

FIG. 12 is a representation of erythropoietin (EPO) receptor dimerisation in response to EPO, taken from Frank (2002). EPO promotes red blood cell proliferation and EPO receptor exists as a loose dimer, where the EPO or an EPO receptor agonist brings subunits closer together.

Figure 13:
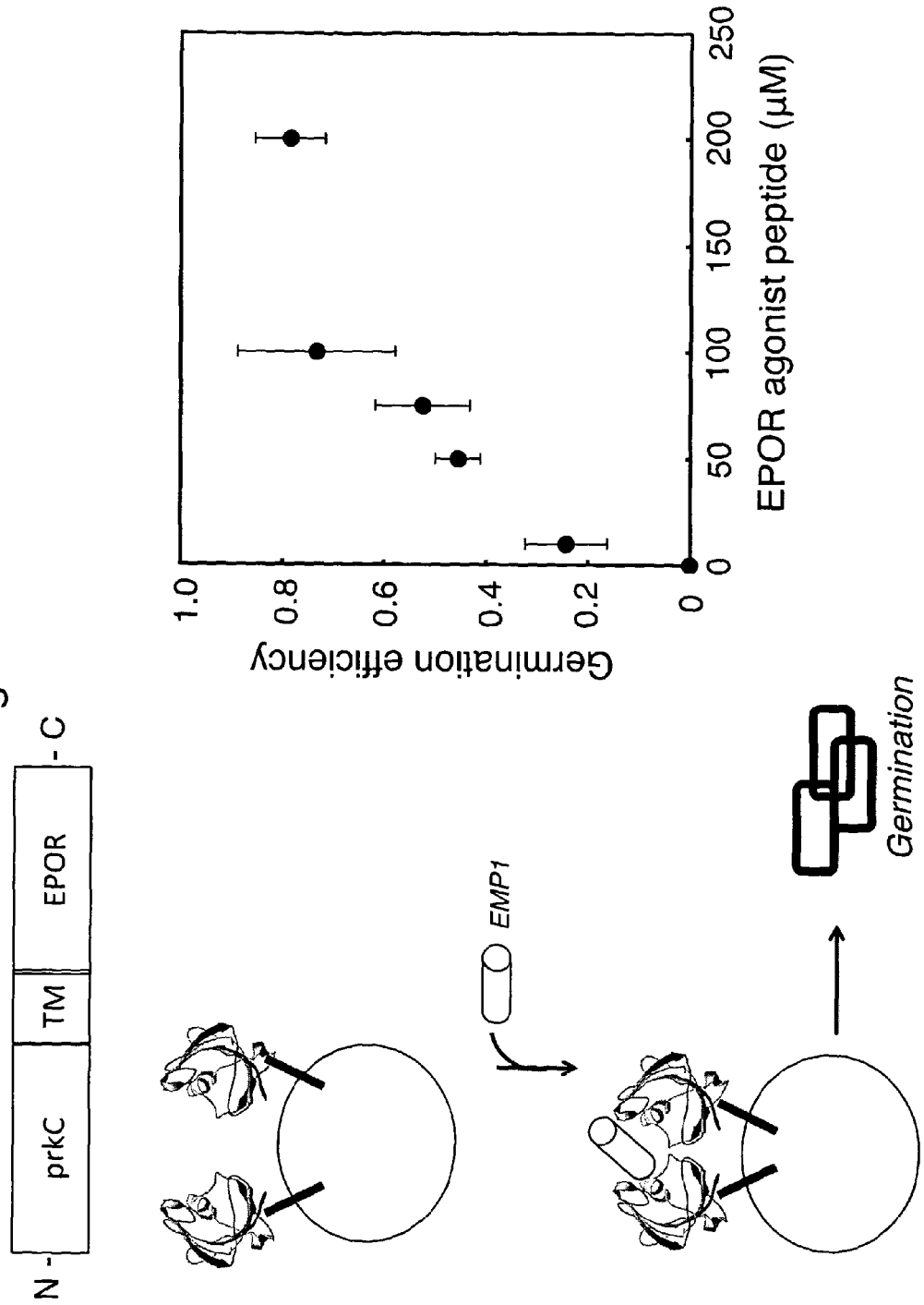

FIG. 13: Spore germination triggered by a human hormone. This figure shows EPO-induced germination of bacterial spores with a chimeric prkC receptor. Expression of a chimera with the prkC intracellular and transmembrane domain and the extracellular domain of the EPO receptor results in the stimulation of germination in the presence of EPO.

Figure 14:
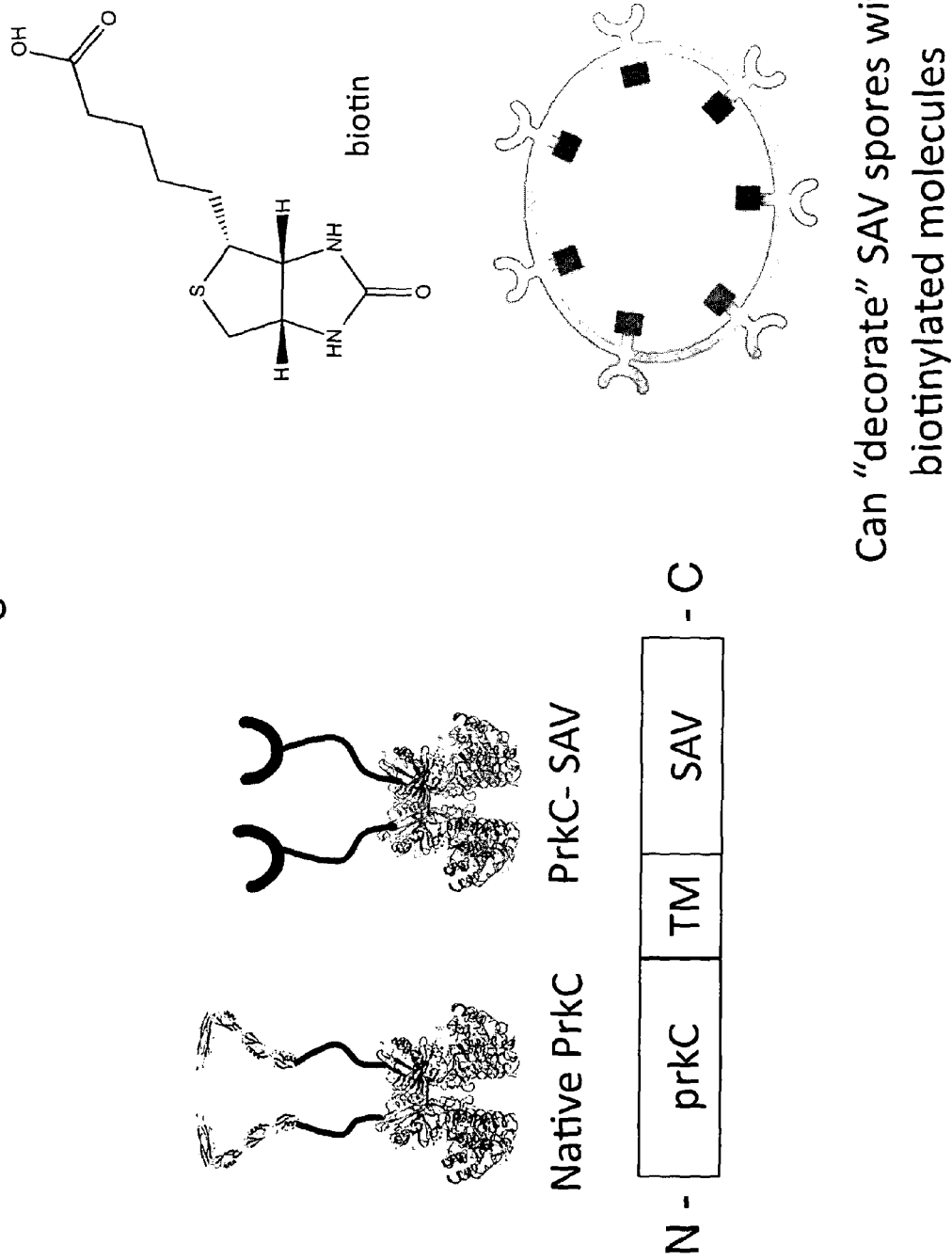

FIG. 14: Synthetic recognition elements using streptavidin. This figure is a representation of how to engineer spores that express streptavidin, and which can bind to biotinylated molecules.

Figure 15A:
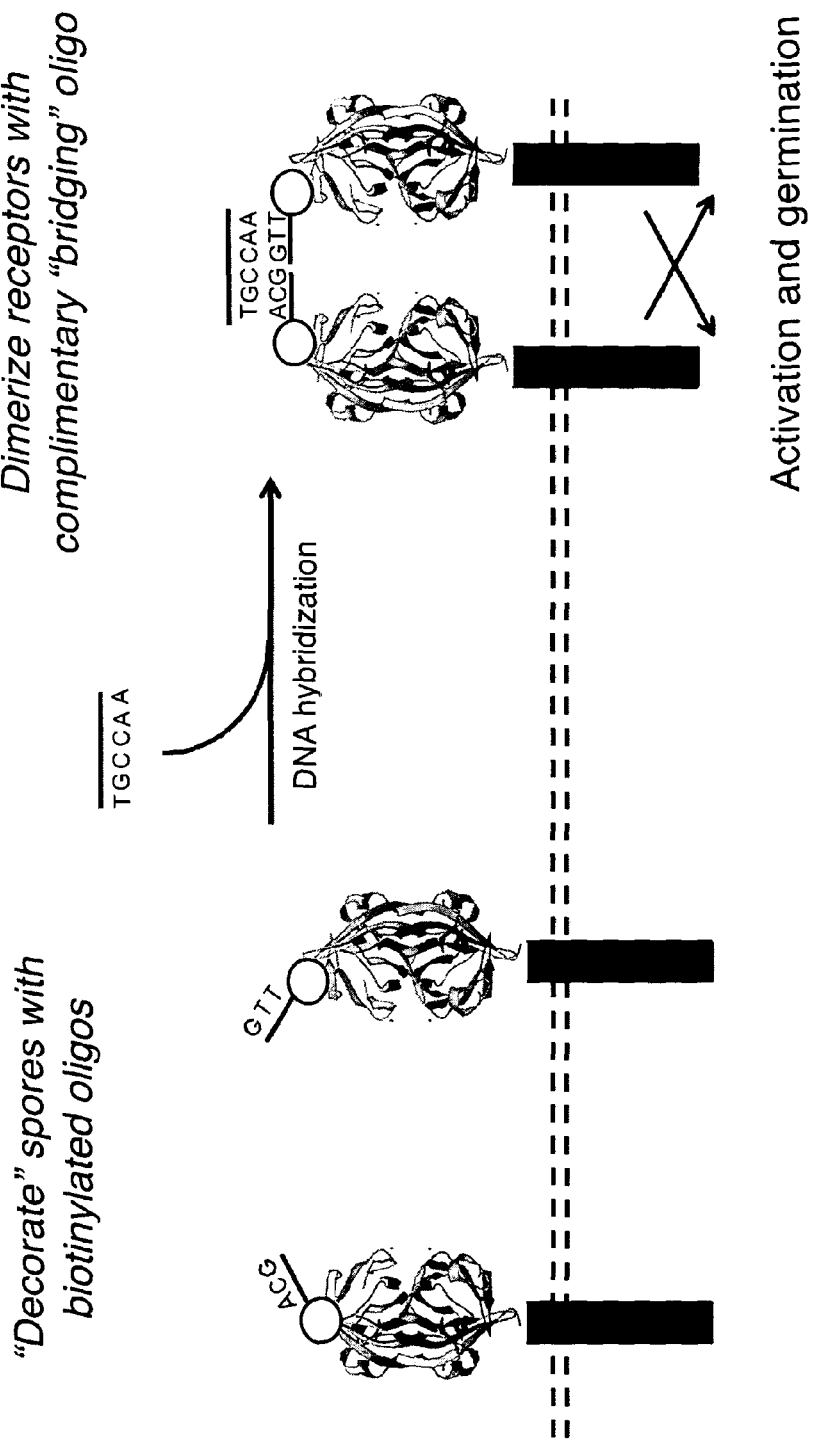
Figure 15B:
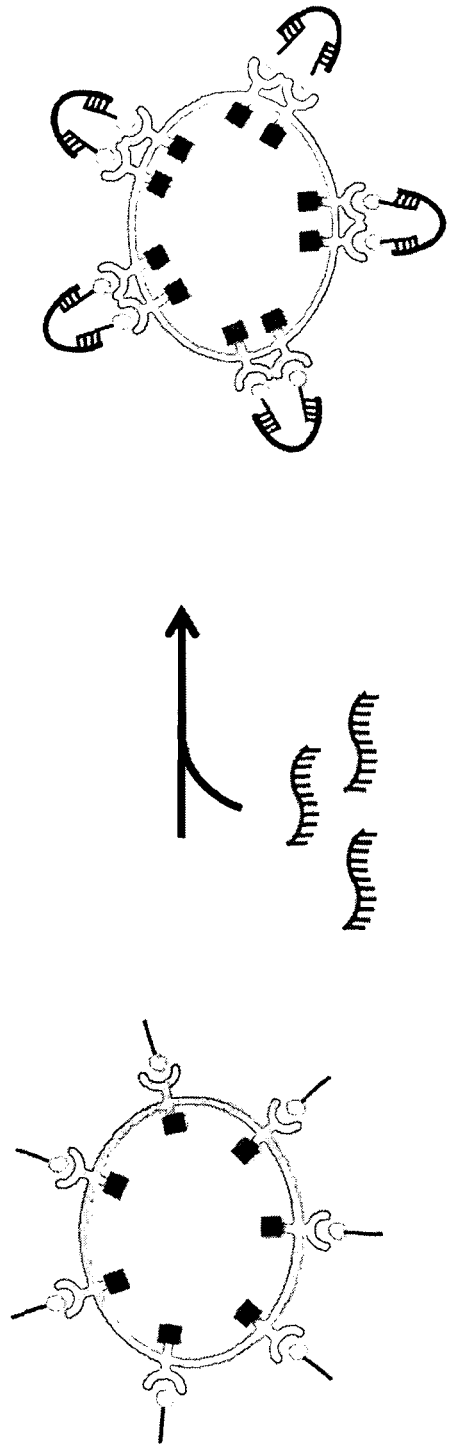

FIG. 15: Engineering synthetic nucleic acid receptors. 15(A) and (B) are representations of how to engineer spores so that they germinate in response to specific nucleic acid sequences. In (A), the two biotinylated nucleic acids 'sensors' (ACG and GTT) are complementary to the target nucleic acid sequence TGCCAA (SEQ ID NO: 22). In (B), the two biotinylated nucleic acids 'sensors' 5'-Biotin-GTGACAGGGA (SEQ ID NO: 23) and 5'-ATAAAGAGGC-Biotin (SEQ ID NO: 24) are complementary to the target nucleic acid sequence 3'-CACTGTCCCTTATTTCTCCG-5' (SEQ ID NO: 25). The target nucleic acid molecules 'bridge' the biotinylated 'sensors', causing dimerisation of the catalytic PrkC domain, and subsequent germination.

Figure 16:
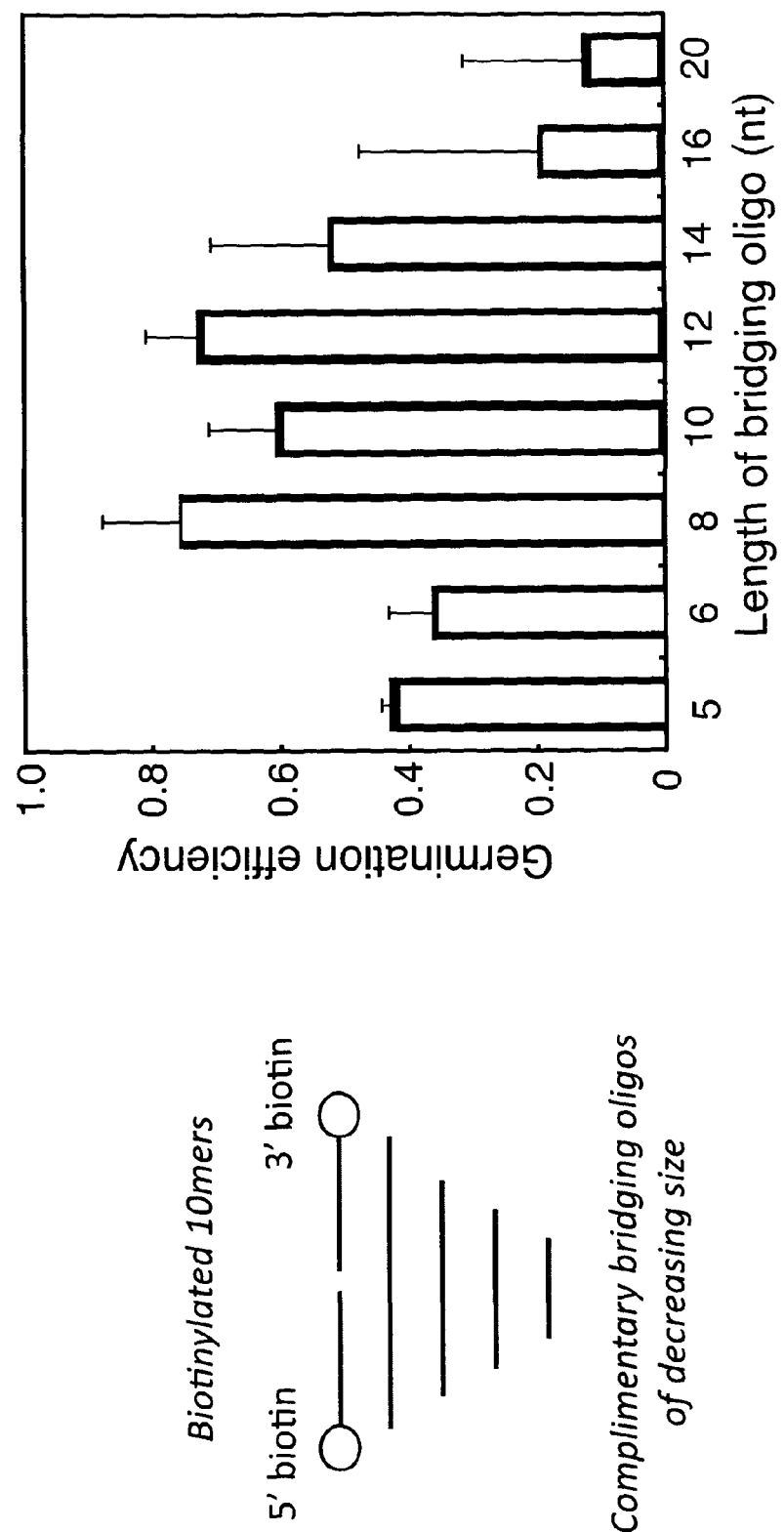

FIG. 16: Triggering germination with nucleic acid 'receptors' (I). This figure shows the efficiency of germination in response to binding oligonucleotides of varying lengths.

FIG. 17: Triggering germination with nucleic acid 'receptors' (II). (A) is a representation of the proposed mechanism of germination of prkC-SAV expressing spores with nucleic acid. Binding of the biotinylated 'sensor' nucleic acid molecules to the bridging oligos brings the prkC catalytic domains into contact. Note, the bridging nucleic acid molecule is single-stranded. (B) is a graph showing the results of a repeat assay to determine the efficiency of germination in response to binding oligos of varying lengths.

FIG. 18: This figure is a representation of how the bacterial spore coat limits entry of larger oligonucleotides, thereby lowering germination efficiency.

FIG. 19: This figure is a representation of using spore germination as a rapid biosensor. Following germination, activation and DPA-$Ca^{2+}$ release is rapid (minutes). Multiple calcium and DPA responsive dyes and fluorophores can be used to detect the DPA-$Ca^{2+}$ release. In the figures, terbium salts are used to detect DPA.

Figure 20:
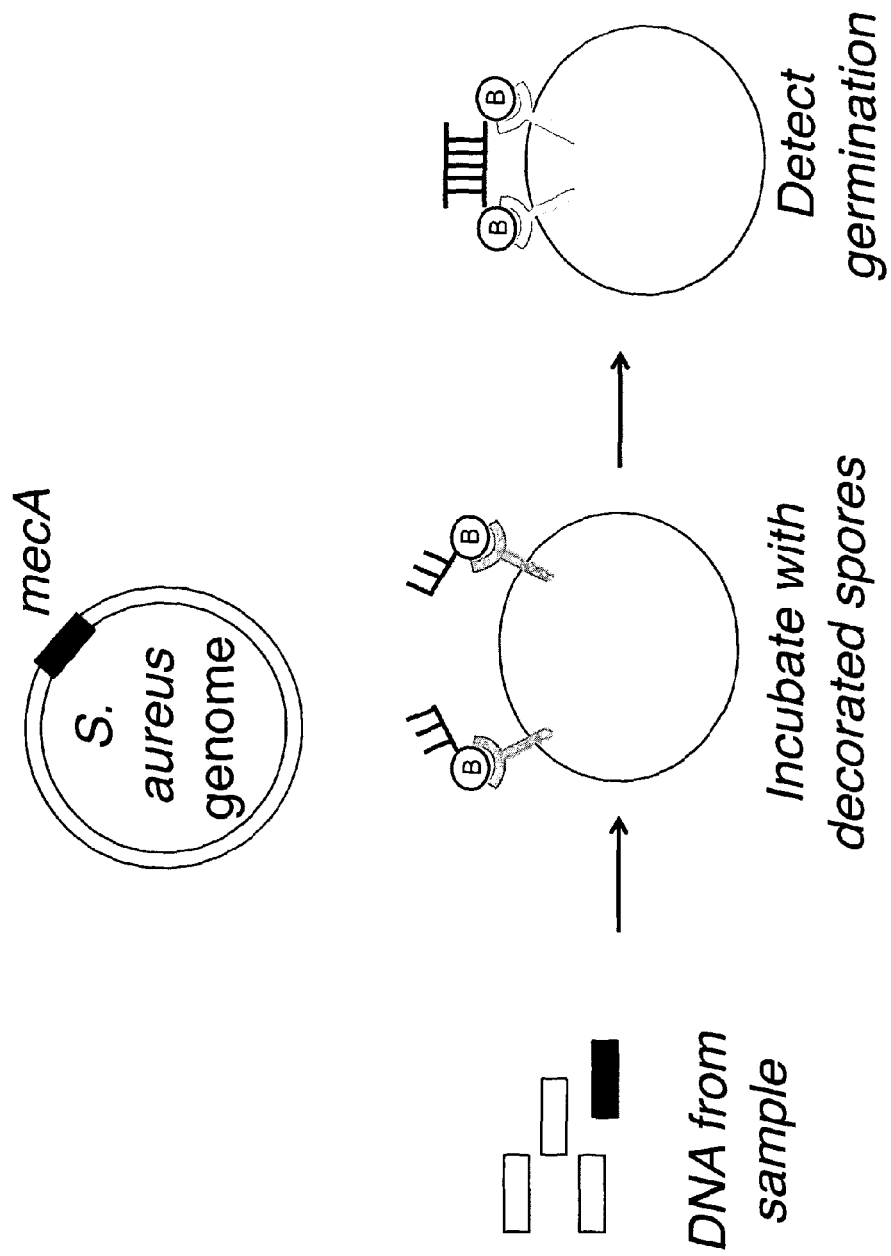

FIG. 20: This figure is a representation of the design of a rapid MRSA biosensor. Methicillin-resistant *S. aureus* (aka 'Golden Staph') is a major cause of hospital-acquired infections. Currently, detection of MRSA is culture-based or PCR-based. A germination based sensor would be far more rapid.

Figure 21:
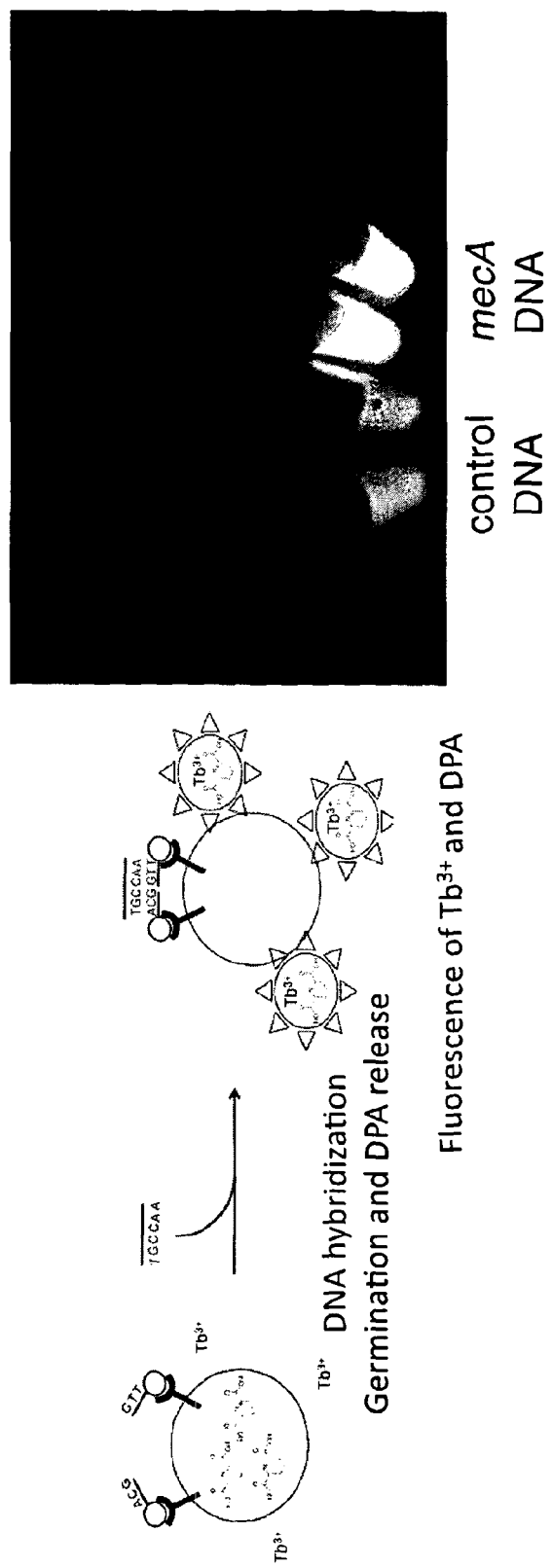

FIG. 21: This figure shows the proof of concept of a rapid sensor for the mecA gene of MRSA. Spores are decorated with α-mecA oligos, incubated with 10 nM mecA DNA for 10 min, 1 g/L of $TbCl_3$ is added, and the spores illuminated with a UV wand. Rapid detection of fluorescence greater than the control indicates presence of the mecA gene of MRSA.

Figure 22:
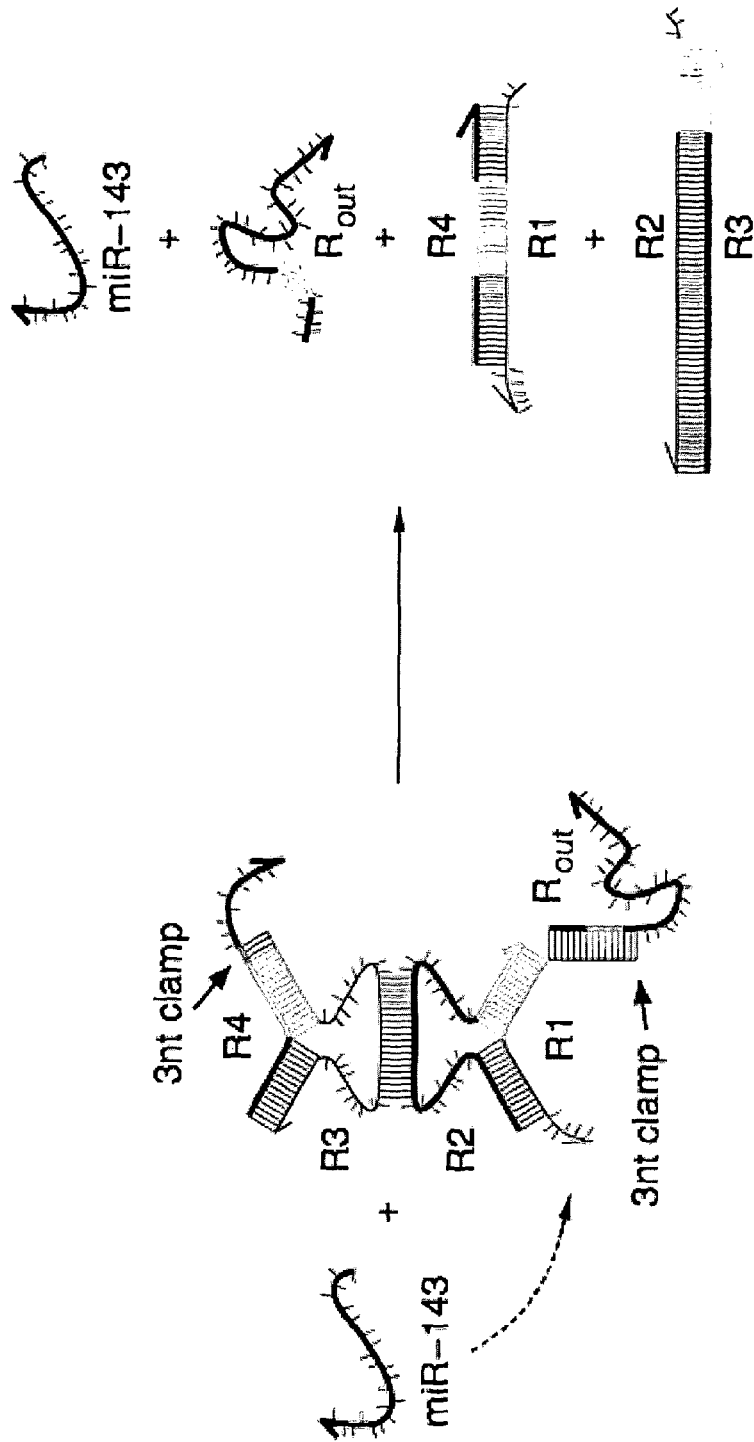

FIG. 22: Interfacing spores with DNA-based computation. This figure is a representation of an enzyme free nucleic acid amplification gate. The gate consists of nucleic acid strands R1, R2, R3 and R4 complexed with the output strand ($R_{out}$) in a metastable configuration. Upon binding of input strand miR-143 to the gate, the complex undergoes a conformational rearrangement to generate the products on the right of the arrow. $R_{out}$ is recognized by biotinylated nucleic acid sensors and the input strand is free to bind to another gate complex. (Image from supplementary data by Seelig et al, 2006).

FIGS. 23 and 24: Amplifying signals using DNA circuits. These figures show the increase in germination of prkC-SAV spores detecting output nucleic acid from logic gates designed by Seelig et al (2006).

FIG. 25: Triggering germination with covalent bond formation (I). This figure is a representation of the mechanism of click chemistry dependant germination of prkC-SAV spores. Biotinylated azide and alkyne molecules form a triazole bond in the presence of copper to bring the prkC catalytic domain in contact. Ascorbic acid reduces copper (II) sulphate to generate copper (I) since the direct use of copper (I) is not favoured.

FIG. 26: Triggering germination with covalent bond formation (II). This figure shows the click-reaction dependant germination of prkC-SAV spores. DPA release was measured using the terbium fluorescence assay. Negative controls omit either the biotinylated azide/alkyne molecules of the copper catalyst. The circles beneath the graph give a visual representation of fluorescence of the control of spores with azide/alkyne but no copper and the fully assembled click reaction with spores.

FIG. 27: Synthetic receptors using aptamers (I). This figure shows anti-PDGF aptamers (taken from Fredriksson et al, 2002) together with a representation of how biotinylated aptamers can stimulate germination of prkC-SAV spores in the presence of PDGF.

FIG. 28: Synthetic receptors using aptamers (II). This figure shows the germination of prkC-SAV spores in the presence of PDGF.

Figure 29:
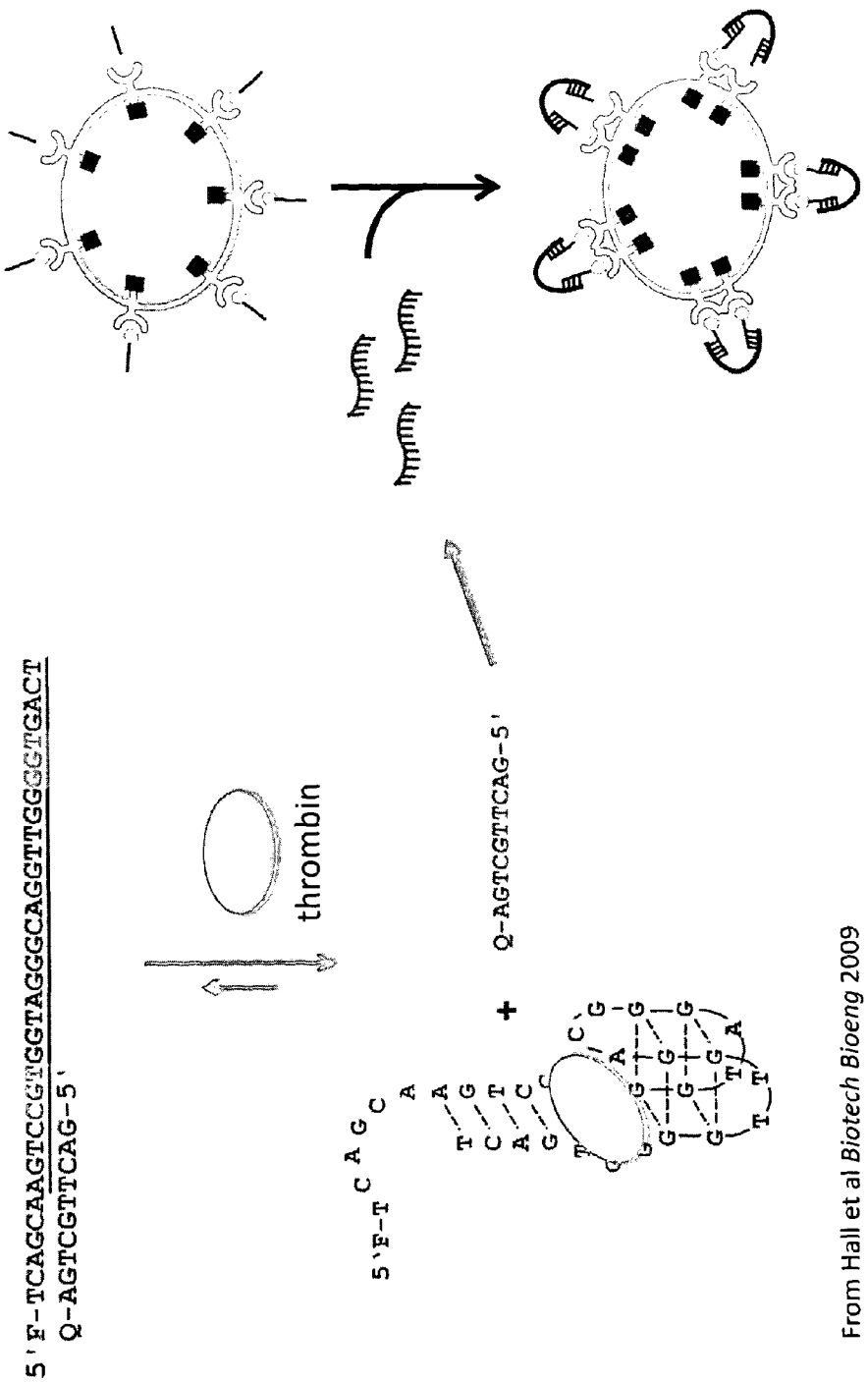

FIG. 29: Protein detection using structure-switching aptamers (I). This figure shows structure-switching anti-thrombin aptamers (taken from Hall et al, 2009), together with a representation of how they can stimulate germination of prkC-SAV spores in the presence of thrombin.

Figure 30:
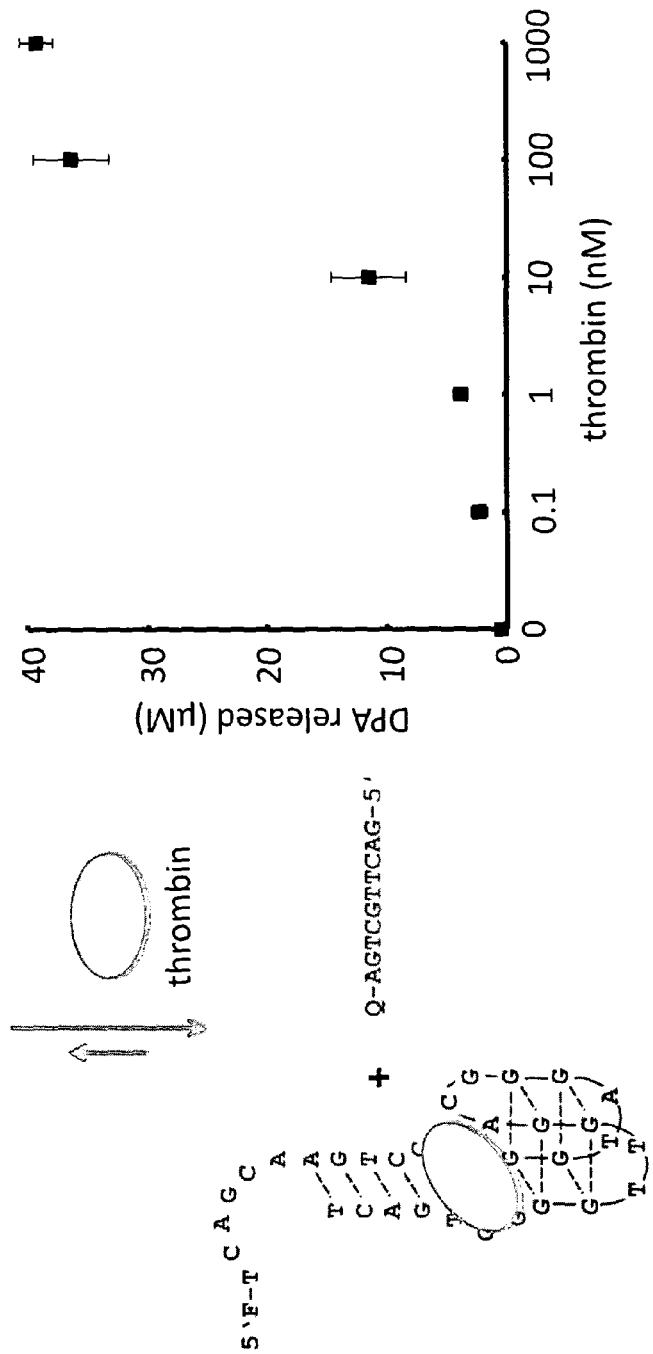

FIG. 30: Protein detection using structure-switching aptamers (II). This figure shows the germination of prkC-SAV spores in the presence of thrombin.

EXAMPLE 1

Making a Bacterial Spore that Germinates in Response to Rapamycin

Materials and Methods
Polymerase Chain Reaction

PCR reactions comprised of the following components in their final concentrations; 1× Phusion GC buffer, dNTPs 200 μM each, forward and reverse primers 0.5 μM each (sequences listed in Table 1), template DNA: ~1 ng/50 μl reaction for amplifying FKBP-1 and FRB-1, ~10 ng/50 μl reaction for amplifying DNA from cDNA FKBP-1 and FRB-1 templates, Phusion DNA polymerase 0.02 U/μl, $ddH_2O$ to make up final volume, with controls omitting DNA and replaced by $ddH_2O$ of the same volume. Phusion DNA polymerase was added to the reaction last in order to prevent degradation of DNA by the exonuclease activity of the polymerase.

PCR cycling conditions are as follows for generation of:
1) FKBP-1 and FRB-1: denaturation at 98° C. for 2 min followed by 30 cycles of denaturation at 98° C. for 30 sec, annealing at 65° C. for 30 sec, extension at 72° C. for 45 sec, final extension at 72° C. for 2 min.
2) FKBP-2 and FRB-2 (a) denaturation at 98° C. for 2 min followed by 30 cycles of denaturation at 98° C. for 30 sec, annealing at 65° C. for 30 sec, extension at 72° C. for 1 min 15 sec, final extension at 72° C. for 2 min. (b) denaturation at 98° C. for 2 min followed by 30 cycles of denaturation at 98° C. for 30 sec, annealing at 55° C. for 45 sec, extension at 72° C. for 2 min, final extension at 72° C. for 2 min.
3) FKBP and FRB with RE sites: denaturation at 98° C. for 2 min followed by 30 cycles of denaturation at 98° C. for 30 sec, annealing at 50° C. for 30 sec, extension at 72° C. for 1 min 15 sec, final extension at 72° C. for 2 min.

TABLE 1

| Primer sequences | |
|---|---|
| Oligo | Sequence 5'-3' |
| 1F | CAGCTAAACCATTTTTCGAGGTTTAAATCCTTATCGTTATGGG TATTGTTTGTAATATGCTGATCGGTAAACGTATTAG (SEQ ID NO: 2) |
| 2R | GCGGCAAAACCCCGCCGAAGCGGGGTTTTCGGCGTTATTATTC CAGTTTCAGCAGTTCC (SEQ ID NO: 3) |

TABLE 1-continued

Primer sequences

| Oligo | Sequence 5'-3' |
|---|---|
| 3F | CAGCTAAACCATTTTTCGAGGTTTAAATCCTTATCGTTATGGG TATTGTTTGTAATATGCAATCAGCCTCTTCTCTGG (SEQ ID NO: 4) |
| 4R | GCGGCAAAACCCCGCCGAAGCGGGGTTTTCGGCGTTATCATTG TTTGCTGATACGGC (SEQ ID NO: 5) |
| 5F | GATTCGTTTTACTTTCCCGTTCTCTCTGATTGTGAAATTGCAG CTAAACCATTTTTCGAGGT (SEQ ID NO: 6) |
| 6R | CTTGGAGGCTATTACGATGTTGGTAAAACTCAGGAACAAGGCG GCAAAACCCCGC (SEQ ID NO: 7) |
| 7F | CTTGTTCCTGAGTTTTACCAACATCGTAATAGCCTCCAAGCAG CTAAACCATTTTTCGAGG (SEQ ID NO: 8) |
| 8R | AGGTCGACTCTAGAGGATCCCCGGGTACCGAGCTCGAATTGCG GCAAAACCCCG (SEQ ID NO: 9) |
| 9F (SacI) | AAGAGCTCCAGCTAAACCATTTTTCGAGGT (SEQ ID NO: 10) |
| 10R (PstI) | AACTGCAGGCGGCAAAACCCCG (SEQ ID NO: 11) |

Annealing reaction of FKBP-2 and FRB-2 to check for overlapping regions; PCR components added in concentrations previously described with no primers and FKBP-2 and FRB-2 at 10 ng each/50 µl reaction. Thermocyler conditions; denaturation at 98° C. for 2 mins, followed by 60 cycles of denaturation at 98° C. for 30 secs, annealing at 55° C. for 30 secs, extension at 72° C. for 30 secs, and final extension at 72° C. for 2 minutes.

PCR reactions were purified by gel extraction, Qiagen, and eluted in TE buffer for subsequent use in DNA ligation reactions.

Restriction Enzyme Digest, DNA Ligation and Transformation into E. Coli

Restriction enzyme digests were set up in the following concentrations:

1× buffer as chosen for digest, 1×BSA (if required), 1-2 mg DNA, 1 µl of enzyme, ddH$_2$O to final volume of 50 µl. Incubation at 37° C. for ~3 hrs. For diagnostic digests for screening of transformants, 5 µl of 'miniprepped' plasmid was incubated 25 µl total for 1 hour as it is not necessary for the reaction to proceed to completion.

Plasmid pNW33N was purified from 20 ml overnight culture of E. coli grown in LB supplemented with 25 µg/ml chloramphenicol (CAM) at 37° C., using Midiprep Kit, Qiagen. Synthesised prkC-FKBP and prkC-SAV fusions (GeneArt) were amplified by PCR, adding the sporulation induced promoter ctc and terminator on forward and reverse primers respectively. Restrictions sites were added to these genes by a subsequent PCR reaction to add SacI and KpnI recognition sequences. Purified PCR products and pNW33N were digested with SacI and PstI (NEB) as described above. Ligation of prkC-FKBP gene and pNW33N was set up in the following components for incubation at room temperature for 1 hour 30 mins; 3:1 molar ratio of insert:vector, 0.5 µl T4 DNA ligase (400,000 U/ml), 1 µl 10× T4 DNA ligase buffer, ddH$_2$O to make up final volume to 10 µl. 3-5 µl of ligation reaction were transformed into chemically competent E. coli cells. In brief, plasmid DNA was added to 50 µl of competent cells and placed on ice for 30 mins and heat shocked at 42° C. in a water bath for 30 secs. Reactions were placed on ice for 4-5 mins before addition of 8000 of room temperature LB and incubated at 37° C. with shaking for 45 mins. Cells were concentrated by centrifugation at 9000 rpm for 30 sec and resuspended in 100 µl of the supernatant. PrkC-SAV ligations were transformed into BL21 (DE3) gold competent cells (Stratagene) by chemical transformation following the manufacturers instructions. Cells were spread onto LB agar plates supplemented with 25 µg/ml CAM for selection at 37° C. for ~16 hrs.

Preparation of Competent Cells and Transformation in Bacillus subtilis

Transformation in B. subtilis was achieved by utilising the natural competency of these cells, using the two-step transformation procedure (Cutting and Vander Horn, 1990). In brief, overnight cell growth from a freshly streaked LB plate incubated at 37° C. was used to inoculate 20 ml of pre-warmed SpC medium to give an OD$_{600}$ of approximately 0.5. The culture was incubated at 37° C. with vigorous aeration (225 rpm) and cell growth monitored by periodic OD$_{600}$ measurements. When no significant change in cell density was observed (seen at 2.5-3.0), 2 ml of stationary-phase culture was used to inoculate 200 ml of pre-warmed SpII medium. The culture was incubated at 37° C. at 150 rpm for 90 minutes before pelleting the cells by centrifugation (4000 rpm, 15 minutes) at room temperature in 6×50 ml falcon tubes. The supernatant was decanted into a sterile container and used to resuspend the cell pellets (18 ml). 2 ml of sterile glycerol was gently mixed to the competent cells and aliquoted into 0.5 ml Eppendorf tubes before rapid freezing in dry ice. Competent cells were stored at −80° C.

For transformation, competent cells were rapidly thawed by immersing frozen tubes in a 37° C. water bath. Cells were aliquoted into 200 µl samples to which 200 µl of SpII and EGTA were added. Each 400 µl mixture was separated back into 200 µl samples with recombinant plasmid added to each sample (between 500 ng-1 µg miniprepped DNA from E. coli). Samples were incubated at 37° C. at 200 rpm for 30 minutes before adding 20 µl of T-base and 2 µl of 5% glucose solution. Samples were plated on LB agar with chloramphenicol (CAM) at a concentration of 15 µg/ml and incubated overnight at 37° C. The optimal concentration of CAM for selectivity was determined experimentally by transforming competent cells with ddH$_2$O and plating on LB agar with CAM concentrations of 5 µg/ml, 10 µg/ml, 15 µg/ml and 20 µg/ml.

Sporulation in Bacillus subtilis

B. subtilis sporulation was induced by growth to exhaustion in Difco Sporulation Media (DSM) as outlined in the method by Nicholson and Setlow (1990). Sporulating cultures at t$_{48}$ hrs were harvested by centrifugation (10,000 g 10 min, 4° C.) and purified by lysozyme treatment and salt detergent washes. Pellets were washed in 0.5M NaCl and incubated at 37° C. for 1 hr in Tris.Cl (50 mM, pH 7.2) containing lysozyme at 50 µg/ml. Spores were then subjected to alternate rounds of centrifugation (10,000 g, 10 min) and washing with: NaCl, deionised water, 0.05% SDS solution, TEP buffer (50 mM Tris.Cl, pH 7.2, containing 10 mM EDTA and 2 mM phenylmethylsulfonyl fluoride) and three washes with deionised water.

Spores were stored in deionised water at 4° C. and protected from light. Spores were maintained in these conditions by periodically centrifuging (10,000 g, 10 min) and resuspending in cold deionised water once a week.

Measurement of Germination: Loss of Heat Resistance Assay

The germination assay designed here is based on the method described in Shah et al. (2008) and modified for the purpose of this study. Spores of B. subtilis WT and pNW33N/

FKBP were incubated at approximately 2×10⁷ (OD₅₈₀ ~0.3) in 10 mM Tris.Cl, pH8 in 100 µl reactions with the germinant AP1510 for 1 hour at 37° C. and subjected to wet heat, 75° C. for 30 min. A negative control of spores with pNW33N/FKBP were incubated with 10 mM Tris.Cl pH8 at a volume corresponding to 10 nM AP1510. For testing oligo induced germination, 100 µl reactions with 100 nM of biotinylated 'sensors' were incubated with PrkC-SAV spores at room temperature for 15 min. Reactions were spun at 4000 rpm for 1 min and resuspended in deionized dH20 with 10 µM of bridging oligo or 1 hour at room temperature. Negative controls consisted of spores incubated with oligo but no biotinylated sensors, and spores incubated with water. In both experiments, spores were then subjected to wet heat (80° C.) for 30 min. Heat-treated and ungerminated samples were serially diluted and 10 µl of 10³-10⁵ dilutions were spread onto LB-agar plates for overnight incubation at 30° C. For any given AP1510 concentration tested, reactions were set up in triplicate. Percentage of germination was measured by observation of the number of colonies between germinated and ungerminated plates. The mean number of colonies between triplicate reactions was calculated and used to measure the percentage of germination in comparison with the number of colonies observed on ungerminated agar plates for the same dilution.

Measurement of Germination: DPA Release by Spectrophotometry

Reactions were set up for germination with a germinant (e.g., AP1510) as described in 'Loss of Heat Resistance' assay but incubated at room temperature with an immediate reading taken following addition of germinant. For each reading, 10 µl of reaction was removed and spores pelleted by centrifugation. The concentration of DPA in the extracellular media was measured at 270 nm on Nanodrop (Thermo Scientific). At least two repeats were performed for each concentration and DPA release was expressed as an average of Abs—initial Abs for each time point.

Measurement of Germination: DPA Release by Terbium (III): DPA Fluorescence Complex Germination reactions set up as described in 'Loss of Heat Resistance' for germination using a germinant (e.g., AP1510) and bridging oligos. For all PrkC-SAV spore reactions, 100 nM of biotinylated 'sensor' was added to 100 µl reactions of spores at a concentration of OD₆₀₀ ~1. Spores were spun briefly and resuspended in ddH20 either with 100 nM of copper (II) sulfate catalyst and reductant ascorbic acid for click reactions, or 100 nM of input nucleic acid and 1 µM of 'gate complex' for germination detecting output nucleic acid from signal amplification. Gate nucleic strands were denatured at 90° C. for 5 minutes and annealed by slow cooling to room temperature for assemble the complex before addition to spores. All reactions were carried out at room temperature. Controls for PrkC-SAV spore experiments omitted each reagent/parameter tested and the affect on germination was assessed. After addition of germinant, terbium was added to a final concentration of 5 µM and fluorescence visualized on a UV transilluminator (Biorad), at periodic time points. A DPA standard was imaged using known concentrations and correlated to fluorescent pixels.

Flow Cytometry

Flow cytometry was performed using a FACS Calibur flow cytometer with operating software CellQuest (both BD Biosciences). Spores were suspended in 1 ml reactions at OD₆₀₀≈0.1 with germinant (e.g., 10 mM L-alanine or AP1510) and 0.5 µM SYTO-16 (Invitrogen). The maximal value for the fluorescence emission of SYTO 16 complex with DNA is observed at 518 nm. Reactions were incubated in the dark at 37° C. and 200 µl were removed was diluted in 1 ml with deionized dH20 at periodic time intervals. Data acquisition was set to 50,000 events, at a nominal flow rate of 1000-2000 events per sec using laser setting E-01 and side-scatter threshold adjusted to 100 mV to select for spore populations. The green emission from SYTO 16-staining is indicative of cortex hydrolysis.

Generation of Chimeric Construct

A chimeric protein containing the *B. subtilis* prkC intracellular and transmembrane domains, and the murine FKBP12 extracellular domain, as shown in FIGS. 7 and 8, was made using standard molecular biology techniques (see, for example, Molecular Cloning: a Laboratory Manual: 3rd edition, Sambrook and Russell, 2001, Cold Spring Harbor Laboratory Press) and as described above.

The sequence of the prkC-FKBP12 fusion protein was:

```
                                        (SEQ ID NO: 12)
MLIGKRISGRYQILRVIGGGGMANVYLAEDIILDREVAIKILRFDYAND

NEFIRRFRREAQSASSLDHPNIVSIYDLGEEDDIYYIVMEYVEGMTLKE

YITANGPLHPKEALNIMEQIVSAIAHAHQNQIVHRDIKPHNILIDHMGN

IKVTDFGIATALSSTTITHTNSVLGSVHYLSPEQARGGLATKKSDIYAL

GIVLFELLTGRIPFDGESAVSIALKHLQAETPSAKRWNPSVPQSVENII

LKATAKDPFHRYETAEDMEADIKTAFDADRLNEKRFTIQEDEEMTKAIP

IIKDEELAKAAGEKEAEVTTAQENKTKKNGKRKKWPWVLLTICLVFITA

GILAVTVFPSLFMAGGSEGGGSEMGVQVETISPGDGRTFPKRGQTCVVH

YTGMLEDGKKFDSSRDRNKPFKFTLGKQEVIRGWEEGVAQMSVGQRAKL

IISSDYAYGATGHPGIIPPHATLVFDVELLKLE**.
```

Of these, residues 1-356 represent the intracellular domain of prkC; residues 357-366 represent the transmembrane domain of prkC (underlined), and the subsequent residues are the extracellular FKBP12 sequence.

Results

Expression of a chimera with the prkC intracellular and transmembrane domain and the extracellular FKBP12 domain in a bacterial spore results in the stimulation of germination in the presence of rapamycin. Rapamycin does not stimulate the germination of the bacterial spores in the absence of the chimeric protein. FIG. 10 shows drug induced germination in response to rapamycin in a bacterial spore with the chimeric prkC receptor. FIG. 11 shows the increase in germination efficiency of bacterial spores with increased concentration of rapamycin.

Discussion

As far as the inventors are aware, this is the first time that anyone has shown that bacterial spores can be engineered to germinate in response to a desired chemical agent that does not stimulate germination of an otherwise equivalent unmodified bacterial spore.

EXAMPLE 2

Making a Bacterial Spore that Germinates in Response to Erythropoietin

Methods

A chimeric protein containing the *B. subtilis* prkC intracellular and transmembrane domains, and the human erythropoietin (EPO) receptor (EPOR) extracellular domain, as shown in FIG. 13, was made using standard molecular biology techniques and expressed on *B. subtilis* bacterial spores as described above.

The sequence of the prkC-EPOR fusion protein was:

(SEQ ID NO: 13)
```
MLIGKRISGR YQILRVIGGG GMANVYLAED IILDREVAIK
ILRFDYANDN EFIRRFRREA QSASSLDHPN IVSIYDLGEE
DDIYYIVMEY VEGMTLKEYI TANGPLHPKE ALNIMEQIVS
AIAHAHQNQI VHRDIKPHNI LIDHMGNIKV TDFGIATALS
STTITHTNSV LGSVHYLSPE QARGGLATKK SDIYALGIVL
FELLTGRIPF DGESAVSIAL KHLQAETPSA KRWNPSVPQS
VENIILKATA KDPFHRYETA EDMEADIKTA FDADRLNEKR
FTIQEDEEMT KAIPIIKDEE LAKAAGEKEA EVTTAQENKT
KKNGKRKKWP WVLLTICLVF ITAGILAVTV FPSLFM
AGGSEGGGSE APPPNL
PDPKFESKAA LLAARGPEEL LCFTERLEDL VCFWEEAASA
GVGPGNYSFS YQLEDEPWKL CRLHQAPTAR GAVRFWCSLP
TADTSSFVPL ELRVTAASGA PRYHRVIHIN EVVLLDAPVG
LVARLADESG HVVLRWLPPP ETPMTSHIRY EVDVSAGNGA
GSVQRVEILE GRTECVLSNL RGRTRYTFAV RARMAEPSFG
GFWSAWSEPV SLLTPSDLDP
```

Of these, residues 1-356 represent the intracellular domain of prkC; residues 357-366 represent the transmembrane domain of prkC (underlined), and the last 226 residues are the extracellular EPOR sequence.

Results

Expression of a chimera with the prkC intracellular and transmembrane domain and the extracellular EPOR domain in a bacterial spore results in the stimulation of germination in the presence of EPO. EPO does not stimulate the germination of the bacterial spores in the absence of the chimeric protein. FIG. 13 shows the increase in germination efficiency of bacterial spores with increased concentration of EPO.

Discussion

This is a further example of bacterial spores that have been engineered to germinate in response to a desired chemical agent that does not stimulate germination of an otherwise equivalent unmodified bacterial spore.

EXAMPLE 3

Making a Bacterial Spore that Germinates in Response to DNA

Methods

A prkC-streptavidin fusion protein (prkC-SAV) was prepared as shown in FIG. 14, and expressed on *Bacillus* spores.

The sequence of the prkC-streptavidin fusion protein was:

(SEQ ID NO: 14)

```
MLIGKRISGR YQILRVIGGG GMANVYLAED IILDREVAIK
ILRFDYANDN EFIRRFRREA QSASSLDHPN IVSIYDLGEE
DDIYYIVMEY VEGMTLKEYI TANGPLHPKE ALNIMEQIVS
AIAHAHQNQI VHRDIKPHNI LIDHMGNIKV TDFGIATALS
```

-continued

```
STTITHTNSV LGSVHYLSPE QARGGLATKK SDIYALGIVL
FELLTGRIPF DGESAVSIAL KHLQAETPSA KRWNPSVPQS
VENIILKATA KDPFHRYETA EDMEADIKTA FDADRLNEKR
FTIQEDEEMT KAIPIIKDEE LAKAAGEKEA EVTTAQENKT
KKNGKRKKWP WVLLTICLVF ITAGILAVTV FPSLFM
AGGSEGGGSE
MAEAGITGTWYNQLGSTFIVTAGADGALTGTYESAVGNAESRYT
LTGRYDSAPATDGSGTALGWRVAWKNNYRNAHSATTWSGQYVGG
AEARINTQWTLTSGTTEANAWKSTLRGHDTFTKVKPSAASI
```

Of these, residues 1-356 represent the intracellular domain of prkC; residues 357-366 represent the transmembrane domain of prkC (underlined), and the last 129 residues are the streptavidin sequence for binding biotinylated compounds to the spore surface.

Two short biotinylated DNA sequences were attached to the *B. subtilis* prkC-streptavidin chimeric protein on bacterial spores using standard molecular biology techniques. The spores were incubated in the presence of an oligonucleotide that was complementary to both of the attached DNA sequences (a 'bridging oligo'), as shown schematically in FIG. 15, allowed to germinate, and the efficiency of germination was measured.

The optimal 'bridging' oligo length required for germination was measured by determining DPA release from germinating spores by fluorescence, using terbium to chelate DPA which can be detected upon UV illumination. DPA release was quantified against a standard DPA reference in which the illuminator quantifies the number of fluorescent pixels associated with DPA concentration. Germination of PrkC-SAV by target nucleic acid was also assayed by loss of heat resistance and confirmed the DPA observations with very good correlation (data not shown).

Results

Incubation of the bacterial spores with the attached DNA sequences, in the presence of the bridging oligo, resulted in the stimulation of germination. As shown in FIG. 16, the efficiency of germination related to the length of the exogenous bridging oligo. Germination was induced with bridging oligos ranging in size from 5 to 20 nucleotides, but a length of 8 to 12 or 8 to 14 oligonucleotides for the bridging oligo was found to be optimal. As shown in FIG. 18, the presence of the spore coat limits the entry of larger oligos, thus reducing the germination efficiency.

Discussion

This is a further example of bacterial spores that have been engineered to germinate in response to a desired chemical agent that does not stimulate germination of an otherwise equivalent unmodified bacterial spore. The germination was stimulated by the use of a bridging oligo to dimerise the prkC receptors, but other means for inducing dimerisation would be similarly applicable as demonstrated in Examples 5 and 6.

In the first instance, we tested whether PrkC-SAV spores could detect nucleic acid and therefore have the potential to serve as biosensors of pathogens with nucleic acid biomarkers. The mechanism by which we investigated this possibility was to design biotinylated nucleic acids 'sensors' with complementary bases to a particular target nucleic acid sequence that could 'bridge' the biotinylated 'sensors', causing dimerisation of the catalytic PrkC domain (FIG. 15).

Our results show that PrkC-SAV expressing spores can be induced to germinate via this proposed mechanism in response to nucleic acid. Germination increases with increasing bridging oligo length i.e. from 5 bp to approximately 14 bp, with germination efficiency decreasing from 14 bp to 20 bp (FIGS. 16-17).

Therefore, we may propose that this system has two opposing pressures affecting germination. On one hand, detection of nucleic acid may require longer bridging oligos for effective hybridisation to the nucleic acid sensors, but the length of bridging oligo that can be detected is limited in a physical respect, since the catalytic domain must be brought into contact for germination to occur.

EXAMPLE 4

Making a Bacterial Spore Sensor of MRSA

Methods

Similar methods to those described in Example 3 were employed. Two short biotinylated DNA sequences from the DNA of the MRSA mecA gene were attached to the *B. subtilis* prkC-SAV protein on bacterial spores using standard molecular biology techniques. The MRSA oligos had the following sequences:

```
                                          (SEQ ID NO: 15)
    MRSA left: Biotin TTCCAGATTA (SEQ ID NO: 16)
    MRSA right: CAACTTCACCA Biotin
```

The spores were incubated in the presence of a DNA sample containing a mecA target 'bridging' oligo (TGGTGAAGTTGTAATCTGGAA; SEQ ID NO: 17), or a control sample without mecA, as shown schematically in FIG. 20. The spores were allowed to germinate, and the germination was measured using Terbium ions and fluorescence as shown in FIG. 19.

Results

As shown in FIG. 21, incubation of the bacterial spores with attached mecA DNA sequences, in the presence of a sample containing mecA DNA, resulted in increased fluorescence compared to the control sample.

Discussion

This is proof of concept of a very simple, rapid and sensitive biosensor for detecting the presence of MRSA, which has enormous potential for reducing MRSA infections.

EXAMPLE 5

Signal Amplification of Nucleic Acid Inputs

Introduction

A common obstacle in developing biosensors is the ability to detect tiny amounts of analyte in mixed samples from patients or from the environment, for example. Seelig et al (2006) developed a series of enzyme free nucleic acid logic circuits in which gate design and circuit structure is modular and the circuit mechanism depends exclusively on nucleic acid sequence recognition and strand displacement. We combined their amplification circuit (FIG. 22) with our system for nucleic acid-dependant germination to detect the output signal.

In brief, we designed biotinylated nucleic acid 'sensors' that hybridise to the output signal ($R_{out}$). The amplifier complex is in a metastable conformation but upon addition of input miR-143, which binds to one arm of the complex and causes a conformational rearrangement. This leads to the production of two 'waste' products, an output strand that is detected by PrkC-SAV spores with bound biotinylated 'sensors', and the initial input signal that is then available to bind to another amplifier complex.

Methods

Similar methods to those described in Example 3 were employed to prepare bacterial spores that act as a read-out for DNA-based computation. Two short biotinylated DNA sequences were attached to the *B. subtilis* prkC-streptavidin protein on bacterial spores using standard molecular biology techniques. The oligos had the following sequences:

```
                                          (SEQ ID NO: 18)
    left: Biotin ATAAACACCT,
    and (SEQ ID NO: 19)
    right: CCAATTCATC Biotin.
```

As described in FIG. 22, taken from Seelig et al (2006), a signal propagation/amplification DNA circuit was prepared using miR-143 TGAGATGAAGCACTGTAGCTCA (SEQ ID NO: 20) as the input. The output oligo $R_{out}$ GATGAATTGGAGGTGTTTATAGCGGACCCCTACTGAGTTGTG (SEQ ID NO: 21) from the circuit acts as a 'bridging' oligo that binds to the two biotinylated oligos attached to the spores.

Results

The spores were incubated in the presence of DNA circuit and appropriate controls. As shown schematically in FIG. 23, the spores were allowed to germinate, and the germination was measured by fluorescent detection of DPA release. FIG. 24 shows that significantly increased levels of germination were detected in the 'Gate+input' sample, corresponding to the increased level of signal following amplification through the circuit. Further, as shown in FIG. 24, the DNA signal amplification circuit resulted in a geometric increase in the signal output at increasing concentrations, compared to the expected arithmetic increase in signal output at increasing concentrations of output oligo alone.

Discussion

This demonstrates that DNA circuits for signal propagation/amplification can be used in conjunction with modified bacterial spores to act as simple, rapid and sensitive biosensors for detecting the presence of a 'target' nucleic acid molecule.

EXAMPLE 6

Click Reaction Dependant Germination

Introduction

Click chemistry proceeds via triazole bond formation of an azide and alkyne in the presence of copper (Breinbauer and Köhn, 2003 "Azide-alkyne coupling: a powerful reaction for bioconjugate chemistry". *Chembiochem.* 4(11): 1147-9. When the azide and alkyne components are biotinylated, formation of the triazole bond in the presence of bacterial spores expressing prkC-SAV, can lead to dimerisation of the prkC-SAV and germination of the spores.

Methods

Bacterial spores expressing a prkC-streptavidin fusion protein (prkC-SAV) were prepared as described in Example 3. PrkC-SAV expressing spores were incubated in the presence of biotinylated azide and alkyne groups with copper (FIG. 25). DPA release, i.e. germination, was measured by fluorescence in the presence of terbium as described in previous Examples.

Results

A significant increase in germination was observed in the presence of all components required for the click reaction to proceed compared to controls that omit either the biotinylated azide and alkyne or the copper from the reaction (FIG. 26).

Discussion

Spore germination in the presence of bond formation due to the presence of copper may allow detection of copper in the environment. This can be extended to detecting other environmental conditions.

Increasing spore concentration in these germination reactions may increase DPA concentration such that any background fluorescence becomes insignificant in comparison.

EXAMPLE 7

Detection of Synthetic Receptors Using Aptamers

Fredriksson et al (2002) describes a method for protein detection, in which the coordinated and proximal binding of a target protein by two DNA aptamers promotes ligation of oligonucleotides linked to each aptamer affinity probe. The ligation of two such proximity probes gives rise to an amplifiable DNA sequence that reflects the identity and amount of the target protein. However, bacterial spores can provide an alternative readout.

Pairs of DNA aptamers that bind a target protein can be designed as described by Fredriksson et al. As shown in FIG. 27, these aptamers can be attached to a bacterial spore via the prkC protein, for example by biotinylation of the aptamers and attachment to a bacterial spore expressing prkC-SAV. Presence of the target protein results in binding of the protein by the aptamers, dimerisation of the prkC proteins, and germination of the spores, which can be detected, for example, using methods described in previous Examples.

As shown in FIG. 28, this method has been used to detect the presence of platelet derived growth factor, in the BB homodimer form (PDGF-BB). In this example, optimal detection was achieved with 0.1 nM of target protein.

EXAMPLE 8

Protein Detection Using Structure-Switching Aptamers

Hall et al (2009) describe a method for protein detection using structure switching aptamers. The well-known example of thrombin as a target, described in the Introduction by Hall et al, was utilised to assess the use of bacterial spores as an alternative readout to release of a quencher from a fluorophore, as illustrated in FIGS. 29-30.

As shown in FIG. 29, in the presence of thrombin the release of the 'quencher' oligo Q-AGTCGTTCAG-5' (SEQ ID No: 26) from the fluorophore oligo 5'-F-TCAGCAAGTC-CGTGGTAGGGCAGGTTGGGGTGACT (SEQ ID No: 27) can be detected by binding to pairs of complementary oligos attached by biotin to prkC-SAV on bacterial spores. This results in dimerisation of the prkC proteins, and germination of the spores, which can be detected, for example, using methods described in Example 3.

As shown in FIG. 30, this method has been used to detect the presence of thrombin, with optimal detection was achieved at 100 nm of target protein. It is appreciated, however, that other structure-switching signalling aptamers, such as those described by Nutiu & Li (2005) can benefit from using this bacterial-spore detection technology.

General Discussion of the Examples

In these Examples, the inventors have demonstrated a proof of principle for programmable engineered spore germination. Using the methodology developed here, new ligand specificities can be engineered to trigger germination by constructing new chimeric prkC proteins with alternative extracellular dimerisation domains. Spores can be engineered to germinate in response to a variety of pathogen and disease markers, as well as small molecules and metabolites, either through rational protein-design using structural information or by directed evolution of proteins (Johannes and Zhao, 2006), effectively creating a small ligand binding library of proteins capable of dimerisation. The use of engineered spore germination has applications in fields such as bioproduct delivery, biosensors and bioremediation and provides attractive advantages over other bacterial systems in these areas.

Biosensors are typically designed to use a specific bioactive component for analytical detection, yielding a signal that can monitor the analyte concentration. Spores can be engineered to respond to specific markers to act as biosensors and since ion secretion is an inherent consequence of spore germination, can be integrated with electronic devices such as ion-selective field effect transistors to transduce the ion secretion to an electronic signal. Signal detection by germination can provide a rapid response in comparison to conventional analytical methods such as enzyme-linked immunosorbent assay (ELISA) and other microbial biosensors since detection is likely to be faster than processes that rely on protein expression as reporter systems (Sorensen et al. 2006). The immobilisation of bacteria is an important factor of design since immobilization can affect the microbial biosensor response, operational stability and its long-term use. For example some immobilization methods of bacteria include chemical treatment where whole cells are exposed to harmful chemicals and harsh reaction conditions that can damage the cell membrane and decrease the biological activity, or by entrapment of bacteria which can result in lower sensitivity and detection due to diffusion resistance incurred by the material enclosing the bacteria (Lei et al. 2006). Spores can withstand harsh chemical treatments and difficulty in laboratory handling is greatly reduced since spores can survive desiccated at room temperature, allowing for easier integration into electronic devices.

*Bacillus subtilis* is recognized as a safe (GRAS) organism and is able to over produce and secrete large quantities of endogenous proteins for industrial purposes (Wester et al. 2004), although the secretion of heterologous proteins is known to be less efficient than native proteins (Li et al. 2004). Spores could be engineered to express enzymes to degrade environmental contaminants for bioremediation. Several *Bacillus* species have been identified that can naturally digest hydrocarbons. *Bacillus cereus* for example, can digest the hydrocarbon n-hexadecane and the optimal conditions for enzyme production have been established (Chen et al. 2009), and a strain of *Bacillus subtilis* (DM-04) isolated from a petroleum contaminated soil sample from North-East India can utilize crude petroleum-oil hydrocarbons as its sole source of carbon and energy (Das and Mukherjee, 2007). Nevertheless, research into the secretion mechanisms of *Bacillus* is improving the efficiency of heterologous protein secretion (Harwood and Cranenburgh, 2007; Chiang et al. 2010) and it can be envisioned that a variety of enzymes could be engineered for expression in *Bacillus*. A current drawback of using live cells for bioremediation is that the integrity of the degradative enzymes produced may be compromised due to deleterious mutations in the growing cells. Spores on the other hand could be engineered to germinate in response to a contaminant and express degradative enzymes, serving as a negative feedback mechanism of regulation. Spores could therefore be applied proactively to environmental hazard areas and persist in the environment until they are needed.

The use of bacterial vectors for macromolecular (gene or protein) delivery is developing in several bacterial systems (Parsa and Pfeifer, 2007) as an alternative to viral vectors. Many studies using bacteria for various macromolecular therapies focus on the treatment of cancer, delivering bioproducts to tumorous cells (Barbe et al (2006) "The use of clostridial spores for cancer treatment". *J Appl Microbiol* 101: 571-578; Anderson et al (2006) "Environmentally controlled invasion of cancer cells by engineered bacteria". *J Mol Biol.* 355(4): 619-27.). Recently, a recombinant and suicidal plasmid strain of *Listeria* r(sΔ2) was generated capable of delivering antigens as protein or DNA into nondividing intestinal epithelial cells, where protein delivery was found to be more effective than delivery of its gene counterpart (Kuo et al. 2009). These delivery systems involve uptake of the bacteria into the host cytosol but there have been studies of protein delivery via so called alternative gene therapy where the bacteria do not enter the eukaryotic cell, but express the therapeutical transgene in the intercellular space (PaIffy et al. 2006). This mechanism of delivering cytosine deaminase (CD) in the therapy of colorectal cancer using *Clostridium* strains have been described (Minton, 2003) and clinical trials of genetically modified probiotic bacteria for therapy of gastrointestinal disorders are reviewed in Gareau et al. (2010). However, the potential of these live bacterial cell therapies are limited by low viability of bacteria due to harsh gastrointestinal conditions, which cannot necessarily be compensated for by larger quantities since orally administered live bacterial cells may stimulate a host immune response (Prakash and Jones, 2005).

Spores of *Bacillus subtilis* are used as probiotics for both human and animal consumption, for treatment of mild gastrointestinal disorders or as nutritional supplements (Casula and Cutting, 2002). Beneficial effects of ingesting spores of *B. subtilis* have been observed on growth, performance, feed conversion, and meat quality in farm animals (Link and Kovac 2006). However, the mechanism behind this attribute is not well understood and animal feed is currently supplemented with purified enzymes such as phytases and cellulases to improve nutritional value, that are expensive to produce and are difficult to locate in an active form to the GI tract (Choct, 2006). Although *Bacillus* species are found in soil, dust, and water and air environments, increasing evidence suggests that *Bacillus* spore formers have adapted to live and survive within the gastro-intestinal tract and are capable of developing a symbiotic relationship with their host (Tam et al. 2006).

Recently, an inner-spore coat protein of *B. subtilis* has been engineered to expose a functional endogenous phytase at the spore surface for this purpose (Potot et al. 2010). However, it has not been tested whether the activity of the exposed phytase in these spores would be affected by acids or proteases found in the gastrointestinal tract. Using the system we have described in this study, it may be possible to engineer spores to overexpress and secrete large amounts of enzymes in the GI tract, with the advantage of specific protein production in response to different ligands using mutant strains of *B. subtilis* lacking germinant receptors. Other applications of spores for macromolecule delivery includes their potential use as vehicles of foreign antigens in development of new vaccines, following a demonstrated strong cell-mediated immune responses in mice by engineered antigens on the spore surface (Mauriello et al. 2007; reviewed in Cutting et al. 2009). The increasing realisation of the potential of spores for bioproduct delivery indicates the remarkable benefits that can be achieved with the present invention.

REFERENCES

Paidhungat & Setlow (2000) "Role of Ger Proteins in Nutrient and Normutrient Triggering of Spore Germination in *Bacillus subtilis*". *J. Bacteriology* 182(9): 2513-2519.

Purohit H J (2003) "Biosensors as molecular tools for use in bioremediation". *Journal of Cleaner Production* 11: 293-301.

Lei, Chen & Mulchandani (2006) "Microbial biosensors". *Analytica Chimica Acta* 568(1-2): 200-210.

Sørensen, Burmølle and Hansen (2006) "Making bio-sense of toxicity: new developments in whole-cell biosensors". *Current Opinion in Biotechnology* 17: 11-16.

Li, Zhou & Lu (2004) "Bottlenecks in the expression and secretion of heterologous proteins in *Bacillus subtilis*". *Res. Microbiol.* 155(8): 605-610.

Westers, Westers & Quax (2004) "*Bacillus subtilis* as cell factory for pharmaceutical proteins: a biotechnological approach to optimize the host organism". *Biochim. Biophys. Acta:* 1694(1-3): 299-310.

Harwood & Cranenburgh (2008) "*Bacillus* protein secretion: an unfolding Story." *Trends in Microbiology* 16(2): 73-79.

Chiang, Chen & Chao (2010) "Secreted Production of *Renilla* Luciferase in *Bacillus subtilis*". *Biotechnol. Prog.* 26(2): 589-594.

Chen, Wang & Qin (2009) "Degradability of n-hexadecane by *Bacillus cereus* DQ01 isolated from oil contaminated soil from Daqing oil field, China". *International Journal of Environment and Pollution.* 38(1-2): 100-115.

Das & Mukherjee (2007) "Crude petroleum oil biodegradation efficiency of *Bacillus subtilis* and *Pseudomonas aeruginosa* strains isolated from petroleum oil contaminated soil from North East India." *Bioresour. Technol.,* 98(7): 1339-1345.

Brooijmans, Pastink & Siezen (2009) "Hydrocarbon degrading bacteria: the oil-spill clean-up crew". *Miocrob. Biotechnol.,* 2(6): 587-594.

Terpe, K (2006) "Overview of bacterial expression systems for heterologous protein production: from molecular and biochemical fundamentals to commercial systems". *Applied Microbiology and Biotechnology* 72(2): 211-222.

Parsa & Pfeifer (2007) "Engineering Bacterial Vectors for Delivery of Genes and Proteins to Antigen-Presenting Cells" *Mol. Pharmaceutics* 4(1): 4-17

Kuo, Sinha, Jazayeri, and Pouton (2009) "A Stably Engineered, Suicidal Strain of *Listeria monocytogenes* Delivers Protein and/or DNA to Fully Differentiated Intestinal Epithelial Monolayers". *Mol. Pharmaceutics* 6(4): 1052-1061.

Minton N P. (2003) "Clostridia in cancer therapy" *Nat Rev Microbiol* 1(3): 237-242.

Gareau, Sherman & Walker (2010) "Probiotics and the gut microbiota in intestinal health and disease" Nature Reviews|*Gastroenterology & Hepatology* 7(9): 503-514.

Prakash & Jones (2005) "Artificial Cell Therapy: New Strategies for the Therapeutic Delivery of Live Bacteria" *Journal of Biomedicine and Biotechnology* 2005(1): 44-56.

Choct, M. (2006). "Enzyme for the feed industry: past, present and future". *World's Poultry Sci J.* 62: 6-16

Potot, Serra, Henriques & Schyns (2010) "Display of recombinant proteins on *Bacillus subtilis* spores, using a coat-associated enzyme as the carrier". *Appl. Environ. Microbiol.* 76(17): 5926-5933.

Casula & Cutting (2002) "*Bacillus* probiotics: spore germination in the gastrointestinal tract." *Appl. Environ. Microbiol.* 68(5): 2344-2352.

Leser, Knarreborg & Worm (2008) "Germination and outgrowth of *Bacillus subtilis* and *Bacillus licheniformis* spores in the gastrointestinal tract of pigs". *Journal of Applied Microbiology* 104(4): 1025-33.

Salis, Mirsky & Voigt (2009) "Automated design of synthetic ribosome binding sites to control protein expression". *Nature Biotechnology* 27: 946-950.

Mauriello, Cangiano, Maurano, Saggese, Felice, Rossi & Ricca (2007) "Germination-independent induction of cellular immune response by *Bacillus subtilis* spores displaying the C fragment of the tetanus toxin" *Vaccine* 25(5): 788-793.

Cutting, Hong, Baccigalupi & Ricca (2009) "Oral Vaccine Delivery by Recombinant Spore Probiotics" *International Reviews of Immunology,* 28(6): 487-505.

Johannes & Zhao (2006) "Directed evolution of enzymes and biosynthetic pathways" *Current Opinion in Microbiology* 9(3): 261-267.

Hudson et al (2001) "Localization of GerAA and GerAC Germination Proteins in the *Bacillus subtilis* Spore" *J. Bacteriol.* 183(14): 4317-4322

Fredriksson et al (2002) "Protein detection using proximity-dependent DNA ligation assays" *Nature Biotechnology* 20: 473-377.

Nutiu & Li (2005) "In Vitro Selection of Structure-Switching Signaling Aptamers" *Angew. Chem.* 117: 1085-1089.

Hall et al (2009) "Kinetic Optimization of a Protein-Responsive Aptamer Beacon" *Biotechnol. Bioeng.* 103: 1049-1059.

Seelig et al (2006) "Enzyme-Free Nucleic Acid Logic Circuits" *Science* 314, 1585-88.

The invention claimed is:

1. A bacterial spore which has been modified such that the spore undergoes germination in the presence of a germinant which does not stimulate germination of an equivalent unmodified bacterial spore, wherein the germinant is a germinant chosen from the group consisting of an antibiotic, a hormone, a growth factor, a steroid, a neurotransmitter, and DNA.

2. A bacterial spore comprising a modified gerA protein, wherein the gerA protein has been modified such that the spore undergoes germination in the presence of a germinant which does not stimulate germination of a bacterial spore comprising wild-type gerA protein.

3. The bacterial spore of claim 1, wherein the spore comprises a modified prkC protein.

4. The bacterial spore of claim 3, wherein the modified prkC protein comprises at least 90% of the amino acid sequence of SEQ ID NO: 14.

5. The bacterial spore of claim 3, wherein the spore undergoes germination in the presence of a germinant which does not stimulate germination of a bacterial spore comprising wild-type prkC protein.

6. The bacterial spore of claim 1, wherein the spore comprises a modified gerA protein.

7. The bacterial spore of claim 6, wherein the spore undergoes germination in the presence of a germinant which does not stimulate germination of a bacterial spore comprising wild-type gerA protein.

8. The bacterial spore of claim 1, wherein the spore comprises a modified prkC protein and a modified gerA protein.

9. The bacterial spore of claim 8, wherein the spore undergoes germination in the presence of a germinant which does not stimulate germination of a bacterial spore comprising wild-type prkC protein and wild-type gerA protein.

10. The bacterial spore of claim 8, wherein the extracellular domain of the modified prkC and gerA proteins bind an agent which is not bound by the extracellular domain of a wild-type prkC protein, and wherein the agent is a germinant that stimulates germination of the bacterial spore.

11. The bacterial spore of claim 8, wherein the extracellular domain of the modified prkC and gerA proteins bind an agent which is not bound by the extracellular domain of a wild-type gerA protein, and wherein the agent is a germinant that stimulates germination of the bacterial spore.

12. A bacterial spore which has been modified such that the spore undergoes germination in the presence of a germinant which does not stimulate germination of an equivalent unmodified bacterial spore, wherein the germinant is an environmental contaminant, and wherein the bacterial spore has been engineered to express an enzyme that degrades the environmental contaminant after germination.

13. The bacterial spore of claim 12, wherein the spore comprises a modified prkC protein.

14. The bacterial spore of claim 13, wherein the modified prkC protein comprises at least 90% of the amino acid sequence of SEQ ID NO: 14.

15. The bacterial spore of claim 12, wherein the spore undergoes germination in the presence of a germinant which does not stimulate germination of a bacterial spore comprising wild-type prkC protein.

16. The bacterial spore of claim 12, wherein the spore comprises a modified gerA protein.

17. The bacterial spore of claim 12, wherein the spore comprises a modified prkC protein and a modified gerA protein.

18. A bacterial spore comprising a modified prkC protein, wherein the intracellular domain and the transmembrane domain of the modified prkC protein have the native sequence, and the extracellular domain of the modified prkC protein binds an agent which is not bound by the extracellular domain of the wild-type prkC protein, and wherein the agent is a germinant that stimulates germination of the bacterial spore.

19. The bacterial spore of claim 18, wherein the modified prkC protein comprises at least 90% of the amino acid sequence of SEQ ID NO: 14.

20. The bacterial spore of claim 18, wherein the bacterial spore has been engineered to express an enzyme which improves digestibility of animal feed after germination.

21. The bacterial spore of claim 18, further comprising modified gerA protein.

22. The bacterial spore of claim 2, wherein the extracellular domain of the modified gerA protein binds an agent which is not bound by the extracellular domain of the wild-type gerA protein, and wherein the agent is a germinant that stimulates germination of the bacterial spore.

23. The bacterial spore of claim 2, further comprising modified prkC protein.

* * * * *